United States Patent [19]

Addor et al.

[11] Patent Number: 5,480,902

[45] Date of Patent: Jan. 2, 1996

[54] THIENYLPYRROLE FUNGICIDAL AGENTS

[75] Inventors: Roger W. Addor, Pennington; Joseph A. Furch, III, Lawrenceville; Laurelee A. Duncan, East Windsor, all of N.J.

[73] Assignee: American Cyanamid Company, Wayne, N.J.

[21] Appl. No.: 114,810

[22] Filed: Aug. 31, 1993

[51] Int. Cl.[6] .......... A61K 31/38; A61K 31/40; A61K 31/415; A61K 31/42

[52] U.S. Cl. .......... 514/422; 514/427; 514/367; 514/369; 514/375; 514/376; 514/397; 514/414; 514/343; 514/326; 549/61; 549/68; 549/49; 549/441; 549/73; 548/228; 548/527

[58] Field of Search ................ 514/422, 427, 514/367, 369, 375, 376, 397, 414, 343, 326; 548/527, 517, 525, 527, 165, 169, 170, 171, 173, 182, 186, 187, 217, 221, 225, 229, 306.1, 465, 406, 413; 546/281, 208; 544/55, 96, 315

[56] References Cited

U.S. PATENT DOCUMENTS

| | | | |
|---|---|---|---|
| 4,267,184 | 5/1981 | Cherkofsky | 424/263 |
| 4,883,807 | 11/1989 | Clough et al. | 514/427 |
| 5,010,098 | 4/1991 | Brown et al. | 514/426 |
| 5,091,407 | 2/1992 | deFraine et al. | 514/423 |
| 5,102,904 | 4/1992 | Kameswaren | 514/424 |
| 5,157,047 | 10/1992 | Kaweswaren et al. | 514/423 |
| 5,162,308 | 11/1992 | Brown et al. | 514/63 |
| 5,284,863 | 2/1994 | Barnes et al. | 514/427 |

FOREIGN PATENT DOCUMENTS

| | | |
|---|---|---|
| 111452A1 | 6/1984 | European Pat. Off. . |
| 60-40874 | 3/1985 | Japan . |

OTHER PUBLICATIONS

N. Ono, et al., Journal of Heterocyclic Chemistry, 28, pp. 2053–2055 (1991).

Primary Examiner—Glennon H. Hollrah
Assistant Examiner—Mary C. Cebulak
Attorney, Agent, or Firm—Gregory M. Hill

[57] ABSTRACT

There are provided fungicidal thienyl- and furylpyrrole compounds of formula I

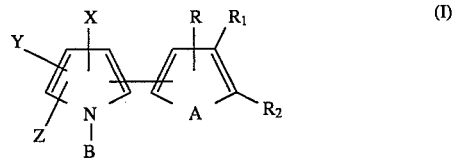

Further provided are compositions and methods comprising those compounds for the protection of plants from fungal infestation and disease.

20 Claims, No Drawings

THIENYLPYRROLE FUNGICIDAL AGENTS

BACKGROUND OF THE INVENTION

Phytopathogenic fungi are the causal agents for many diseases that infect and destroy crops. In particular, the diseases apple scab, grape downy mildew, wheat leaf rust and wheat powdery mildew are especially devastating.

In spite of the commercial fungicides available today, diseases caused by fungi still abound. Accordingly, there is ongoing research to create new and more effective fungicides for controlling or preventing diseases caused by phytopathogenic fungi.

Certain pyrrole compounds are known to possess acaricidal, fungicidal, insecticidal and/or antiinflammatory activity (see, e.g., U.S. Pat. Nos. 4,267,184; 5,010,098; 5,102,904; 5,157,047 and 5,162,308, United States patent application Ser. Nos. 621,162 filed on Nov. 30, 1990; 803,289 filed on Dec. 4, 1991; 966,990 filed on Oct. 27, 1992; 966,992 filed on Oct. 27, 1992; 967,091 filed on October 27, 1992 and 971,025 filed on November 11, 1992, Japanese Patent Application JP-85-40874 filed on Mar. 1, 1985, European Patent Application EP-111452-A1 filed on Jun. 20, 1984, and N. Ono et al, Journal of Heterocyclic Chemistry, 28, pages 2053–2055 (1991)). However, none of the pyrroles disclosed in those patents, patent applications and publication are within the scope of the present invention.

It is therefore an object of the present invention to provide a method for the prevention, control or amelioration of a disease caused by a phytopathogenic fungus.

It is also an object of the present invention to provide a method for the protection of a plant, plant seed or tuber from fungal infestation and disease.

These and other objects of the present invention will become more apparent from the detailed description thereof set forth below.

SUMMARY OF THE INVENTION

The present invention relates to a method for the prevention, control or amelioration of a disease caused by a phytopathogenic fungus by contacting said fungus with a fungicidally effective amount of a thienyl- or furylpyrrole compound having the following structural formula I:

wherein

R, $R_1$ and $R_2$ are each independently hydrogen, halogen, $NO_2$ or CHO, and when $R_1$ and $R_2$ are taken together with the carbon atoms to which they are attached, they may form a ring in which $R_1R_2$ is represented by the structure:

$$-\overset{L}{C}=\overset{T}{C}-\overset{V}{C}=\overset{W}{C}-;$$

L, T, V and W are each independently hydrogen, halogen, CN or $NO_2$;

A is O or S;

X is CN, $NO_2$, $C_1$–$C_6$ haloalkyl, $S(O)_mCF_2R_3$ or $C(S)NR_4R_5$;

$R_3$ is hydrogen, F, Cl, Br, $CF_2H$, $CCl_2H$, $CClFH$, $CF_3$ or $CCl_3$;

m is an integer of 0, 1 or 2;

$R_4$ and $R_5$ are each independently hydrogen,
  $C_1$–$C_4$ alkyl optionally substituted with one or more halogen atoms, or phenyl optionally substituted with one or more halogen atoms,
  $NO_2$ groups,
  CN groups,
  $C_1$–$C_4$ alkyl groups optionally substituted with one or more halogen atoms, or
  $C_1$–$C_4$ alkoxy groups optionally substituted with one or more halogen atoms;

Y is hydrogen, halogen, $C_1$–$C_6$ haloalkyl, $S(O)_mCF_2R_3$, CN or phenyl optionally substituted with one or more halogen atoms,
  $NO_2$ groups,
  CN groups,
  $C_1$–$C_4$ alkyl groups optionally substituted with one or more halogen atoms, or
  $C_1$–$C_4$ alkoxy groups optionally substituted with one or more halogen atoms;

Z is hydrogen, halogen or $C_1$–$C_6$ haloalkyl;

B is $R_6$, $OR_6$ or CN;

$R_6$ is hydrogen, $C(O)R_7$, $CHR_8NHC(O)R_9$, $CH_2SQ$, $CHR_{10}OC(O)(CR_{11}R_{12})_nQ_1$,
  $C_1$–$C_6$ alkyl optionally substituted with one to three halogen atoms,
    one tri($C_1$–$C_4$ alkyl)silyl,
    one hydroxy,
    one cyano,
    one or two $C_1$–$C_4$ alkoxy groups optionally substituted with one to three halogen atoms,
    one $C_1$–$C_4$ alkylthio,
    one phenyl optionally substituted with one to three halogen atoms, one to three $C_1$–$C_4$ alkyl groups or one to three $C_1$–$C_4$ alkoxy groups,
    one phenoxy group optionally substituted with one to three halogen atoms, one to three $C_1$–$C_4$ alkyl groups or one to three $C_1$–$C_4$ alkoxy groups,
    one benzyloxy group optionally substituted on the phenyl ring with one to three halogen atoms, one to three $C_1$–$C_4$ alkyl groups or one to three $C_1$–$C_4$ alkoxy groups,
    one $C_1$–$C_6$ alkylcarbonyloxy group optionally substituted with one to three halogen atoms,
    one $C_2$–$C_6$ alkenylcarbonyloxy group optionally substituted with one to three halogen atoms,
    one phenylcarbonyloxy group optionally substituted with one to three halogen atoms, one to three $C_1$–$C_4$ alkyl groups or one to three $C_1$–$C_4$ alkoxy groups,
    one $C_1$–$C_6$ alkoxycarbonyl group optionally substituted with one to three halogen atoms or one to three $C_1$–$C_4$ alkoxy groups, or
    one benzylcarbonyloxy group optionally substituted on the phenyl ring with one to three halogen atoms, one to three $C_1$–$C_4$ alkyl groups or one to three $C_1$–$C_4$ alkoxy groups,
  $C_3$–$C_6$ alkenyl optionally substituted with one to three halogen atoms or one phenyl group, or
  $C_3$–$C_6$ alkynyl optionally substituted with one to three halogen atoms or one phenyl group;

$R_7$ is $C_1$–$C_6$ alkyl or $C_3$–$C_6$ cycloalkyl each optionally substituted with one to three halogen atoms, one hydroxy,
one cyano,
one or two $C_1$–$C_4$ alkoxy groups optionally substituted with one to three halogen atoms,
one $C_1$–$C_4$ alkylthio,
one phenyl group optionally substituted with one to three halogen atoms,
one to three $C_1$–$C_4$ alkyl groups or
one to three $C_1$–$C_4$ alkoxy groups,
one phenoxy group optionally substituted with one to three halogen atoms,
one to three $C_1$–$C_4$ alkyl groups or
one to three $C_1$–$C_4$ alkoxy groups,
one benzyloxy group optionally substituted on the phenyl ring with one to three halogen atoms, one to three $C_1$–$C_4$ alkyl groups or one to three $C_1$–$C_4$ alkoxy groups,
one $C_1$–$C_6$ alkylcarbonyloxy group optionally substituted with one to three halogen atoms,
one $C_2$–$C_6$ alkenylcarbonyloxy group optionally substituted with one to three halogen atoms,
one phenylcarbonyloxy group optionally substituted with one to three halogen atoms, one to three $C_1$–$C_4$ alkyl groups or one to three $C_1$–$C_4$ alkoxy groups,
one $C_1$–$C_6$ alkoxycarbonyl group optionally substituted with one to three halogen atoms or one to three $C_1$–$C_4$ alkoxy groups, or
one benzyloxycarbonyl group optionally substituted on the phenyl ring with one to three halogen atoms, one to three $C_1$–$C_4$ alkyl groups or one to three $C_1$–$C_4$ alkoxy groups,
$C_2$–$C_6$ alkenyl optionally substituted with one to three halogen atoms or one phenyl group,
$C_3$–$C_6$ alkynyl optionally substituted with one to three halogen atoms or one phenyl group,
phenyl optionally substituted with one or more halogen atoms, $C_1$–$C_4$ alkyl groups, $C_1$–$C_4$ alkoxy groups, phenoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups,
phenoxy optionally substituted with one or more halogen atoms, $C_1$–$C_4$ alkyl groups, $C_1$–$C_4$ alkoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups,
1- or 2-naphthyl,
2-, 3-, or 4-pyridyl optionally substituted with one to three halogen atoms,
$C_1$–$C_6$ alkoxy optionally substituted with one to three halogen atoms, or
$C_2$–$C_6$ alkenyloxy optionally substituted with one to three halogen atoms;

$R_8$ is hydrogen or $C_1$–$C_4$ alkyl;

$R_9$ is $C_1$–$C_6$ alkyl optionally substituted with one to three halogen atoms,
phenyl optionally substituted with one to three halogen atoms, CN groups, $NO_2$ groups, $C_1$–$C_4$ alkyl groups, $C_1$–$C_4$ alkoxy groups or $CF_3$ groups, 2- or 3-thienyl, or 2- or 3-furyl;

Q is

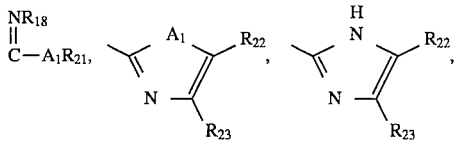

CN,
$C_1$–$C_6$ alkyl optionally substituted with one or more halogen atoms, CN groups or phenyl groups, or phenyl optionally substituted with one or more halogen atoms, $C_1$–$C_4$ alkyl groups, $C_1$–$C_4$ alkoxy groups, CN groups, $NO_2$ groups, $CF_3$ groups or $NR_{24}R_{25}$ groups;

$A_1$ is O or S;

$R_{13}$ is $C_1$–$C_6$ alkyl or phenyl;

$R_{14}$ is $C_1$–$C_6$ alkyl;

$R_{15}$ and $R_{16}$ are each independently hydrogen, $C_1$–$C_6$ alkyl or may be taken together with the atom to which they are attached to form a 5- to 7-membered ring;

$R_{17}$ is $C_1$–$C_4$ alkyl;

$R_{18}$ is hydrogen, $C_1$–$C_4$ alkyl or may be taken together with either $R_{19}$ or $R_{21}$ and the atoms to which they are attached to form a 5- to 7-membered ring optionally substituted with one or two $C_1$–$C_4$ alkyl groups;

$R_{19}$ and $R_{20}$ are each independently hydrogen or $C_1$–$C_4$ alkyl;

$R_{21}$ is $C_1$–$C_4$ alkyl or when taken together with $R_{18}$ and the atoms to which they are attached may form a 5- to 7-membered ring optionally substituted with one or two $C_1$–$C_4$ alkyl groups;

$R_{22}$ and $R_{23}$ are each independently hydrogen or $C_1$–$C_4$ alkyl or when taken together may form a ring wherein $R_{22}R_{23}$ is represented by —CH=CH—CH=CH—;

$R_{24}$ and $R_{25}$ are each independently hydrogen or $C_1$–$C_4$ alkyl;

$R_{10}$ is hydrogen or $C_1$–$C_4$ alkyl;

$R_{11}$ and $R_{12}$ are each independently hydrogen,
$C_1$–$C_6$ alkyl optionally substituted with one or more halogen atoms,
$C_1$–$C_6$ alkoxy optionally substituted with one or more halogen atoms,
$C_1$–$C_6$ alkylthio optionally substituted with one or more halogen atoms, or phenyl optionally substituted with one or more halogen atoms,
$NO_2$ groups;
CN groups,
$C_1$–$C_4$ alkyl groups optionally substituted with one or more halogen atoms, or
$C_1$–$C_4$ alkoxy groups optionally substituted with one or more halogen atoms, or
when $R_{11}$ and $R_{12}$ are taken together with the atom to which they are attached may form a $C_3$–$C_6$ cycloalkyl group optionally substituted with one to three $C_1$–$C_4$ alkyl groups, $C_2$–$C_6$ alkenyl groups or phenyl groups, or $R_{11}$ or $R_{12}$ may be taken together with $R_{26}$ and the atoms to which they are attached to form a 4- to 7-membered heterocyclic ring;

n is an integer of 0, 1, 2, 3 or 4;

$Q_1$ is $A_2R_{26}$, $$\overset{\text{O}}{\underset{\|}{\text{P}}}-(OR_{27})_2,$$

$NR_{28}R_{29}$, $CR_{30}R_{31}C(O)R_{32}$, or $C_3$–$C_6$ cycloalkyl optionally substituted with one or more $C_1$–$C_6$ alkyl groups,
  $C_2$–$C_6$ alkenyl groups, or phenyl groups optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;

$A_2$ is O or $S(O)_p$;

p is an integer of 0, 1 or 2;

$R_{26}$ is hydrogen,
  $C_1$–$C_6$ alkyl
  $C_2$–$C_6$ alkenyl,
  $C_2$–$C_6$ alkynyl,
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms,
  $C(O)R_{33}$ provided p is O,
  $C(O)R_{34}$ provided p is O,
  $(CH_2CH_2O)_qR_{33}$, or $R_{26}$ may be taken together with either $R_{11}$ or $R_{12}$ and the atoms to which they are attached to form a 4- to 7-membered heterocyclic ring;

$A_3$ is O or S;

$R_{33}$ is $C_1$–$C_6$ alkyl,
  $C_2$–$C_6$ alkenyl,
  $C_2$–$C_6$ alkynyl, or phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;

q is an integer of 1, 2 or 3;

$R_{34}$ is $OR_{37}$ or $NR_{38}R_{39}$;

$R_{37}$ is $C_1$–$C_6$ alkyl or phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;

$R_{38}$ and $R_{39}$ are each independently hydrogen or $C_1$–$C_4$ alkyl;

$R_{35}$ and $R_{36}$ are each independently hydrogen or $C_1$–$C_4$ alkyl, or when taken together may form a ring wherein $R_{35}R_{36}$ is represented by —CH=CH—CH=CH—;

$R_{27}$ is $C_1$–$C_4$ alkyl;

$R_{28}$ is hydrogen,
  $C_1$–$C_6$ alkyl,
  $C_2$–$C_6$ alkenyl,
  $C_2$–$C_6$ alkynyl, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms, or
  $R_{28}$ may be taken together with either $R_{11}$ or $R_{12}$ and the atoms to which they are attached to form a 4- to 7-membered heterocyclic ring;

$R_{29}$ is hydrogen,
  $C_1$–$C_6$ alkyl,
  $C_2$–$C_6$ alkenyl,
  $C_2$–$C_6$ alkynyl,
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms,
  $C(A_4)R_{40}$,
  CN,
  $SO_2R_{41}$, or
  $C(O)CHR_{42}NHR_{43}$;

$A_4$ is O or S;

$R_{40}$ is $OR_{44}$, $CO_2R_{44}$, $NR_{45}R_{46}$,
  $C_1$–$C_6$ alkyl optionally substituted with one to three halogen atoms,
  $C_2$–$C_6$ alkenyl,
  $C_2$–$C_6$ alkynyl, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;

$R_{44}$ is $C_1$–$C_6$ alkyl optionally substituted with one phenyl group, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;

$R_{45}$ and $R_{46}$ are each independently hydrogen or $C_1$–$C_4$ alkyl;

$R_{41}$ is $NR_{47}R_{48}$,
  $C_1$–$C_6$ alkyl,
  $C_2$–$C_6$ alkenyl,
  $C_2$–$C_6$ alkynyl, or
  phenyl optionally substituted with one or more halogen atoms, NO₂ groups,
CN groups,
$C_1$–$C_4$ alkyl groups optionally substituted with one or more halogen atoms, or
$C_1$–$C_4$ alkoxy groups optionally substituted with one or more halogen atoms;

$R_{47}$ and $R_{48}$ are each independently hydrogen or $C_1$–$C_4$ alkyl;

$R_{42}$ is hydrogen,
$C_1$–$C_4$ alkyl optionally substituted with one hydroxy group,
one $SR_{49}$ group,
one $C(O)NH_2$ group,
one $NH_2$ group,
one $NHC(=NH)NH_2$ group,
one $CO_2H$ group,
one phenyl group optionally substituted with one hydroxy group,
one 3-indolyl group or
one 4-imidazolyl group;

$R_{49}$ is hydrogen or $C_1$–$C_4$ alkyl;

$R_{43}$ is $C(A_4)R_{50}$;

$R_{50}$ is $C_1$–$C_6$ alkyl optionally substituted with one or more halogen atoms,
$C_1$–$C_6$ alkoxyalkyl,
$C_1$–$C_6$ alkylthio,
phenyl optionally substituted with one or more halogen atoms,
NO₂ groups,
CN groups,
$C_1$–$C_4$ alkyl groups optionally substituted with one or more halogen atoms, or
$C_1$–$C_4$ alkoxy groups optionally substituted with one or more halogen atoms,
$OR_{44}$,
$CO_2R_{44}$ or
$NR_{45}R_{46}$;

$R_{30}$ and $R_{31}$ are each independently hydrogen,
$C_1$–$C_6$ alkyl optionally substituted with one or more halogen atoms,
$C_1$–$C_6$ alkoxy optionally substituted with one or more halogen atoms,
$C_1$–$C_6$ alkylthio optionally substituted with one or more halogen atoms,
phenyl optionally substituted with one or more halogen atoms,
CN groups,
NO₂ groups,
$C_1$–$C_4$ alkyl groups optionally substituted with one or more halogen atoms, or
$C_1$–$C_4$ alkoxy groups optionally substituted with one or more halogen atoms, or
when $R_{30}$ and $R_{31}$ are taken together with the atom to which they are attached may form a $C_3$–$C_6$ cycloalkyl group optionally substituted with one to three $C_1$–$C_4$ alkyl groups, $C_2$–$C_6$ alkenyl groups or phenyl groups;

$R_{32}$ is $OR_{51}$, $NR_{47}R_{48}$, $C_1$–$C_4$ alkyl or phenyl optionally substituted with one or more halogen atoms,
CN groups,
NO₂ groups,
$C_1$–$C_4$ alkyl groups optionally substituted with one or more halogen atoms, or
$C_1$–$C_4$ alkoxy groups optionally substituted with one or more halogen atoms; and $R_{51}$ is $C_1$–$C_4$ alkyl or phenyl optionally substituted with one or more halogen atoms,
CN groups,
NO₂ groups,
$C_1$–$C_4$ alkyl groups optionally substituted with one or more halogen atoms, or
$C_1$–$C_4$ alkoxy groups optionally substituted with one or more halogen atoms;

provided that when A is S, X is $S(O)_mCF_2R_3$ and Z is hydrogen, then Y is hydrogen, halogen, $C_1$–$C_6$ haloalkyl, $S(O)_mCF_2R_3$ or CN; and further provided that when the pyrrole ring is substituted with hydrogen at each of the pyrrole carbon atoms adjacent to the ring nitrogen atom, then X cannot be CN or NO₂.

This invention also relates to a method for the protection of a plant, plant seed or tuber from fungal infestation and disease.

DETAILED DESCRIPTION OF THE INVENTION

Phytopathogenic fungi are the causal agents for many diseases that infect and destroy agronomic crops, both growing and harvested. In the United States alone, agronomic crops must compete with about 18,000 species of fungi. Especially devastating are diseases such as apple scab, grape downy mildew, wheat leaf rust, wheat powdery mildew and the like. Accordingly, there is ongoing research to create new and more effective fungicides for preventing or controlling the vast array of fungal infestations of crops.

Advantageously, the present invention provides a method for the prevention, control or amelioration of a disease caused by a phytopathogenic fungus by contacting said fungus with a fungicidally effective amount of a formula I thienyl- or furylpyrrole compound.

The present invention also provides a method for the protection of a plant, plant seed or tuber from fungal infestation and disease by applying to the plant, plant seed or tuber, or to the medium or water in which it is growing, a fungicidally effective amount of a formula I thienyl- or furylpyrrole compound.

The term "medium" used herein is defined as any environment, including but not limited to artificial nutrients or soil, in which a plant can be kept, live or thrive.

The fungicidal thienyl- and furylpyrrole compounds of this invention have the following structural formula I:

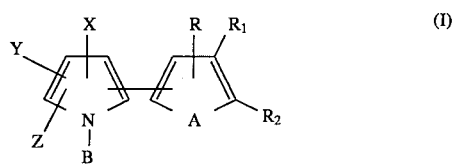

wherein R, $R_1$, $R_2$, A, X, Y, Z and B are as described hereinabove for formula I.

Preferred formula I thienyl- and furylpyrrole fungicidal agents of the present invention are those wherein R, $R_1$ and $R_2$ are each independently hydrogen, halogen or NO₂, and when $R_1$ and $R_2$ are taken together with the carbon atoms to which they are attached, they may form a ring in which $R_1R_2$ is represented by the structure:

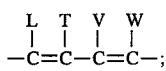

L, T, V and W are each independently hydrogen, halogen, CN or NO$_2$;

A is O or S;

X is CN, NO$_2$, C$_1$–C$_6$ haloalkyl, S(O)$_m$CF$_2$R$_3$ or C(S)NR$_4$R$_5$;

R$_3$ is hydrogen, F, Cl, Br, CF$_2$H, CCl$_2$H, CClFH, CF$_3$ or CCl$_3$;

m is an integer of 0, 1 or 2;

R$_4$ and R$_5$ are each independently hydrogen,
C$_1$–C$_4$ alkyl optionally substituted with one or more halogen atoms, or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

Y is hydrogen, halogen, C$_1$–C$_6$ haloalkyl, S(O)$_m$CF$_2$R$_3$, CN or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

Z is hydrogen, halogen or C$_1$–C$_6$ haloalkyl;

B is R$_6$ or CN;

R$_6$ is hydrogen, C(O)R$_7$, or
C$_1$–C$_6$ alkyl optionally substituted with one to three halogen atoms,
one cyano,
one C$_1$–C$_4$ alkoxy group,
one C$_1$–C$_6$ alkylcarbonyloxy group,
one phenylcarbonyloxy group, or
one benzylcarbonyloxy group; and R$_7$ is phenyl optionally substituted with one or more halogen atoms, C$_1$–C$_4$ alkyl groups, C$_1$–C$_4$ alkoxy groups, CN groups, NO$_2$ groups or CF$_3$ groups.

Another group of preferred formula I fungicidal agents are those wherein

R, R$_1$ and R$_2$ are each independently hydrogen, halogen or NO$_2$, and when R$_1$ and R$_2$ are taken together with the carbon atoms to which they are attached, they may form a ring in which R$_1$R$_2$ is represented by the structure:

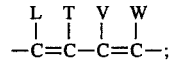

L, T, V and W are each independently hydrogen, halogen, CN or NO$_2$;

A is O or S;

X is CN, NO$_2$ or C$_1$–C$_6$ haloalkyl;

Y is hydrogen, halogen, C$_1$–C$_6$ haloalkyl or phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

Z is hydrogen, halogen or C$_1$–C$_6$ haloalkyl;

B is R$_6$ or CN;

R$_6$ is hydrogen, C(O)R$_7$ or
C$_1$–C$_6$ alkyl optionally substituted with one to three halogen atoms,
one cyano,
one C$_1$–C$_4$ alkoxy group,
one C$_1$–C$_6$ alkylcarbonyloxy group,
one phenylcarbonyloxy group, or
one benzylcarbonyloxy group; and R$_7$ is phenyl optionally substituted with one or more halogen atoms, C$_1$–C$_4$ alkyl groups, C$_1$–C$_4$ alkoxy groups, CN groups, NO$_2$ groups or CF$_3$ groups.

More preferred formula I thienyl- and furylpyrrole fungicidal agents of this invention are those wherein R, R$_1$ and R$_2$ are each independently hydrogen, halogen or NO$_2$, and when R$_1$ and R$_2$ are taken together with the carbon atoms to which they are attached, they may form a ring in which R$_1$R$_2$ is represented by the structure:

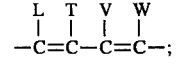

L, T, V and W are each independently hydrogen, halogen, CN or NO$_2$;

A is O or S;

X is CN, NO$_2$ or C$_1$–C$_6$ haloalkyl;

Y is hydrogen, halogen, C$_1$–C$_6$ haloalkyl or phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

Z is halogen or C$_1$–C$_6$ haloalkyl;

B is R$_6$ or CN;

R$_6$ is hydrogen, C(O)R$_7$ or
C$_1$–C$_6$ alkyl optionally substituted with one to three halogen atoms,
one cyano,
one C$_1$–C$_4$ alkoxy group,
one C$_1$–C$_6$ alkylcarbonyloxy group,
one phenylcarbonyloxy group, or
one benzylcarbonyloxy group; and R$_7$ is phenyl optionally substituted with one or more halogen atoms, C$_1$–C$_4$ alkyl groups, C$_1$–C$_4$ alkoxy groups, CN groups, NO$_2$ groups or CF$_3$ groups.

Another group of more preferred formula I thienyl- and furylpyrrole fungicidal agents are those wherein R, R$_1$ and R$_2$ are each independently hydrogen, halogen or NO$_2$, and when R$_1$ and R$_2$ are taken together with the carbon atoms to which they are attached, they may form a ring in which R$_1$R$_2$ is represented by the structure: —CH=CH—CH=CH—;

A is O or S;

X is CN or NO₂;

Y is halogen, CF₃ or
  phenyl optionally substituted with one or more halogen atoms,
  NO₂ groups,
  CN groups,
  $C_1-C_4$ alkyl groups optionally substituted with one or more halogen atoms, or
  $C_1-C_4$ alkoxy groups optionally substituted with one or more halogen atoms;

Z is hydrogen, halogen or CF₃; and

B is hydrogen or $C_1-C_6$ alkyl substituted with one $C_1-C_4$ alkoxy group.

Most preferred formula I fungicidal agents are those wherein

R, $R_1$ and $R_2$ are each independently hydrogen, halogen or NO₂;

A is O or S;

X is CN or NO₂;

Y is halogen, CF₃ or phenyl optionally substituted with one or more halogen atoms,
  NO₂ groups,
  CN groups,
  $C_1-C_4$ alkyl groups optionally substituted with one or more halogen atoms, or
  $C_1-C_4$ alkoxy groups optionally substituted with one or more halogen atoms;

Z is CF₃; and

B is hydrogen or $C_1-C_6$ alkyl substituted with one $C_1-C_4$ alkoxy group.

Exemplary of halogen hereinabove are fluorine, chlorine, bromine and iodine. The term "$C_1-C_6$ haloalkyl" is defined as a $C_1-C_6$ alkyl group substituted with one or more halogen atoms.

Advantageously, it has been found that the formula I fungicidal agents of the present invention are useful in the prevention, control or amelioration of diseases such as apple scab, grape downy mildew, wheat leaf rust and wheat powdery mildew. Such diseases are caused by the phytopathogenic fungi *Venturia inaequalis*, *Plasmopara viticola*, *Puccinia recondita* f. sp. tritici and *Erysiphe graminis* f. sp. tritici, respectively.

Thienyl- and furylpyrrole compounds of formula I wherein X is CN and Y, Z and B are hydrogen, may be prepapred by reacting an N-formyl(thienyl or furyl)glycine of formula II with 2-chloroacrylonitrile and acetic anhydride as shown in Flow Diagram I.

FLOW DIAGRAM I

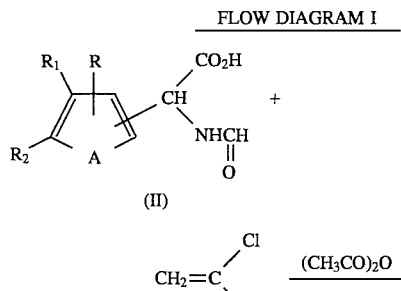

(II)

-continued
FLOW DIAGRAM I

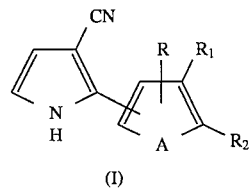

(I)

Certain compounds of formula I wherein X is CN, Y is $C_1-C_6$ haloalkyl and Z and B are hydrogen may be prepared by reacting the appropriately substituted thienyl- or furylglycine of formula III with a $C_1-C_6$ haloalkyl acid anhydride to form an oxazolinone intermediate of formula IV and reacting said formula IV intermediate with 2-chloroacrylonitrile as shown in Flow Diagram II.

FLOW DIAGRAM II

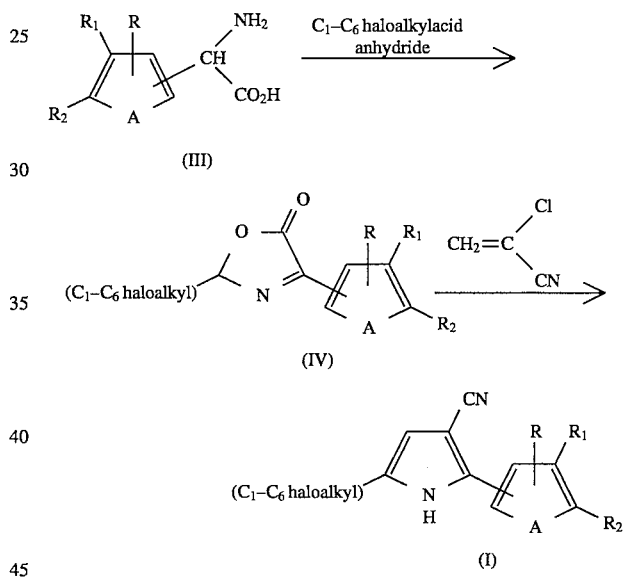

Formula I compounds wherein X and Y are $C_1-C_6$ haloalkyl and Z and B are hydrogen may be prepared by reacting an oxazolinone of formula IV with a bromoalkene of formula V as shown in Flow Diagram III.

FLOW DIAGRAM III

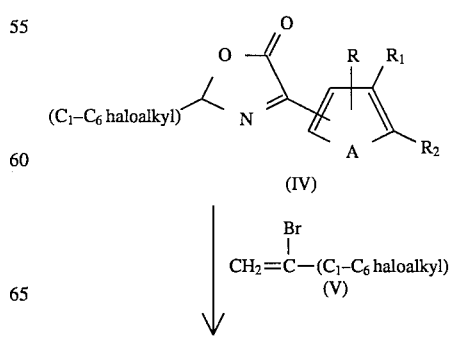

-continued
FLOW DIAGRAM III

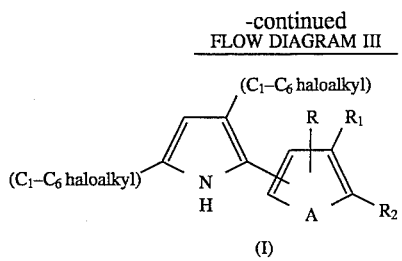

(I)

4-Cyano-2-(thienyl- or furyl)pyrrole compounds may be prepared by reacting acrylonitrile with an N-(trimethylsilyl-)methyl-5-methyl-(thienyl- or furyl)thioimidate of formula VI in the presence of tetrabutylammonium fluoride to form a 2-(thienyl- or furyl)-1-pyrroline-4-carbonitrile intermediate of formula VII and reacting said formula VII intermediate with 2,3-dichloro-5,6-dicyano-1,4-benzoquinone and pyridine as shown below in Flow Diagram IV.

FLOW DIAGRAM IV

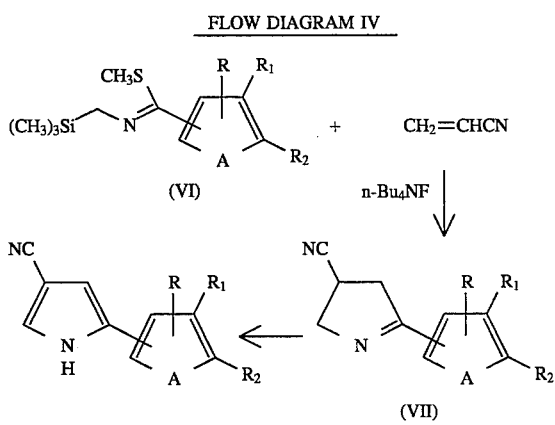

3-Cyano or nitro-2-thienylpyrrole compounds may be prepared as shown below in Flow Diagram V.

FLOW DIAGRAM V

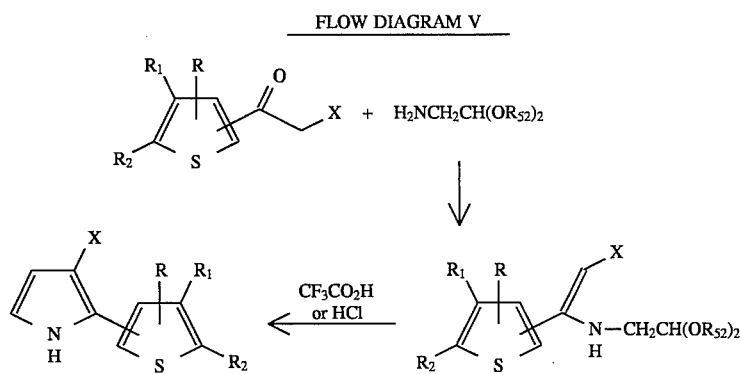

wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

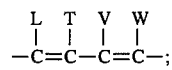

L, T, V and W are each independently hydrogen, halogen, CN or $NO_2$;

X is CN or $NO_2$; and $R_{52}$ is $C_1$–$C_4$ alkyl.

2-(Thienyl- or furyl)pyrrole-3,4-dicarbonitrile compounds may be prepared as shown below in Flow Diagram VI.

FLOW DIAGRAM VI

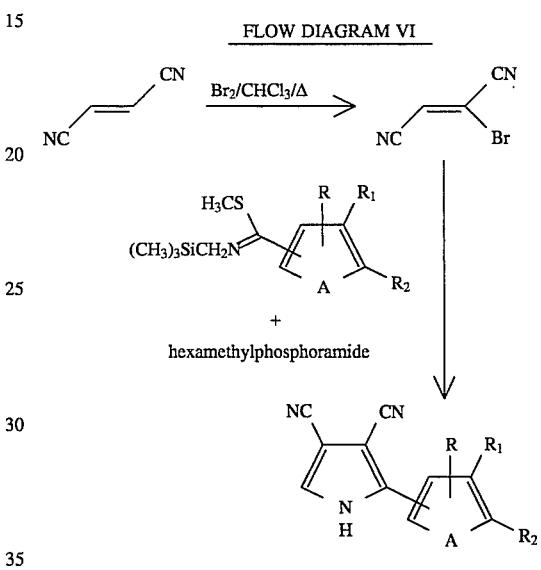

Formula I compounds wherein X is $C(S)NH_2$ may be prepared by reacting the appropriately substituted formula VIII (thienyl- or furyl)pyrrole-carbonitrile with an excess of hydrogen peroxide and sodium hydroxide to give the appropriately substituted formula IX (thienyl- or furyl)pyrrole carboxamide and reacting said formula IX carboxamide with a reagent capable of introducing the thioxo group, such as 2,4-bis(4-methoxyphenyl)-1,3-dithia-2,4-diphosphetane-2,4-disulfide as shown below in Flow Diagram VII.

FLOW DIAGRAM VII

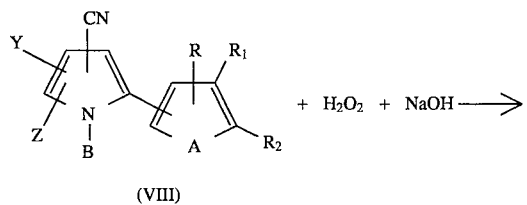

(VIII)

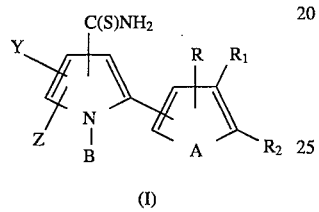

(IX)

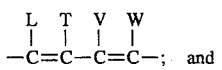

(I)

wherein

A, B, Y and Z are as described hereinabove for formula I;

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

$$\begin{array}{cccc} L & T & V & W \\ | & | & | & | \\ -C=C-C=C- \end{array} ; \text{ and}$$

L, T, V and W are each independently hydrogen, halogen, CN or $NO_2$.

4-(Thienyl- or furyl) pyrrole-3-thiocarboxamide compounds may be prepared by reacting the appropriately substituted formula X aldehyde with triethyl phosphonoacetate, lithium chloride and triethylamine to form the ester of formula XI. The formula XI ester is reacted with a strong base such as sodium hydride and tosylmethyl isocyanide to form a formula XII ethyl 4-(thienyl- or furyl) pyrrole-3-carboxylate which is hydrolyzed with an alkali metal hydroxide such as potassium hydroxide to form a formula XIII 4-(thienyl- or furyl)pyrrole-3-carboxylic acid. The formula XIII carboxylic acid is reacted with a tri($C_1$-$C_4$ alkyl)amine to form a first mixture. The first mixture is reacted with thionyl chloride and N,N-dimethylformamide to give a second mixture. The second mixture is reacted with a formula XIV amine compound to give the formula XV 4-(thienyl- or furyl)pyrrole-3-carboxamide and reacting the formula XV carboxamide with a reagent capable of introducing the thioxo group, such as 2,4-bis(4-methoxyphenyl)-1,3-dithia-2,4-diphosphetane- 2,4-disulfide, to give the desired 4-(thienyl- or furyl)pyrrole-3-thiocarboxamide. The above reaction schemes are shown below in Flow Diagram VIII.

FLOW DIAGRAM VIII

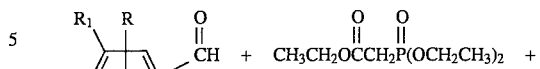

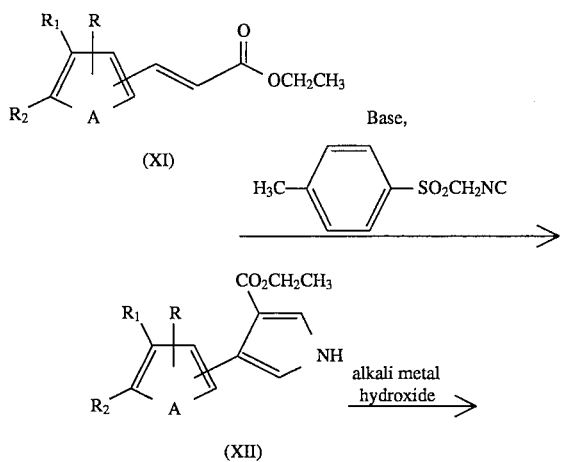

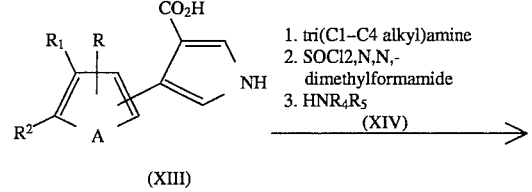

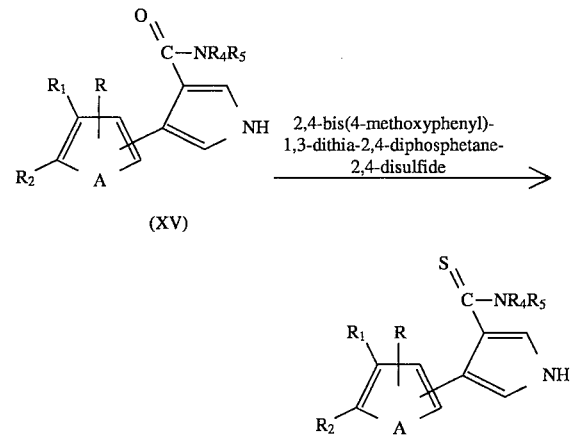

wherein

A, $R_4$ and $R_5$ are as described hereinabove for formula I;

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

$$\begin{array}{cccc} \text{L} & \text{T} & \text{V} & \text{W} \\ | & | & | & | \\ -\text{C}=\text{C}-\text{C}=\text{C}- \end{array};$$

L, T, V and W are each independently hydrogen, halogen, CN or $NO_2$.

2-(Thienyl- and furyl)-1-hydroxypyrrole-3-carbonitrile compounds may be prepared by reacting a formula XVI ester with an acetal of cyanopropionaldehyde in the presence of sodium hydride to form an acetal of formula XVII and reacting the formula XVII acetal with hydroxylamine hydrochloride as shown in Flow Diagram IX.

5-(Thienylpyrrole-2,3-dicarbonitrile compounds of formula I may be prepared by reacting a formula XVIII oxime with sodium oxalacetate to form a formula XIX intermediate which is reacted with hydrochloric acid in the presence of an alcohol to form a formula XX 5-thienyl-1-hydroxypyrrole-3-carboxylate. The formula XX carboxylate is reacted with methyl iodide and potassium t-butoxide to give a formula XXI 5-thienyl-1-methoxypyrrole-3-carboxylate. Saponification of the formula XXI carboxylate gives a formula XXII 5-thienyl-1-methoxypyrrole-3-carboxylic acid which is reacted with chlorosulfonyl isocyanate and N,N-dimethylformamide to give the formula I 5-thienylpyrrole-2,3-dicarbonitrile. The above reaction scheme is shown in Flow Diagram X.

FLOW DIAGRAM IX

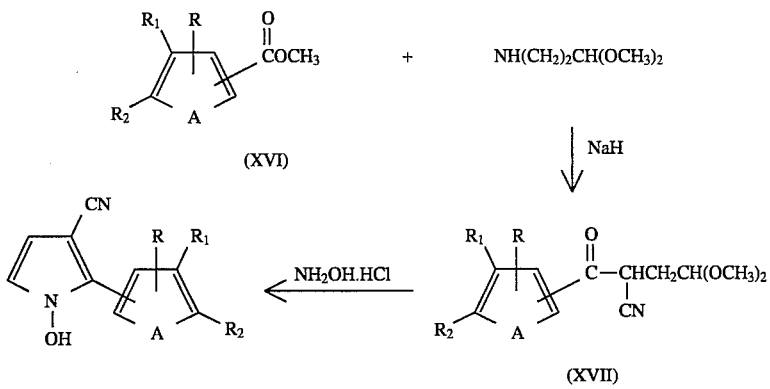

wherein

A is O or S;

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

$$\begin{array}{cccc} \text{L} & \text{T} & \text{V} & \text{W} \\ | & | & | & | \\ -\text{C}=\text{C}-\text{C}=\text{C}- \end{array};$$

L, T, V and W are each independently hydrogen, halogen, CN or $NO_2$.

FLOW DIAGRAM X

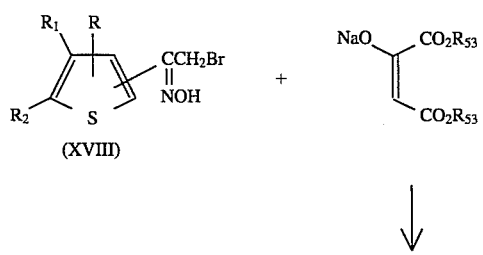

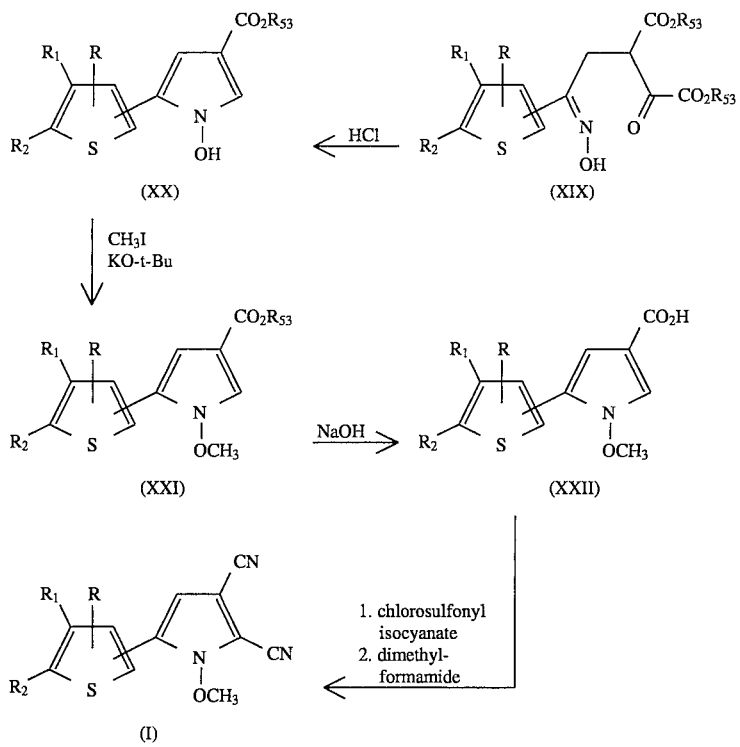

wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

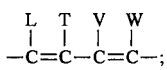

L, T, V and W are each independently hydrogen, halogen, CN or $NO_2$; and $R_{53}$ is $C_1$–$C_6$ alkyl or $C_3$–$C_6$ cycloalkyl.

2,4-Dibromo-5-(2-thienyl)-1-methoxypyrrole-3-carbonitrile compounds of the present invention may 15 be prepared by reacting a formula XXIII 5-(2-thienyl)-1-methoxypyrrole-3-carboxylate with bromine to form a formula XXIV 2,4-dibromo-5-(2-thienyl)-1-methoxypyrrole-3-carboxylate. Saponification of the formula XXIV carboxylate gives a formula XXV acid which is reacted with chlorosulfonyl isocyanate and dimethylformamide to give the desired 2,4-dibromo-5-(2-thienyl)-1-methoxypyrrole-3-carbonitrile. The above reaction scheme is shown in Flow Diagram XI.

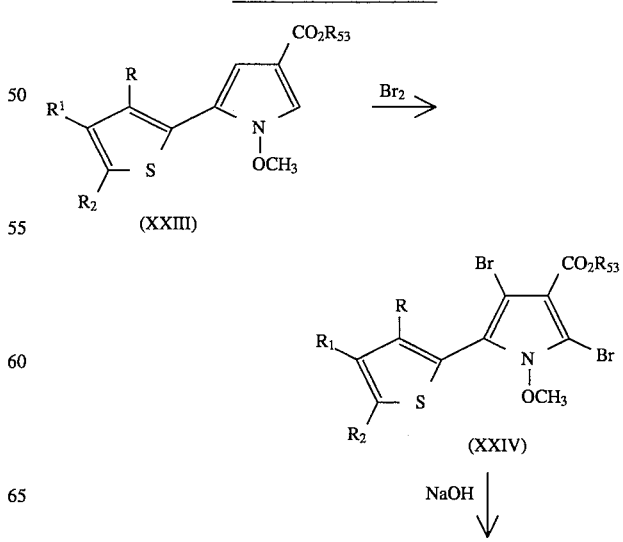

-continued
FLOW DIAGRAM XI

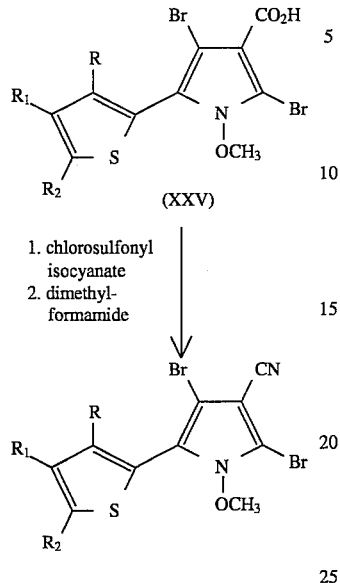

wherein

R and $R_1$ are each independently hydrogen, halogen or $NO_2$, and when $R_1$ is taken together with $R_2$ and the carbon atoms to which they are attached, they may form a ring in which $R_1R_2$ is represented by the structure:

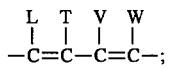

$R_2$ is halogen, and when taken together with $R_1$ and the carbon atoms to which they are attached, they may form a ring in which $R_1R_2$ is represented by the structure:

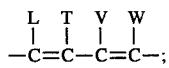

L, T, V and W are each independently hydrogen, halogen, CN or $NO_2$; and $R_{53}$ is $C_1$–$C_6$ alkyl or $C_3$–$C_6$ cycloalkyl.

Similarly, 2,4-dibromo-5-(3-thienyl)-1-methoxypyrrole-3-carbonitrile compounds may be prepared as shown in Flow Diagram XII.

FLOW DIAGRAM XII

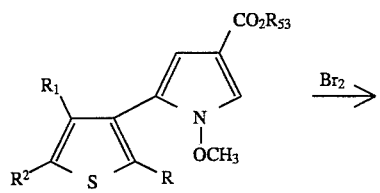

-continued
FLOW DIAGRAM XII

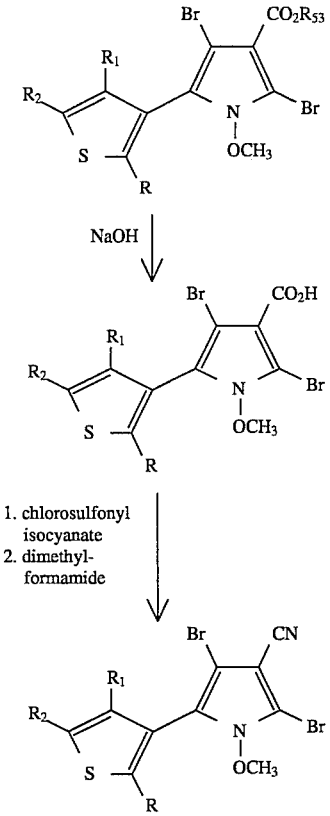

wherein $R_1$ is hydrogen, halogen or $NO_2$, and when $R_1$ is taken together with $R_2$ and the carbon atoms to which they are attached, they may form a ring in which $R_1R_2$ is represented by the structure:

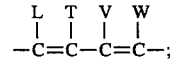

R and $R_2$ are each independently halogen, and when $R_2$ is taken together with $R_1$ and the carbon atoms to which they are attached, they may form a ring in which $R_1R_2$ is represented by the structure:

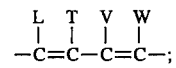

L, T, V and W are each independently hydrogen, halogen, CN or $NO_2$; and $R_{53}$ is $C_1$–$C_6$ alkyl or $C_3$–$C_6$ cycloalkyl. 4-Bromo-2-($C_1$–$C_6$ haloalkyl)-5-(2-thienyl)-1-methoxypyrrole-3-carbonitrile compounds of the present invention may be prepared as shown in Flow Diagram XIII.

FLOW DIAGRAM XIII
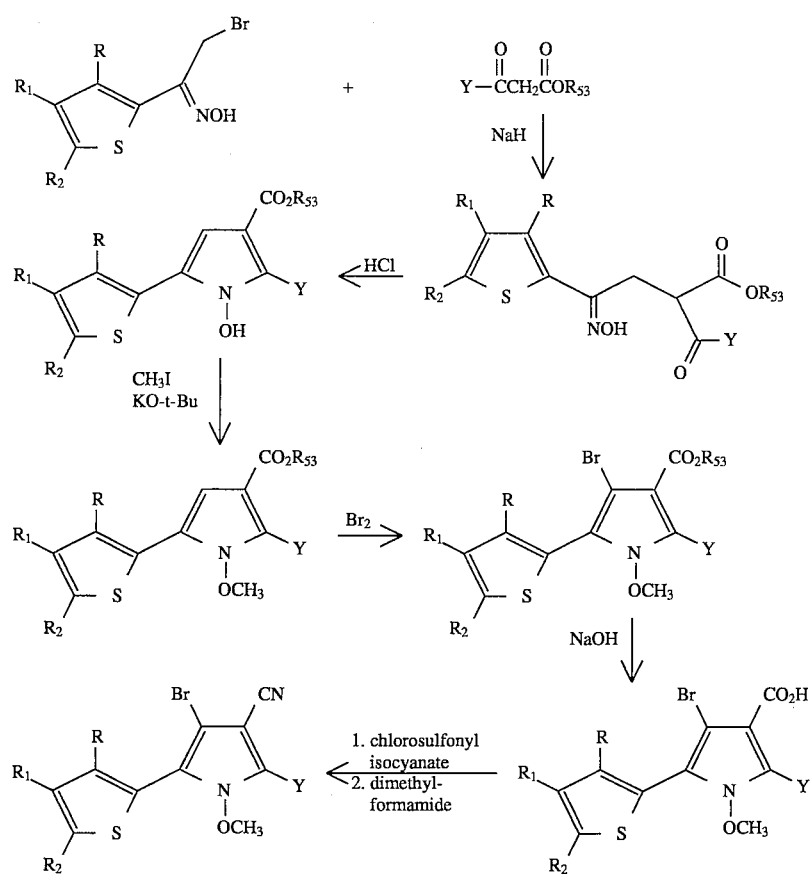
wherein Y is $C_1$–$C_6$ haloalkyl and R, $R_1$, $R_2$ and $R_{53}$ are as described in Flow Diagram XI.
Similarly, 4-bromo-2-($C_1$–$C_6$ haloalkyl)-5-(3-thienyl)-1-methoxypyrrole-3-carbonitrile compounds may be prepared as shown in Flow Diagram XIV.
FLOW DIAGRAM XIV
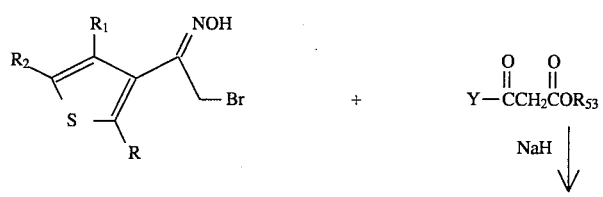

-continued
FLOW DIAGRAM XIV

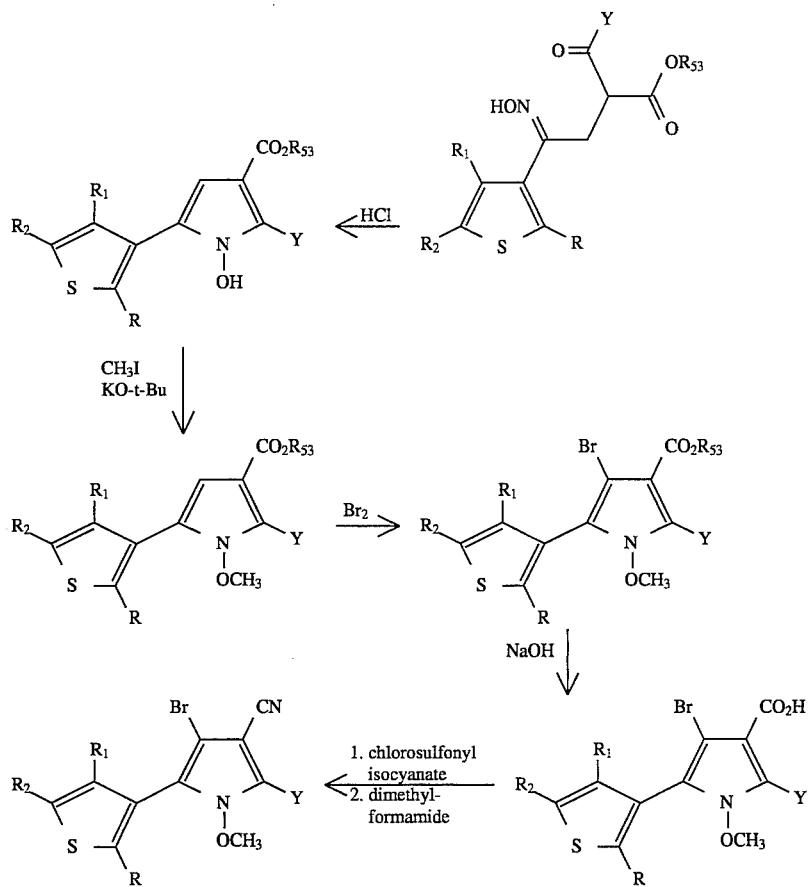

wherein Y is $C_1$–$C_6$ haloalkyl and R, $R_1$, $R_2$ and $R_{53}$ are as described in Flow Diagram XII.

3,4-Dibromo-5-(2-thienyl)-1-methoxypyrrole-2-carbonitrile compounds may be prepared by reacting a 5-(2-thienyl)-1-methoxypyrrole-3-carboxylate with chlorosulfonyl isocyanate and dimethylformamide to give a 2-cyano-5-(2-thienyl)-1-methoxypyrrole-3-carboxylate. Saponification and bromination of the 2-cyano-5-(2-thienyl)-1-methoxypyrrole-3-carboxylate compound gives the desired 3,4-dibromo-5-(2-thienyl)-1-methoxypyrrole-2-carbonitrile as shown in Flow Diagram XV.

FLOW DIAGRAM XV

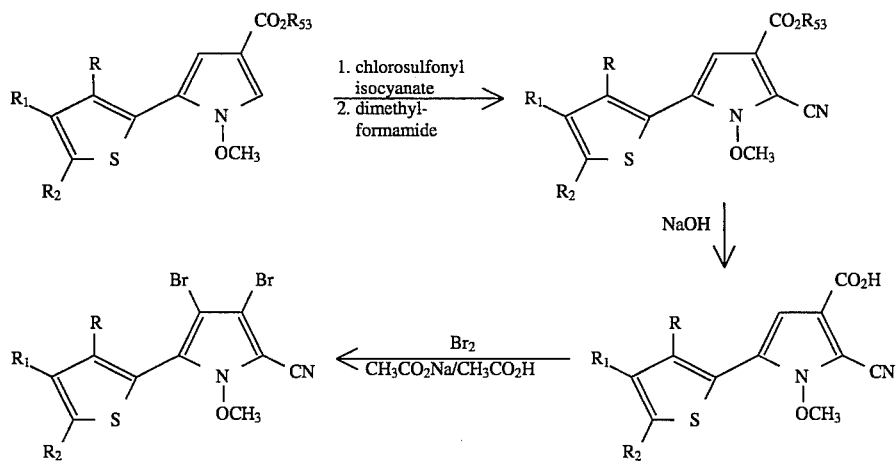

wherein R, $R_1$, $R_2$ and $R_{53}$ are as described in Flow Diagram XI.
Similarly, 3,4-dibromo-5-(3-thienyl)-1-methoxypyrrole-2-carbonitrile compounds may be prepared as shown in Flow Diagram XVI.
Formula I 2-bromo-3-nitro-5-($C_1$–$C_6$ haloalkyl)-4-(2-thienyl)-1-methoxypyrrole compounds may be prepared as shown in Flow Diagram XVII.
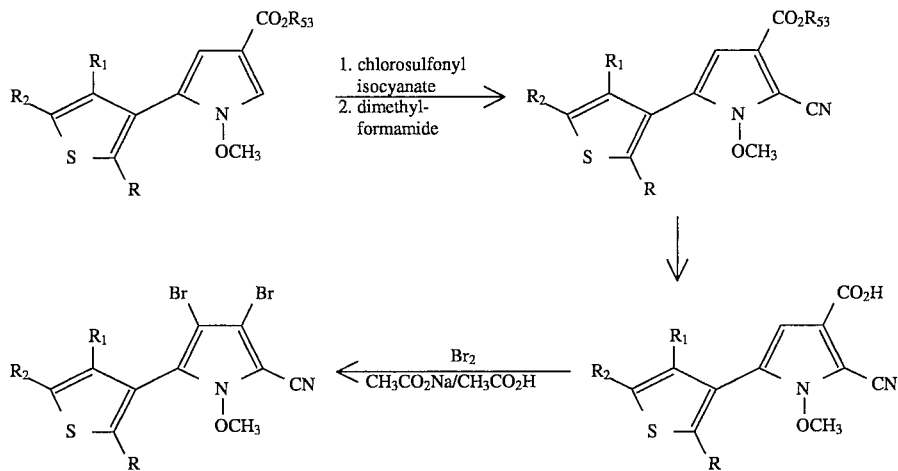
wherein R, $R_1$, $R_2$ and $R_{53}$ are as described in Flow Diagram XII.
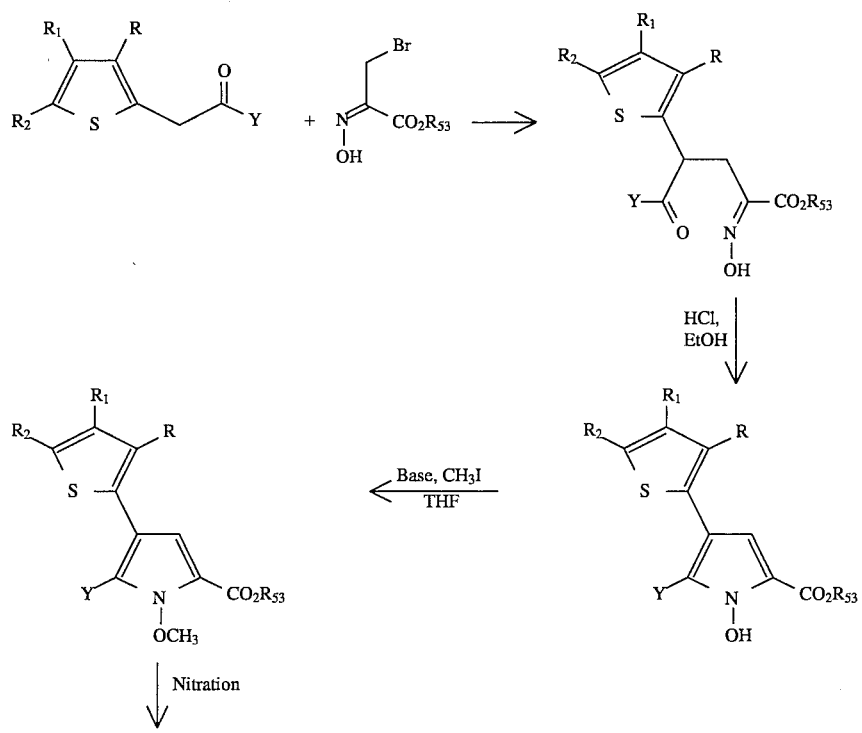

-continued
FLOW DIAGRAM XVII
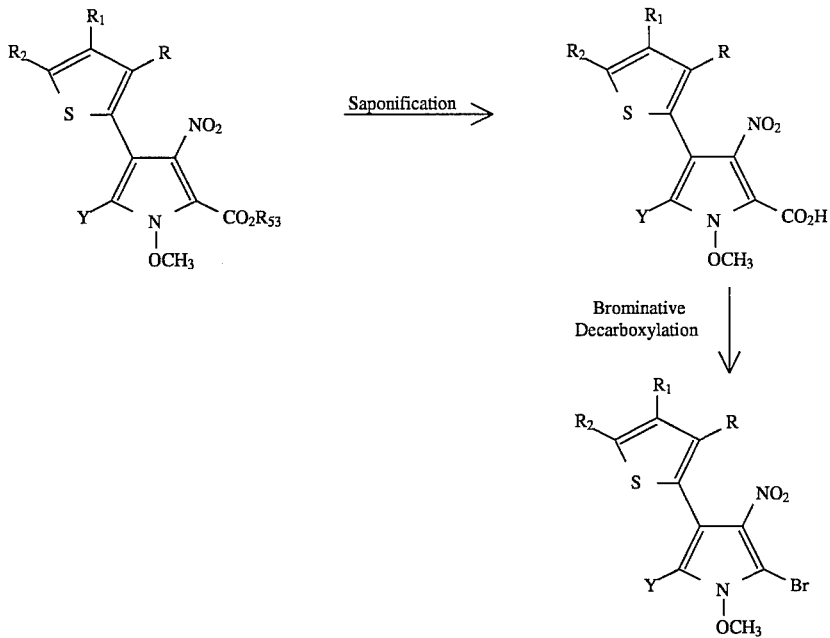
wherein Y is $C_1$–$C_6$ haloalkyl and R, $R_1$, $R_2$ and $R_{53}$ are as described in Flow Diagram XI.
Similarly, 2-bromo-3-nitro-5- ($C_1$–$C_6$ haloalkyl)-4-(3-thienyl)-1-methoxypyrrole compounds may be prepared as shown in Flow Diagram XVIII.
FLOW DIAGRAM XVIII
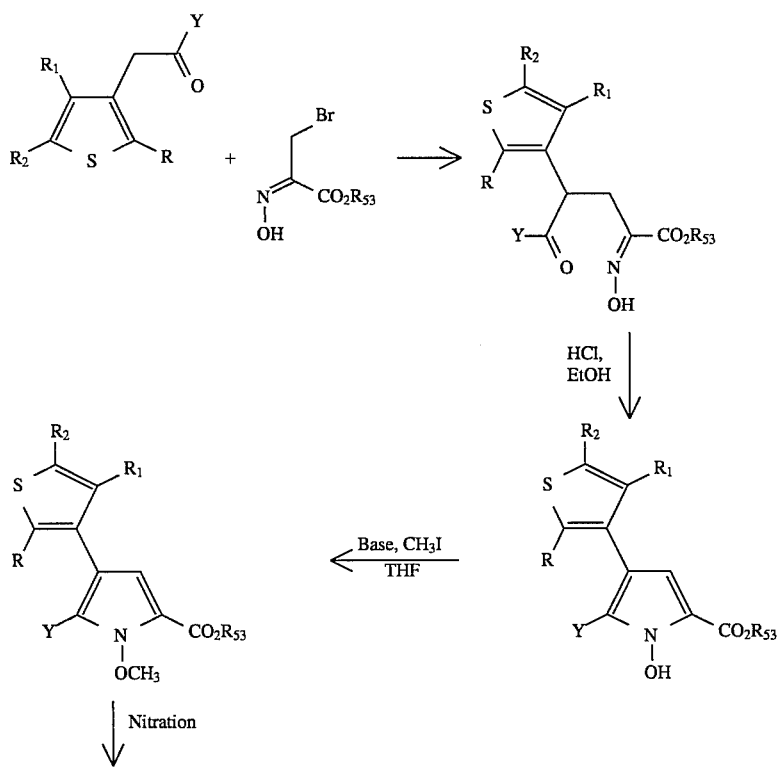

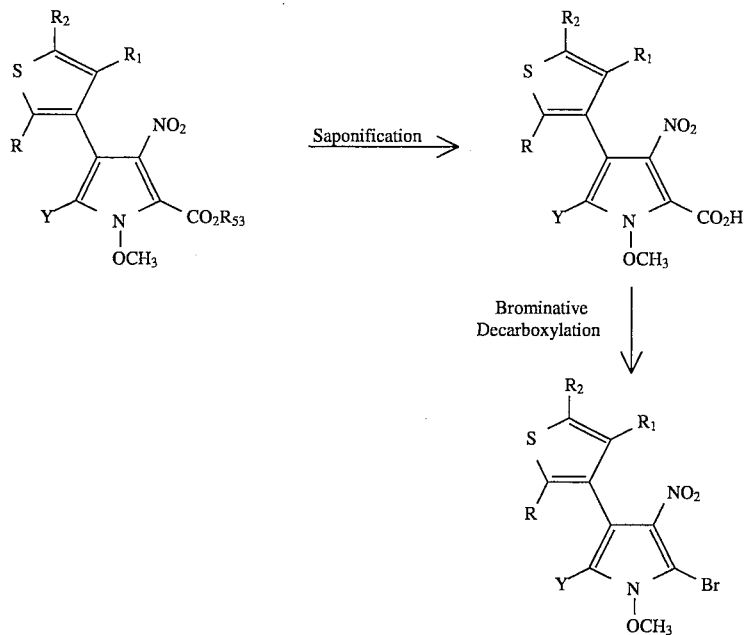
wherein Y is $C_1$–$C_6$ haloalkyl and R, $R_1$, $R_2$ and $R_{53}$ are as described in Flow Diagram XII.
3-Bromo-5-($C_1$–$C_6$ haloalkyl)-4-(2-thienyl)-1-methoxy-pyrrole-2-carbonitrile compounds may be prepared as shown in Flow Diagram XIX.
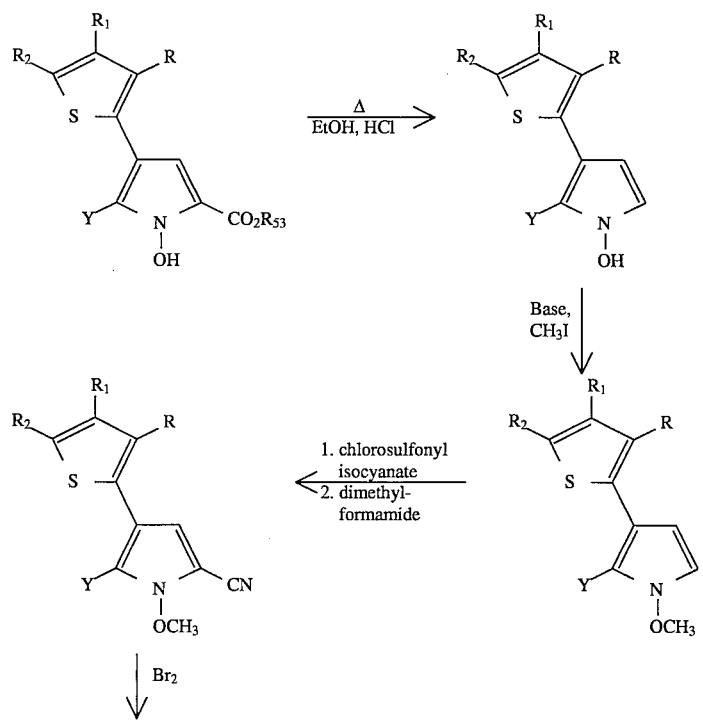

-continued
FLOW DIAGRAM XIX

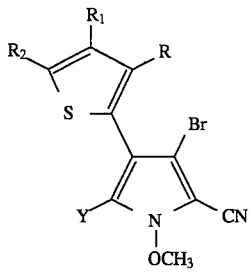

wherein Y is $C_1$–$C_6$ haloalkyl and R, $R_1$, $R_2$ and $R_{53}$ are as described in Flow Diagram XI.

Similarly, 3-bromo-5-($C_1$–$C_6$ haloalkyl)-4-(3-thienyl)-1-methoxypyrrole-2-carbonitrile compounds may be prepared as shown in Flow Diagram XX.

FLOW DIAGRAM XX

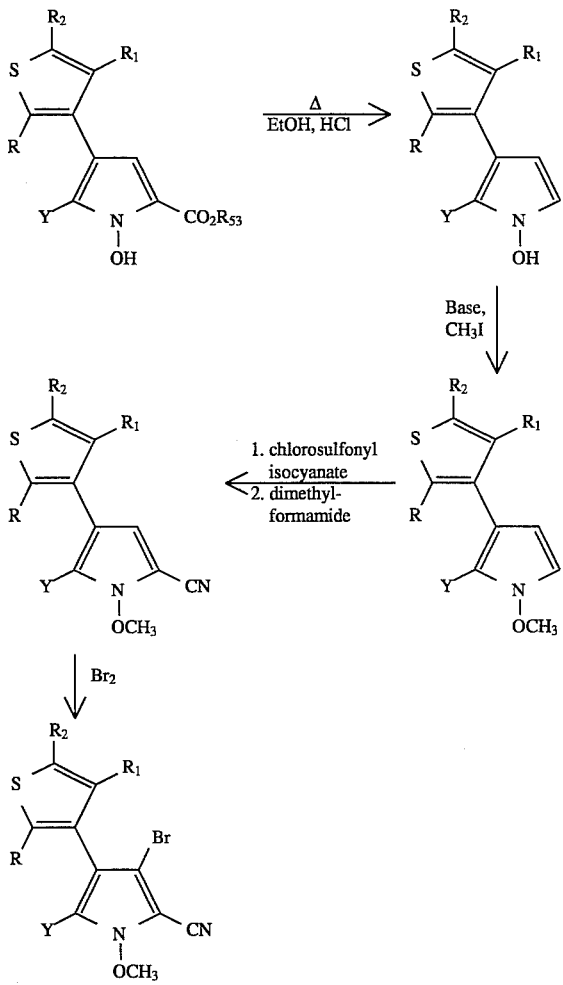

wherein Y is $C_1$–$C_6$ haloalkyl and R, $R_1$, $R_2$ and $R_{53}$ are as described in Flow Diagram XII.

4-Aryl-3-(nitro and cyano)-5-($C_1$–$C_6$ haloalkyl)-2-(2- and 3-thienyl and -furyl)pyrrole compounds may be prepared by reacting a substituted or unsubstituted beta-(nitro or cyano)styrene of formula XXVI with bromine to form a (substituted or unsubstituted-phenyl)-1,2-dibromo-2-(nitro or cyano)ethane of formula XXVII which is then subjected to a dehalogenation treatment using a base such as pyridine to form a substituted or unsubstituted (nitro or cyano)bromostyrene of formula XXVIII. Reaction of the bromostyrene with a formula XXIX oxazolinone in the presence of a tri($C_1$–$C_4$ alkyl)amine gives the desired 4-aryl-3-(nitro or cyano)-5-($C_1$–$C_6$ haloalkyl)-2-(2- or 3-thienyl or -furyl)pyrrole. The above reaction scheme is shown in Flow Diagram XXI.

FLOW DIAGRAM XXI

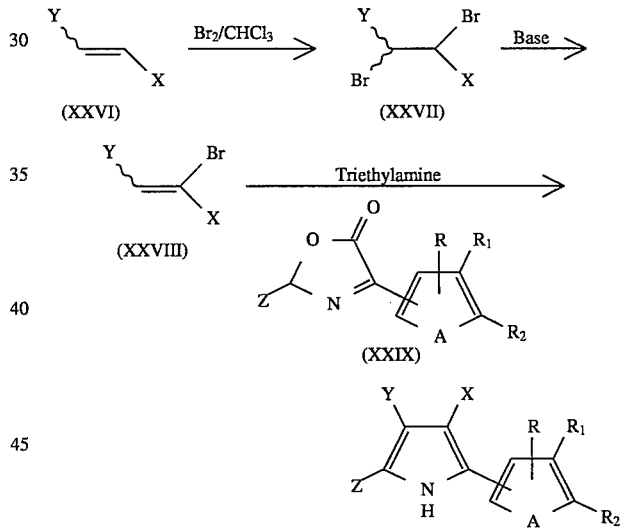

wherein
X is CN or $NO_2$;
Y is phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;
Z is $C_1$–$C_6$ haloalkyl;
A is O or S;
R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

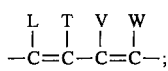

L, T, V and W are each independently hydrogen, halogen, CN or NO₂.

Similarly, 4-(2-thienyl and -furyl)-3-(nitro and cyano)-5-(C₁–C₆ haloalkyl)-2-arylpyrrole compounds may be prepared as shown in Flow Diagram XXII and 4-(3-thienyl and -furyl)-3-(nitro and cyano)-5-(C₁–C₆ haloalkyl)-2-arylpyrrole compounds may be prepared as shown in Flow Diagram XXIII.

FLOW DIAGRAM XXII

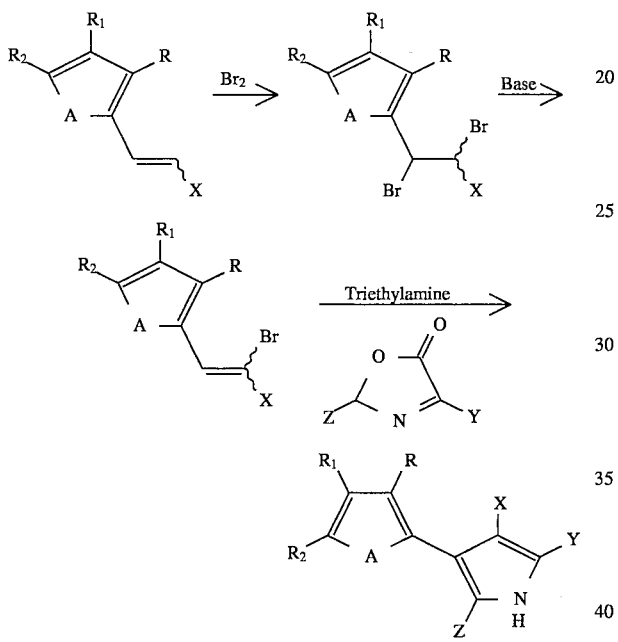

wherein A, X, Y and Z are as described in Flow Diagram XXI and R, R₁ and R₂ are as described in Flow Diagram XI.

FLOW DIAGRAM XXIII

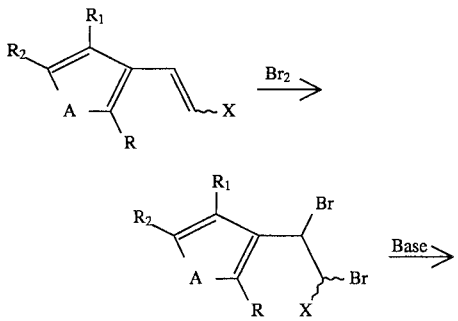

-continued
FLOW DIAGRAM XXIII

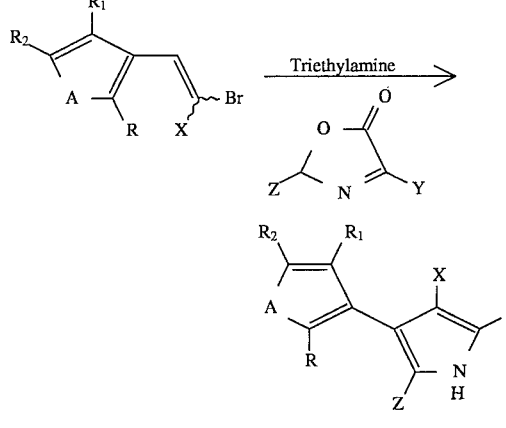

wherein A, X, Y and Z are as described in Flow Diagram XXI and R, R₁ and R₂ are as described in Flow Diagram XII.

3-Aryl-2-(C₁–C₆ haloalkyl)-5-(2- and 3-thienyl and -furyl)pyrrole compounds may be prepared as shown in Flow Diagram XXIV.

FLOW DIAGRAM XXIV

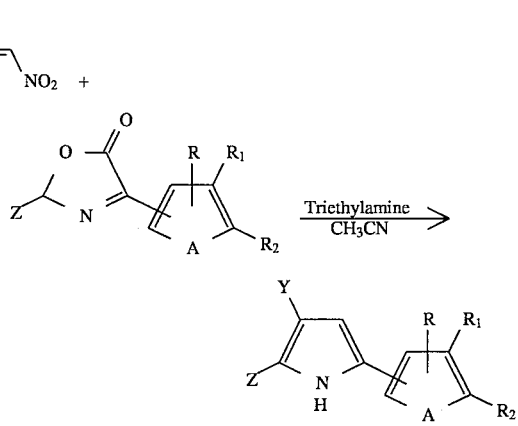

wherein Y, Z, A, R, R₁ and R₂ are as described in Flow Diagram XXI.

Similarly, 3-(2- and 3-thienyl and -furyl)-2-(C₁–C₆ haloalkyl)-5-arylpyrrole compounds may be prepared as shown in Flow Diagram XXV.

FLOW DIAGRAM XXV

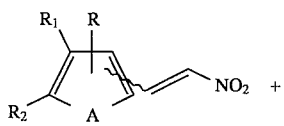

-continued
FLOW DIAGRAM XXV

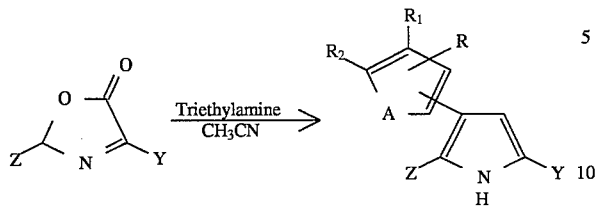

wherein Y, Z, A, R, $R_1$ and $R_2$ are as described in Flow Diagram XXI.

5-($C_1$–$C_6$ Haloalkyl)-3-aryl-2-(2- and 3-thienyl and -furyl)pyrrole compounds may be prepared by reacting a substituted or unsubstituted acetophenone of formula XXX with a thionyl halide in the presence of an organic base such as pyridine. Thereafter, the reaction mixture is treated with aqueous sodium tetrafluoroborate to give a formula XXXI N-α-(substituted or unsubstituted)styrylpyridinium tetrafluoroborate. The formula XXXI styrylpyridinium tetrafluoroborate is then reacted with a formula XXIX oxazolinone in the presence of a base, such as pyridine to form the desired 5-($C_1$–$C_6$ haloalkyl)-3-aryl-2-(2- or 3-thienyl or -furyl)pyrrole compound. The above reaction scheme is shown in Flow Diagram XXVI.

FLOW DIAGRAM XXVI

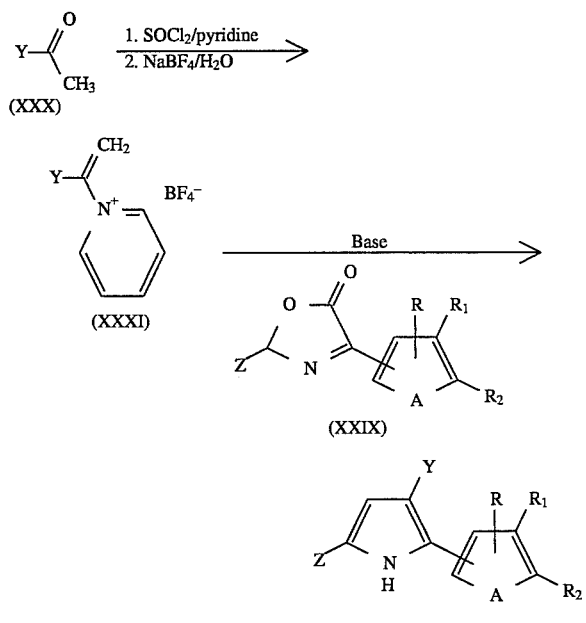

wherein Y, Z, A, R, $R_1$ and $R_2$ are as described in Flow Diagram XXI.

Similarly, 5-($C_1$–$C_6$ haloalkyl)-2-aryl-3-(2-thienyl and -furyl)pyrrole compounds may be prepared as shown in Flow Diagram XXVII and 5-($C_1$–$C_6$ haloalkyl)-2-aryl-3-(3-thienyl and -furyl)pyrrole compounds may be prepared as shown in Flow Diagram XXVIII.

FLOW DIAGRAM XXVII

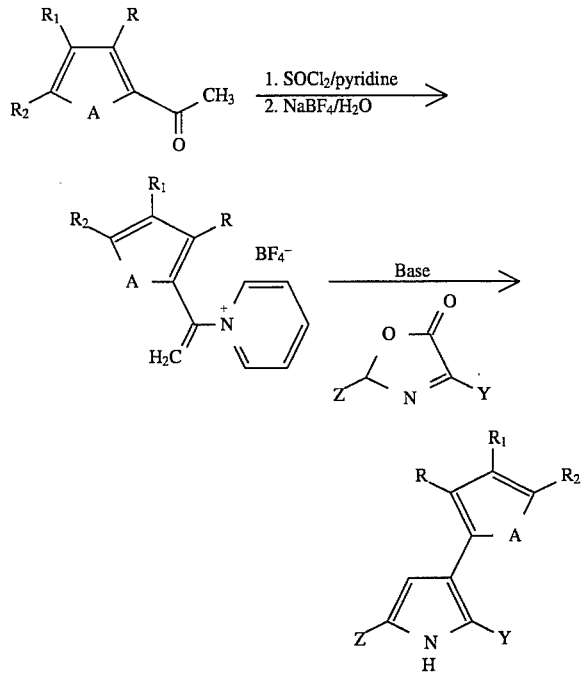

wherein A, Z and Y are as described in Flow Diagram XXI and R, $R_1$ and $R_2$ are as described in Flow Diagram XI.

FLOW DIAGRAM XXVIII

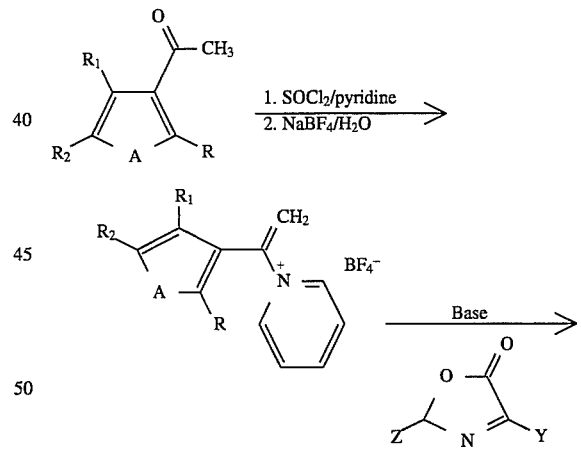

-continued
FLOW DIAGRAM XXVIII

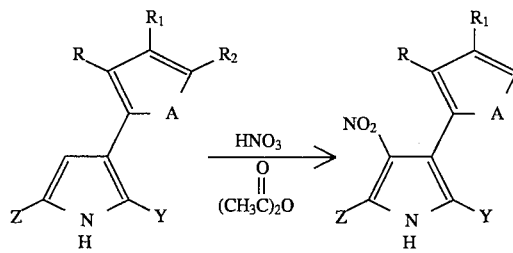

wherein A, Z and Y are as described in Flow Diagram XXI and $R$, $R_1$ and $R_2$ are as described in Flow Diagram XII.

5-($C_1$-$C_6$ haloalkyl)-2-aryl-4-nitro-3-(2-thienyl)pyrrole compounds may be prepared by reacting a 5-($C_1$-$C_6$ haloalkyl)-2-aryl-3-(2-thienyl)pyrrole compound with nitric acid and acetic anhydride as shown in Flow Diagram XXIX.

FLOW DIAGRAM XXIX wherein A, Z and Y are as described in Flow Diagram XXI and $R$, $R_1$ and $R_2$ are as described in Flow Diagram XI.

Similarly, 5-($C_1$-$C_6$ haloalkyl)-2-aryl-4-nitro-3-(3-thienyl)pyrrole compounds may be prepared as shown in Flow Diagram XXX.

FLOW DIAGRAM XXX

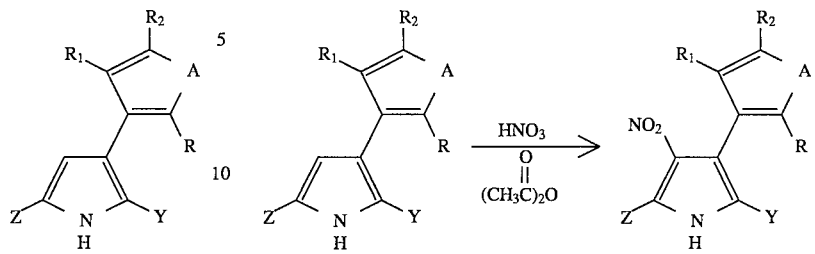

wherein A, Z and Y are as described in Flow Diagram XXI and $R$, $R_1$ and $R_2$ are as described in Flow Diagram XII.

2,3,5-Tris(trifluoromethyl)-4-(2- and 3-thienyl)pyrrole compounds of the present invention may be prepared by reacting a formula XXX 3-(2- or 3-thienyl-1,1,1-trifluoro-2-propanone with hydroxylamine hydrochloride to form a formula XXXI oxime. The formula XXXI oxime is then reacted in a pressure bottle with liquid hexafluoro-2-butyne in the presence of at least a ten mole percent amount of a base such as an alkali metal alkoxide in a solvent at an elevated temperature to form a formula XXXII 3-(2- or 3-thienyl)-5a-hydroxy-2,4-a,5b-tris(trifluoromethyl)-1-pyrroline. The formula XXXII pyrroline is then reacted with hydrochloric acid in an alcohol to form the desired 2,3,5-tris(trifluoromethyl)-4-(2- or 3-thienyl)pyrrole compound. The above reaction scheme is shown in Flow Diagram XXXI.

FLOW DIAGRAM XXXI

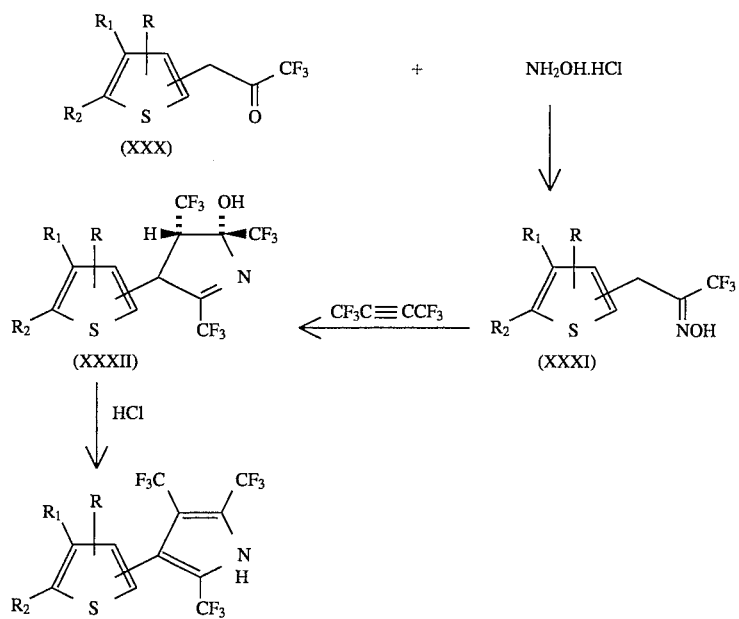

3,4-Bis(trifluoromethyl)-2-(2- and 3-thienyl and -furyl)pyrrole compounds may be prepared by reacting an N-(trimethylsilyl)methyl-5-methyl(thienyl- or furyl)thioimidate of formula VI with 2,3-dichlorohexafluorobutene as shown below in Flow Diagram XXXII.

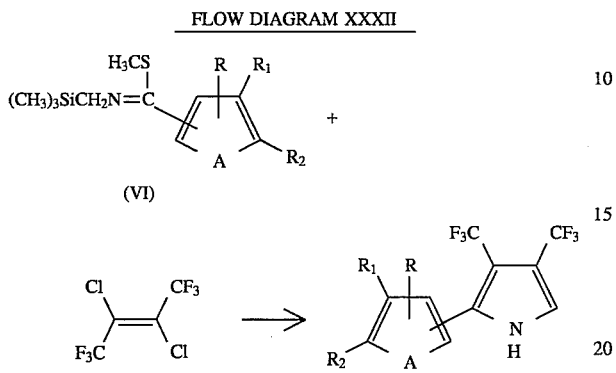

FLOW DIAGRAM XXXII 2,3-Bis(trifluoromethyl)-4-halo-5-(2-thienyl)pyrrole compounds may be prepared by reacting an oxime of formula XXXIII with hexafluoro-2-butyne in the presence of a base such as an alkali metal alkoxide to form the vinyl oxime of formula XXXIV and the 2-(2-thienyl)-4,5-trans-bis(trifluoromethyl)-1-pyrrolin-5-ol of formula XXXV. The formula XXXIV vinyl oxime is then heated to form the formula XXXVI 2-(2-thienyl-4,5-bis(trifluoromethyl)-1-pyrrolin-4-ol. The formula XXXV pyrrolin-5-ol or formula XXXVI pyrrolin-4-ol is then reacted with hydrochloric acid in an alcohol to obtain a 5-(2-thienyl)-2,3-bis(trifluoromethyl)pyrrole compound. The 5-(2-thienyl)-2,3-bis(trifluoromethyl)pyrrole is then reacted with a halogenating agent to obtain the desired 2,3-bis(trifluoromethyl)-4-halo-5-(2-thienyl)pyrrole. The above reaction scheme is shown in Flow Diagram XXXIII.

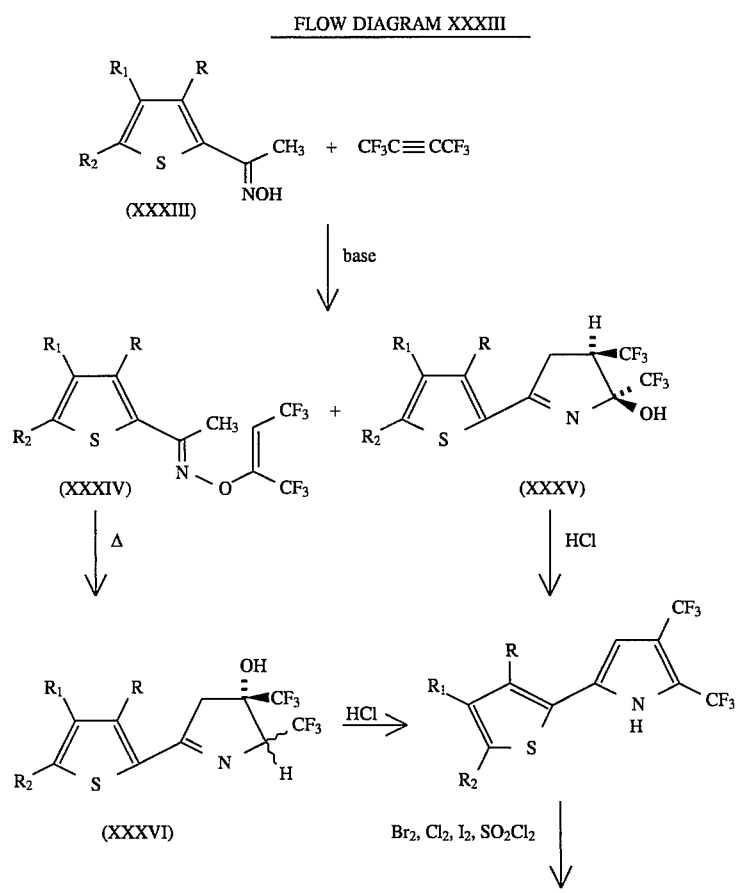

FLOW DIAGRAM XXXIII

-continued
FLOW DIAGRAM XXXIII

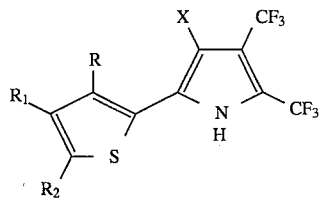

wherein X is Cl, Br or I and R, $R_1$ and $R_2$ are as described in Flow Diagram XI.

Similarly, 2,3-Bis(trifluoromethyl)-4-halo-5-(3-thienyl)pyrrole compounds may be prepared as shown in Flow Diagram XXXIV.

in Flow Diagram XII.

2,5-Bis(trifluoromethyl)-3-(2- and 3thienyl)pyrrole compounds may be prepared as shown in Flow Diagram XXXV.

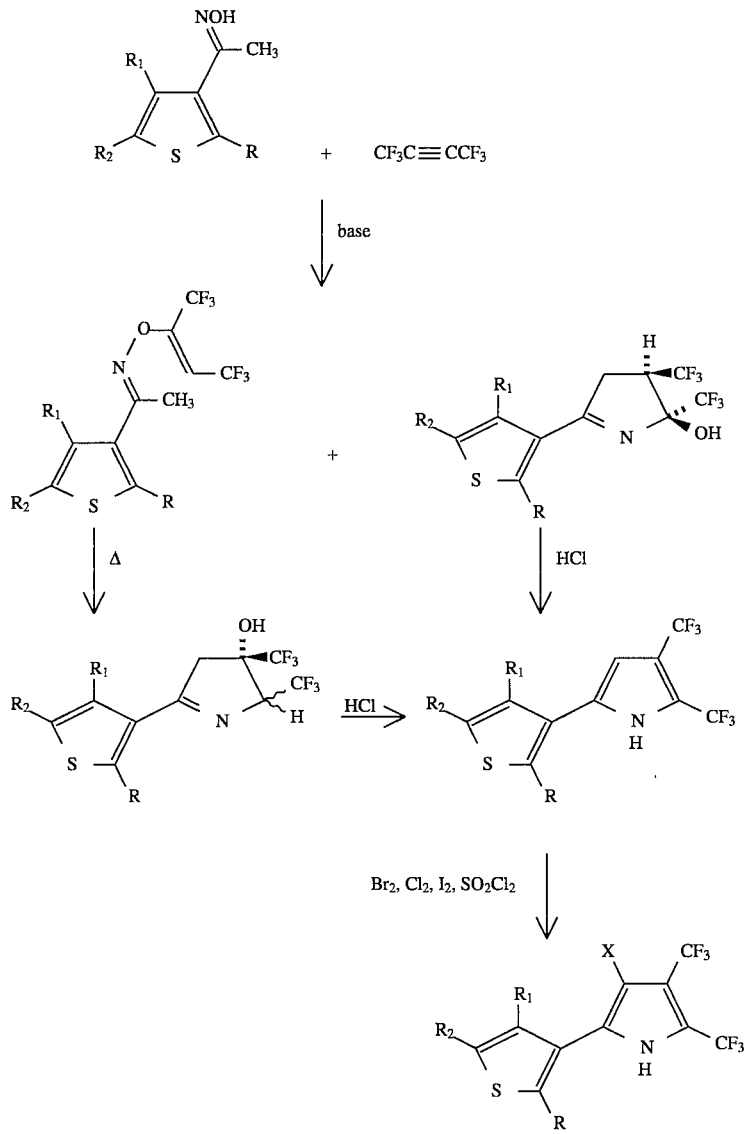

wherein X is Cl, Br or I and R, $R_1$ and $R_2$ are as described

FLOW DIAGRAM XXXV

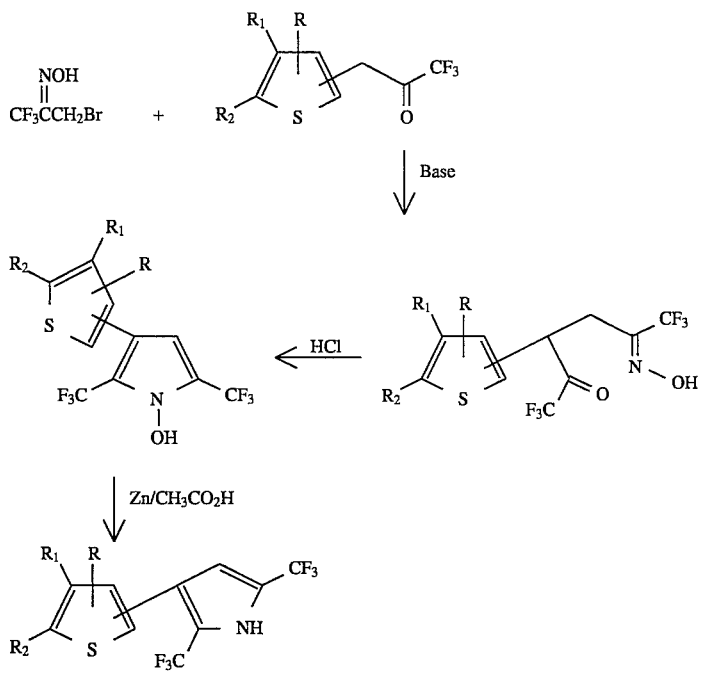

3-(Haloalkylsulfonyl)-2-(2- and 3-thienyl)pyrrole compounds may be prepared by reacting a (2- or 3-thienyl)ethynyl haloalkylsulfonyl compound of formula XXXVII with an aminoacetaldehyde di($C_1$–$C_4$ alkyl)acetal to form a {{α-[(haloalkylsulfonyl)methylene](2- or 3-thienyl)}amino}acetaldehyde di($C_1$–$C_4$ alkyl)acetal of formula XXXVIII. The formula XXXVIII acetal is then reacted with excess trifluoroacetic acid to obtain the desired 3-(haloalkylsulfonyl)-2-(2- or 3-thienyl)pyrrole compound.

The above reaction scheme is shown in Flow Diagram XXXVI.

FLOW DIAGRAM XXXVI

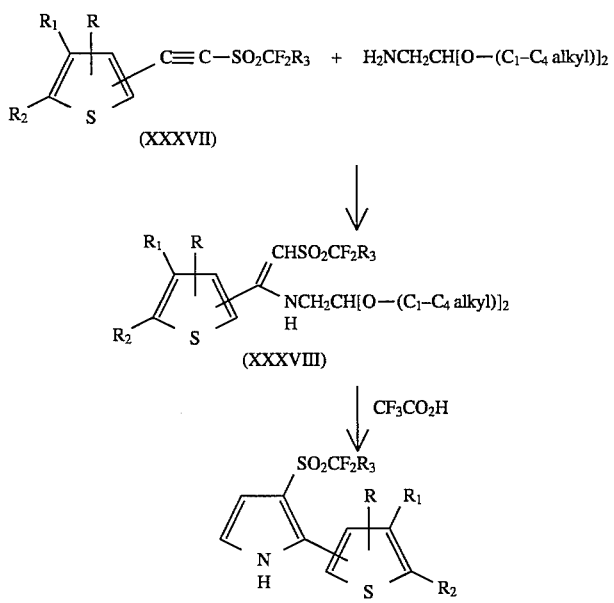

5-(Haloalkylthio)-2-(2- and 3-thienyl and -furyl)pyrrole compounds may be prepared by reacting a 2-(2- or 3-thienyl or -furyl)pyrrole compound with a haloalkylsulfenyl chloride compound in the presence of a base as shown in Flow Diagram XXXVII.

FLOW DIAGRAM XXXVII

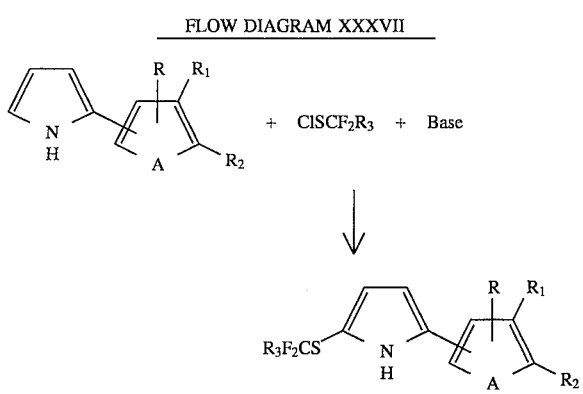

4-(Haloalkylsulfonyl)-5-(2-thenyl)pyrrole-2-carbonitrile compounds may be prepared by reacting a 3-(haloalkylsulfonyl)-2-(2-thienyl)pyrrole compound of formula XXXIX with chlorosulfonyl isocyanate in the presence of a solvent to form a reaction mixture. The reaction mixture is then treated with dimethylformamide to obtain the desired 4-(haloalkylsulfonyl)-5-(2-thienyl)pyrrole-2-carbonitrile compound. The above reaction scheme is shown in Flow Diagram XXXVIII.

FLOW DIAGRAM XXXVIII

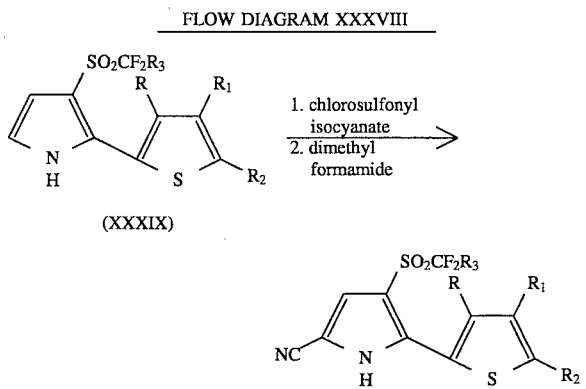

wherein $R_3$ is as described above for formula I and R, $R_1$ and $R_2$ areas described in Flow Diagram XI.

Similarly, 4-(haloalkylsulfonyl)-5-(3-thienyl)pyrrole-2-carbonitrile compounds may be prepared as shown in Flow Diagram XXXIX.

FLOW DIAGRAM XXXIX

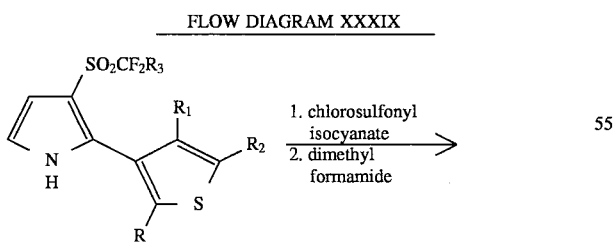

-continued
FLOW DIAGRAM XXXIX

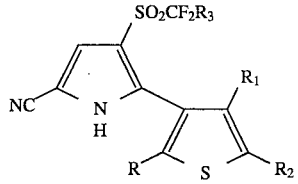

wherein $R_3$ is as described above for formula I and R, $R_1$ and $R_2$ are as described in Flow Diagram XII.

5-(Haloalkylsulfinyl)-2-(2- and 3-thienyl and -furyl)pyrrole compounds may be prepared by reacting a 5-(haloalkylthio)-2-(2- or 3-thienyl or -furyl)pyrrole compound with an oxidizing agent such as 3-chloroperoxybenzoic acid as shown in Flow Diagram XL.

FLOW DIAGRAM XL

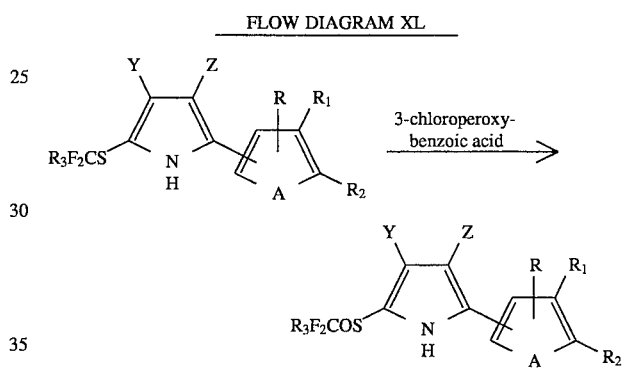

wherein A and $R_3$ are as described above for formula I; R, $R_1$ and $R_2$ are as described in Flow Diagram V and Y and Z are each independently hydrogen or halogen.

3-(2-And 3-thienyl and -furyl)-4-(haloalkylsulfonyl)pyrrole compounds may be prepared by reacting a haloalkylsulfone of formula XL with N-methylene-1-(p-tolylsulfonyl)methylamine in the presence of a base such as sodium hydride as shown in Flow Diagram XLI.

FLOW DIAGRAM XLI

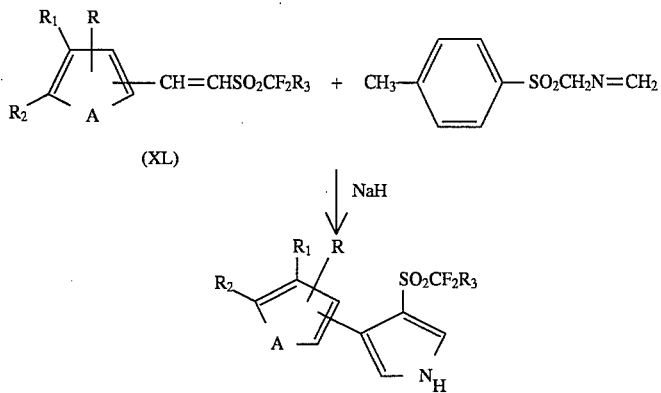

2-(Thienyl and furyl)-3-nitro-5-(haloalkylthio)pyrrole compounds and 5-(thienyl and furyl)-3-nitro-2-(haloalkylthio)pyrrole compounds may be prepared by reacting a 2-(thienyl or furyl)-5-(haloalkylthio)pyrrole compound with fuming nitric acid in the presence of acetic anhydride as shown in Flow Diagram XLII.

FLOW DIAGRAM XLII

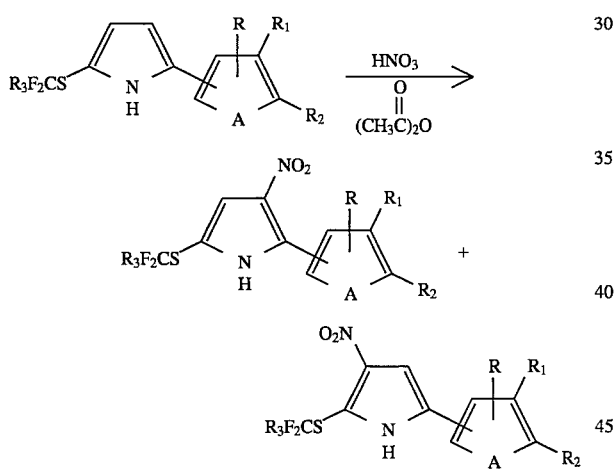

wherein A and $R_3$ are as described above for formula I and R, $R_1$ and $R_2$ are halogen.

Similarly, 2-(2-thienyl)-5-nitro-3-(haloalkylsulfonyl)pyrrole compounds and 2-(3-thienyl)-5-nitro-3-(haloalkylsulfonyl)pyrrole compounds may be prepared as shown in Flow Diagrams XLIII and XLIV, respectively.

FLOW DIAGRAM XLIII

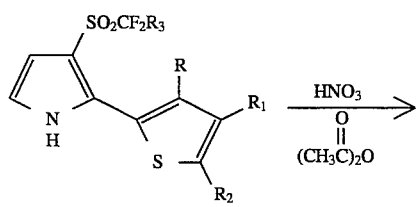

-continued
FLOW DIAGRAM XLIII

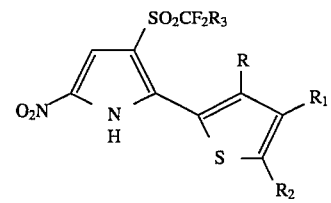

wherein A and $R_3$ are as described above for formula I and R, $R_1$ and $R_2$ are as described in Flow Diagram XI.

FLOW DIAGRAM XLIV

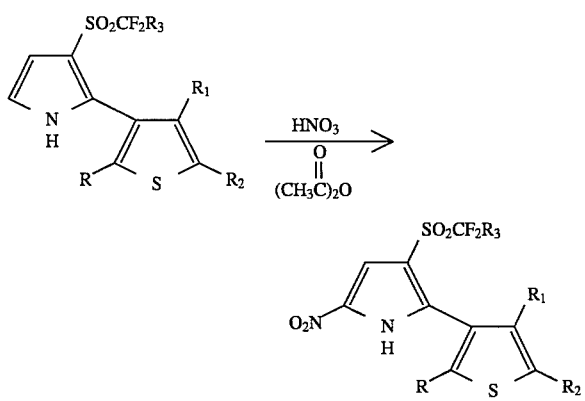

wherein A and $R_3$ are as described above for formula I and R, $R_1$ and $R_2$ are as described in Flow Diagram XII.

Methods for preparing 2-(2-thienyl)-3-(haloalkylthio)pyrrole compounds and 2-(3-thienyl)-3-(haloalkylthio)pyrrole compounds are shown in Flow Diagrams XLV and XLVI, respectively.

FLOW DIAGRAM XLV
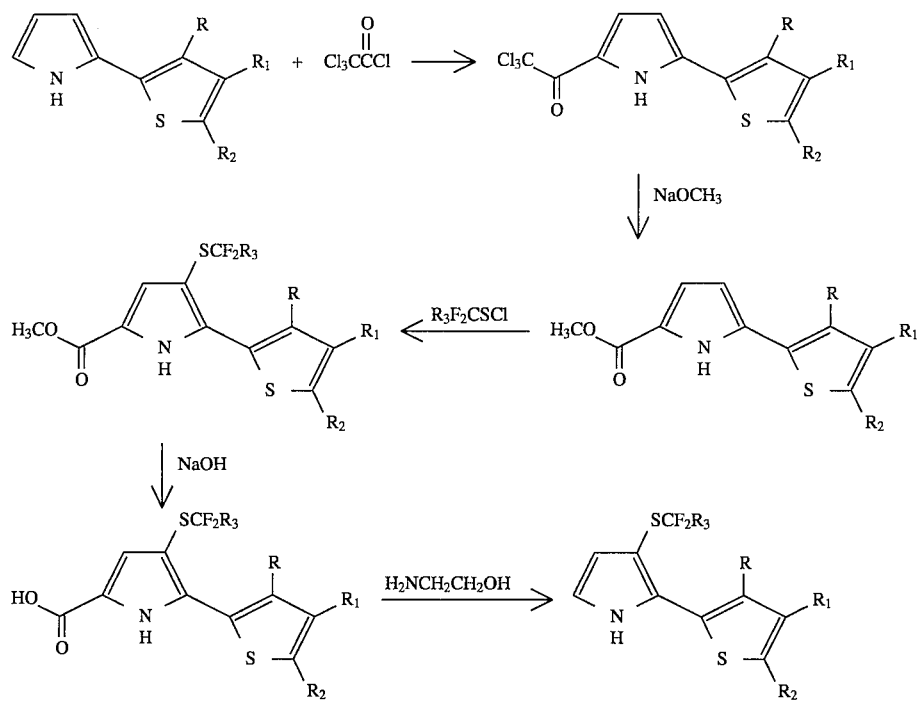
wherein R, $R_1$ and $R_2$ are as described in Flow Diagram XI.
FLOW DIAGRAM XLVI
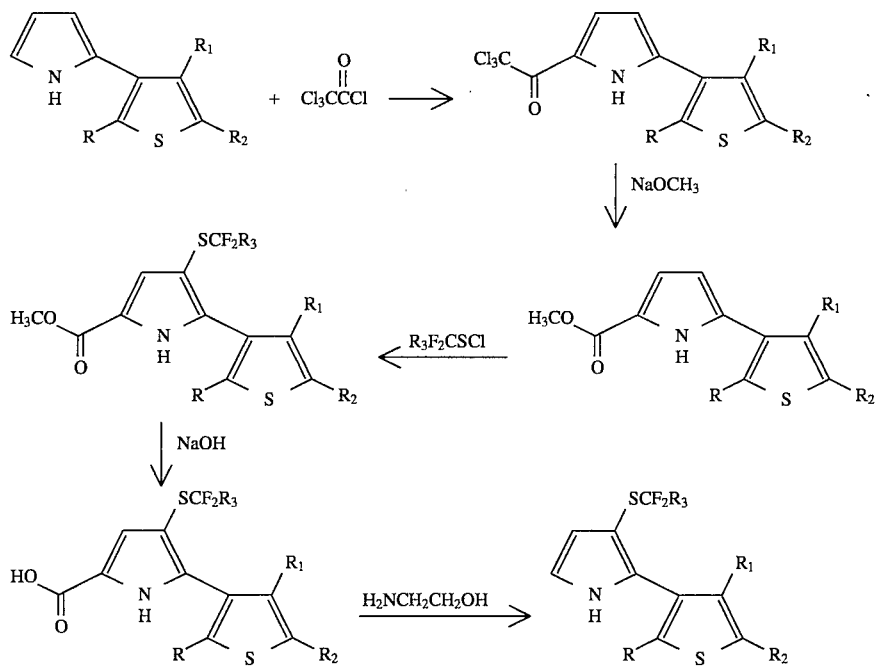
wherein R, $R_1$ and $R_2$ are as described in Flow Diagram XII.
3-Bromo-5-(thienyl or furyl)-2-(haloalkylsulfinyl and -sulfonyl-4-(haloalkylsulfonyl)pyrrole compounds may be prepared as shown in Flow Diagrams XLVII and XLVIII.

FLOW DIAGRAM XLVII
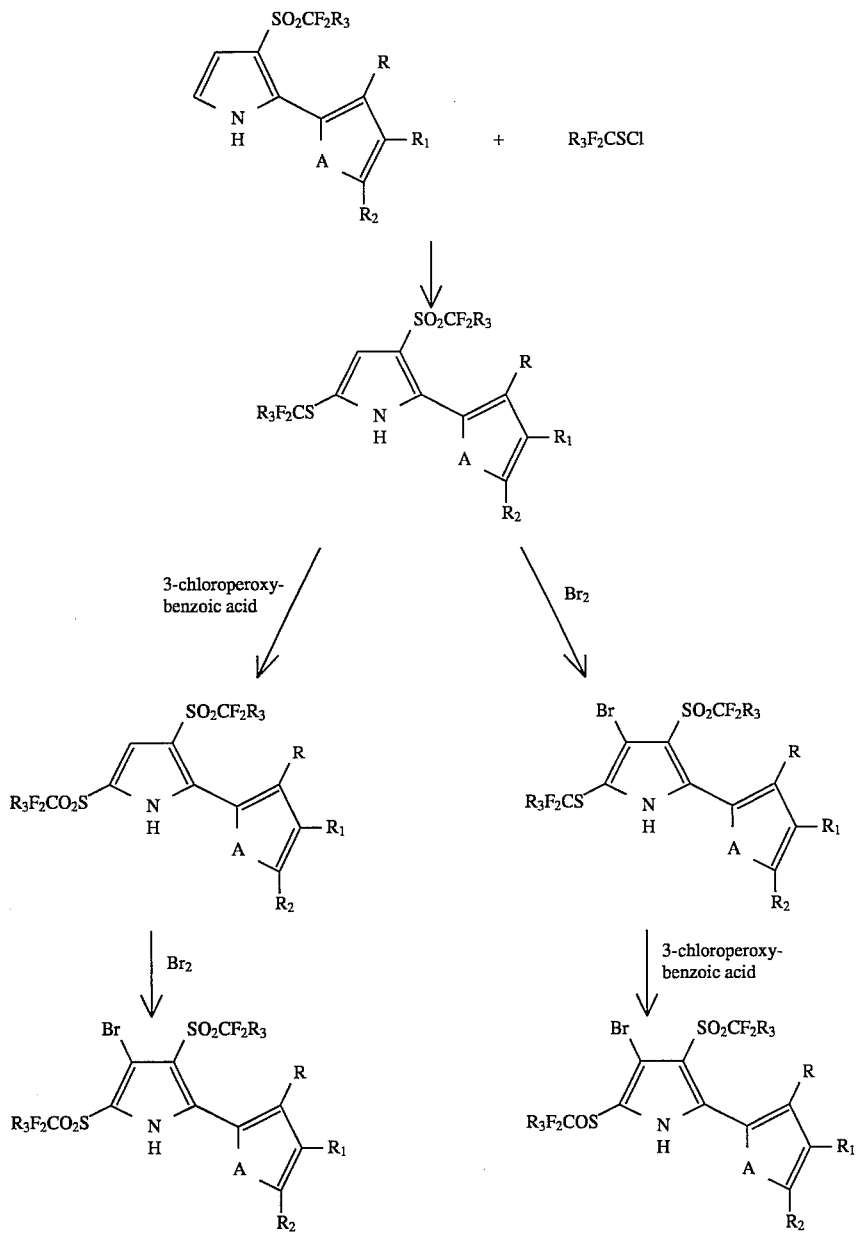
wherein A and R are as described above for formula I and R, $R_1$ and $R_2$ are as described in Flow Diagram XI.,

FLOW DIAGRAM XLVIII

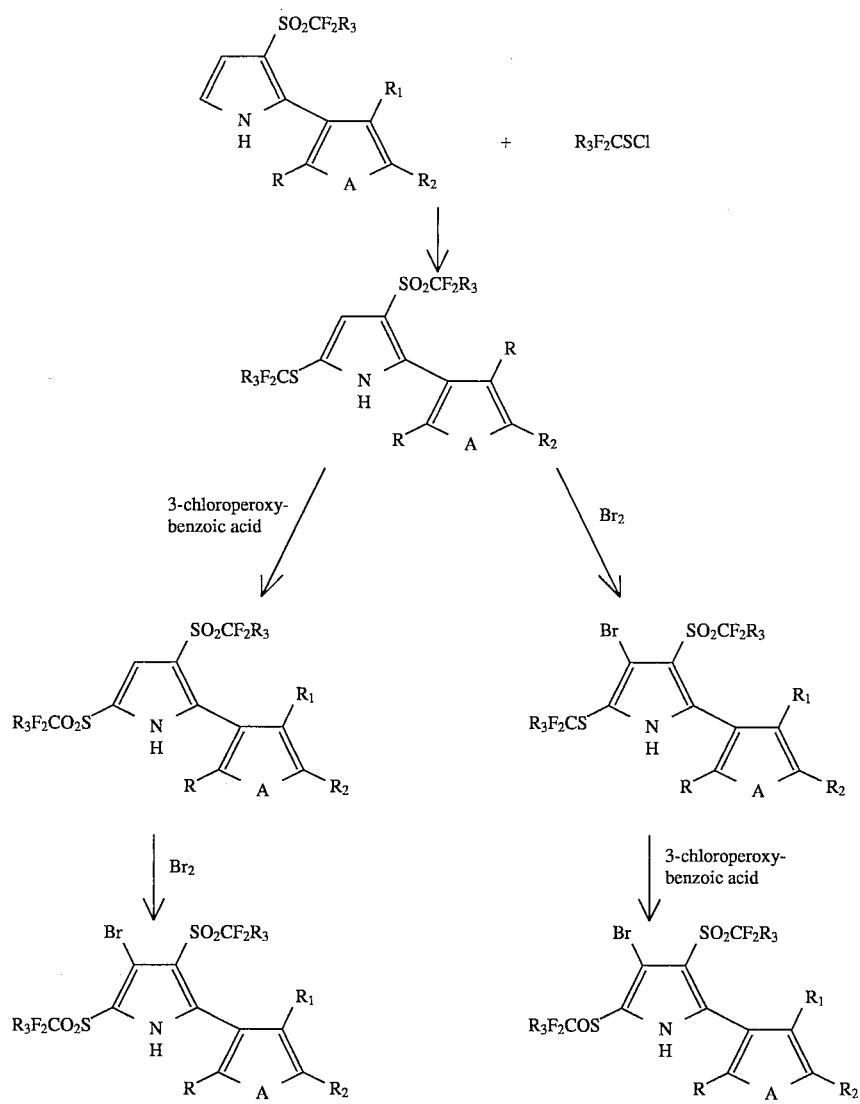

wherein A and R are as described above for formula I and R, $R_1$ and $R_2$ are as described in Flow Diagram XII.

2-(Thienyl and furyl)-4-aryl-5-haloalkyl-3-(haloalkylsulfonyl)pyrrole compounds may be prepared as shown in Flow Diagram XLIX.

FLOW DIAGRAM XLIX

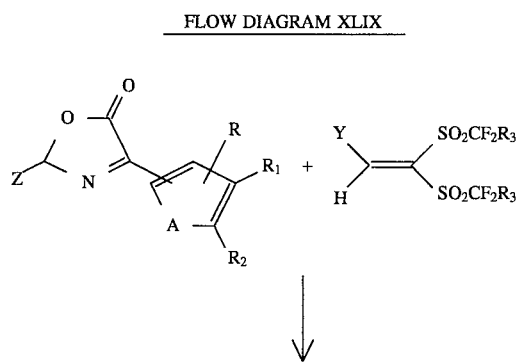

-continued
FLOW DIAGRAM XLIX

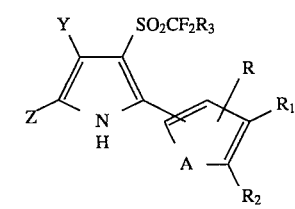

wherein A, R, $R_1$, $R_2$, Y and Z are as described in Flow Diagram XXI and $R_3$ is as described above for formula I.

Similarly, 2-aryl-4-(thienyl and furyl)-5-haloalkyl-3-(haloalkylsulfonyl)pyrrole compounds may be prepared as shown in Flow Diagram L.

FLOW DIAGRAM L

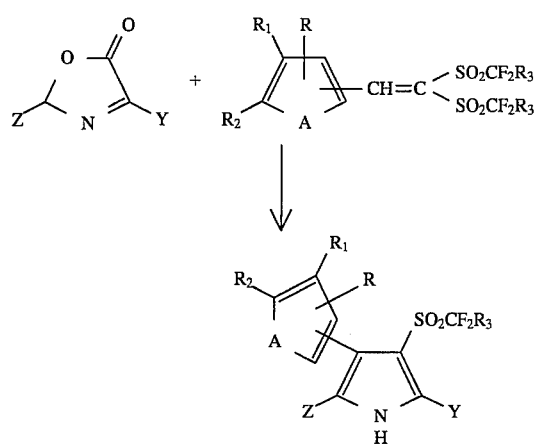

wherein A, R, $R_1$, $R_2$, Y and Z are as described in Flow Diagram XXI and $R_3$ is as described above for formula I.

2-(Thienyl and furyl)-5-(haloalkylsulfonyl)pyrrole-3-carbonitrile compounds may be prepared as shown in Flow Diagram LI.

FLOW DIAGRAM LI

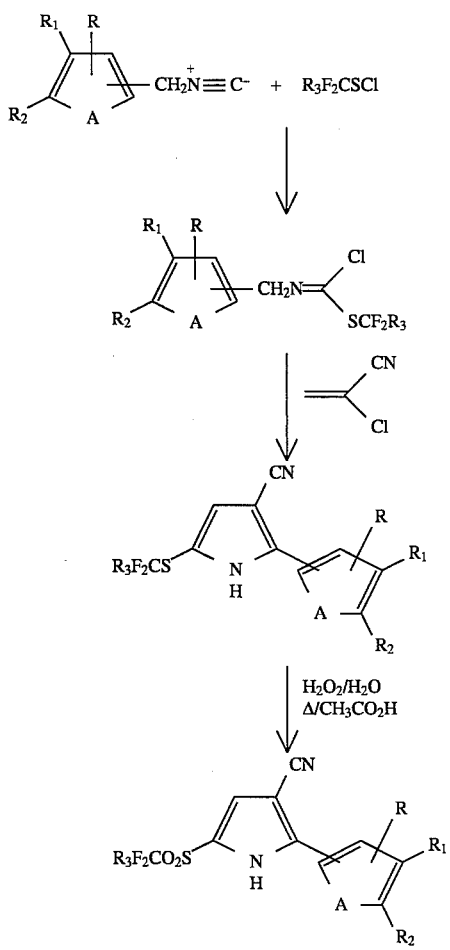

Conversion of formula I compounds wherein Y and/or Z are hydrogen to the corresponding formula I compounds wherein Y and/or Z are halogen is readily achieved by reaction of the formula I hydrogen substituted pyrrole with at least about 1 or 2 equivalents of a halogenating agent such as a sulfuryl halide, bromine or chlorine in the presence of a solvent such as dioxane, tetrahydroforan, acetic acid or a chlorinated hydrocarbon solvent. In addition, formula I compounds wherein R, $R_1$ and/or $R_2$ are hydrogen may be converted to the corresponding formula I compounds wherein R, $R_1$ and/or $R_2$ are halogen by reaction of the formula I compound wherein R, $R_1$ and/or $R_2$ are hydrogen with a halogenating agent in the presence of a solvent. Halogenating agents that may be employed include bromine, sulfuryl chloride, sulfuryl bromide, sodium hypochlorite, t-butylhypochlorite, N-bromosuccinimide, N-iodosuccinimide and the like. Several halogenation reaction schemes are shown in Flow Diagram LII.

FLOW DIAGRAM LII

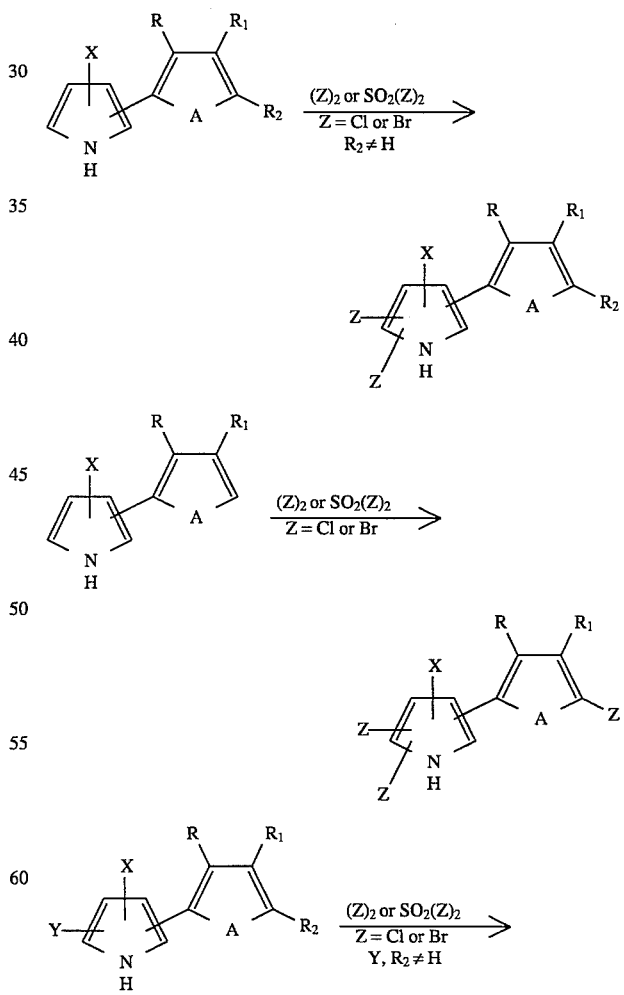

-continued
FLOW DIAGRAM LII

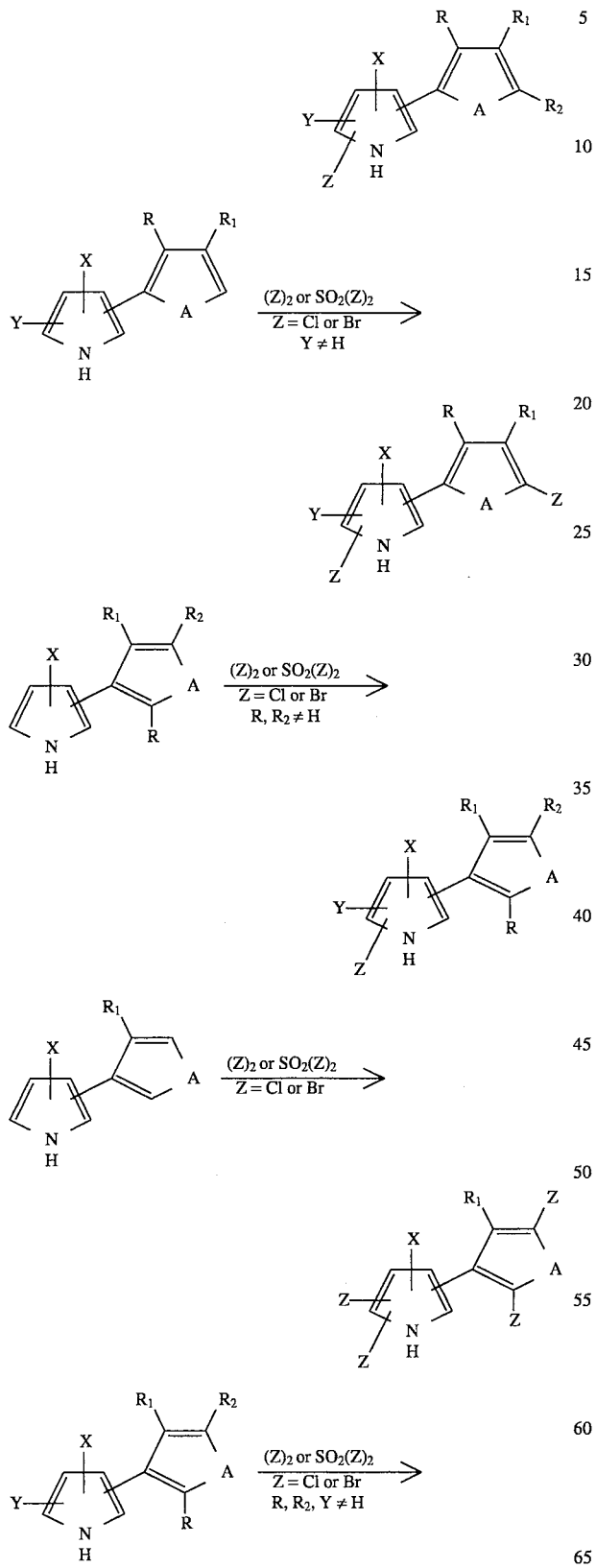

-continued
FLOW DIAGRAM LII

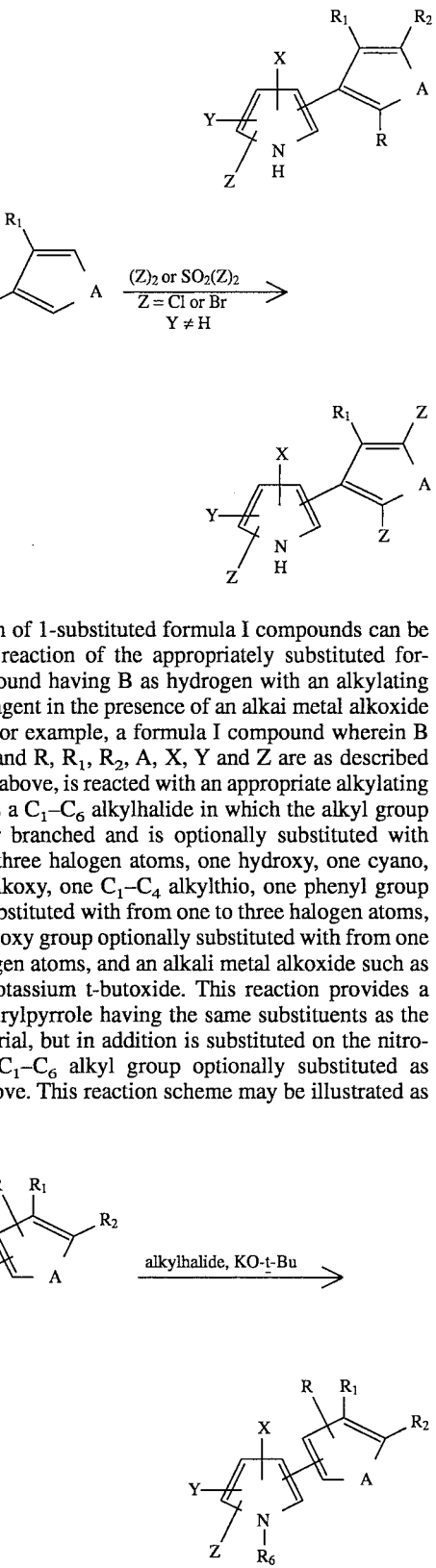

Preparation of 1-substituted formula I compounds can be achieved by reaction of the appropriately substituted formula I compound having B as hydrogen with an alkylating or acylating agent in the presence of an alkai metal alkoxide or hydride. For example, a formula I compound wherein B is hydrogen and R, $R_1$, $R_2$, A, X, Y and Z are as described for formula I above, is reacted with an appropriate alkylating agent such as a $C_1$–$C_6$ alkylhalide in which the alkyl group is straight or branched and is optionally substituted with from one to three halogen atoms, one hydroxy, one cyano, one $C_1$–$C_4$ alkoxy, one $C_1$–$C_4$ alkylthio, one phenyl group optionally substituted with from one to three halogen atoms, or one benzyloxy group optionally substituted with from one to three halogen atoms, and an alkali metal alkoxide such as sodium or potassium t-butoxide. This reaction provides a thienyl- or furylpyrrole having the same substituents as the starting material, but in addition is substituted on the nitrogen with a $C_1$–$C_6$ alkyl group optionally substituted as described above. This reaction scheme may be illustrated as follows:

wherein R, $R_1$, $R_2$, A, X, Y and Z are as described for formula I above and $R_6$ is $C_1$–$C_6$ alkyl optionally substituted as described above. In a similar reaction cyanogen bromide is substituted for the alkylhalide and yields a formula I thienyl- or furylpyrrole having a carbonitrile, rather than an alkyl group on the 1-position.

Advantageously, the above-described alkylation procedure may also be applied to the preparation of formula I thienyl- and furylpyrroles having an N-$C_3$–$C_6$ alkenyl or N-$C_3$–$C_6$ alkynyl substituent. This substitution is obtained by simply substituting a $C_3$–$C_6$ alkenyl halide or $C_3$–$C_6$ alkynyl halide for the $C_1$–$C_6$ alkyl halide in the above-described reaction.

In a similar manner, preparation of 1-acylated thienyl- and furylpyrroles may be achieved by the reaction of an appropriately substituted formula I thienyl- or furylpyrrole wherein B is hydrogen with an acylating agent in the presence of an alkali metal alkoxide. Acylating agents such as $C_1$–$C_6$ alkyl or $C_2$–$C_6$ alkenyl acid chlorides, substituted $C_1$–$C_6$ alkyl or $C_2$–$C_6$ alkenyl acid chlorides, benzoyl chloride, substituted benzoyl chlorides, phenylchloroformate, substituted phenylchloroformates, $C_1$–$C_6$ alkyl or $C_2$–$C_6$ alkenylchloroformates, substituted $C_1$–$C_6$ alkyl or $C_2$–$C_6$ alkenylchloroformates, N-substituted carbamoyl chlorides and the like may be employed. The reaction may be illustrated as follows:

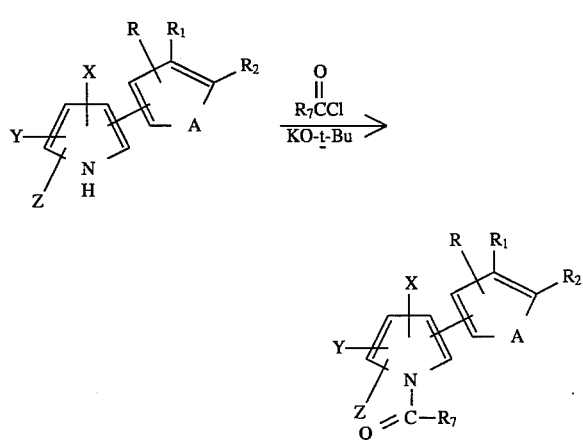

Formula I thienyl- and furylpyrroles wherein $R_6$ is $CH_2SQ$ may be prepared by reaction of the appropriately substituted formula I thienyl- or furylpyrrole having $R_6$ as chloromethyl with an alkali metal salt of an SQ compound in the presence of a base. And formula I thienyl- and furylpyrrole compounds wherein $R_6$ is $CHR_8NHC(O)R_9$ may be prepared a shown below.

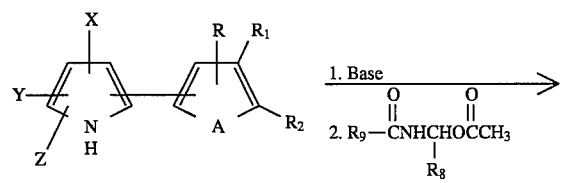

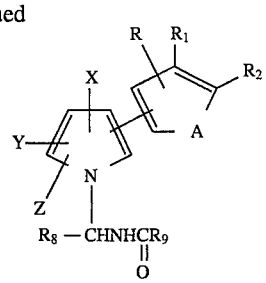

Advantageously, 1-halomethyl thienyl- and furylpyrroles may be prepared as shown below.

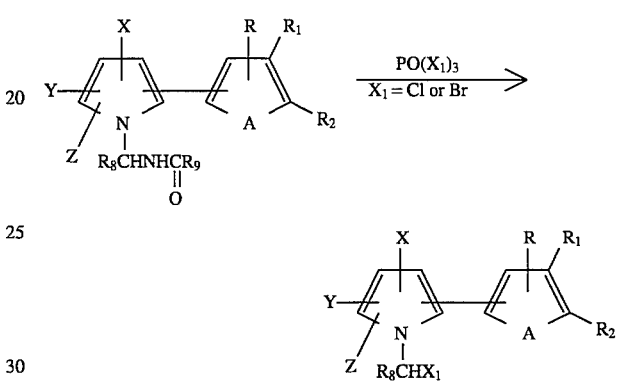

Formula I compounds wherein $R_6$ is $R_{10}CHOC(O)(CR_{11}R_{12})_nQ_1$ may be prepared as shown below.

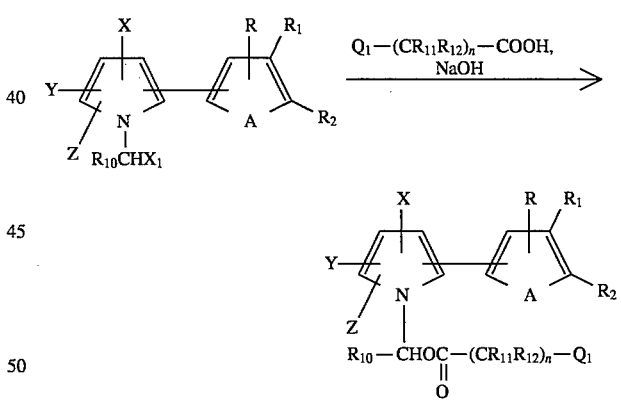

Formula I compounds wherein B is $OR_6$ may be prepared by reacting an appropriately substituted formula I thienyl- or furylpyrrole compound, wherein B is OH, and R, $R_1$, $R_2$, A, X, Y and Z are as described for formula I above, with an appropriate alkylating agent and a suitable base, for example, a chloromethyl $C_1$–$C_4$ alkyl ether and potassium t-butoxide. This reaction provides a thienyl- or furylpyrrole having the same substituents as the starting material, but in addition is substituted on the oxygen with $C_1$–$C_4$ alkoxymethyl. In a similar reaction bromoacetonitrile is substituted for the chloromethyl $C_1$–$C_4$ alkyl ether and gives a formula I thienyl- or furylpyrrole with an acetonitrile substituent on the oxygen. The reactions may be illustrated as follows:

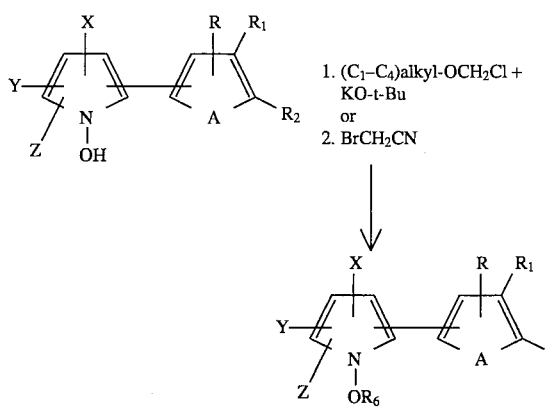

wherein R, $R_1$, $R_2$, A, X, Y and Z are as described for formula I above and $R_6$ is (1) $C_1$–$C_4$ alkoxymethyl or (2) $CH_2CN$.

Similarly, formula I compounds wherein B is $C(O)R_7$ may be prepared by reacting an appropriately substituted formula I thienyl- or furylpyrrole compound, wherein B is OH, and R, $R_1$, $R_2$, A, X, Y and Z are as described for formula I above, with an appropriate acylating agent and a suitable base, for example, a $C_1$–$C_6$ acid chloride and potassium t-butoxide. This reaction provides a thienyl- or furylpyrrole compound having the same substituents as the starting material, but in addition is substituted on the oxygen with $C_1$–$C_6$ alkanoyl. The reaction may be illustrated as follows:

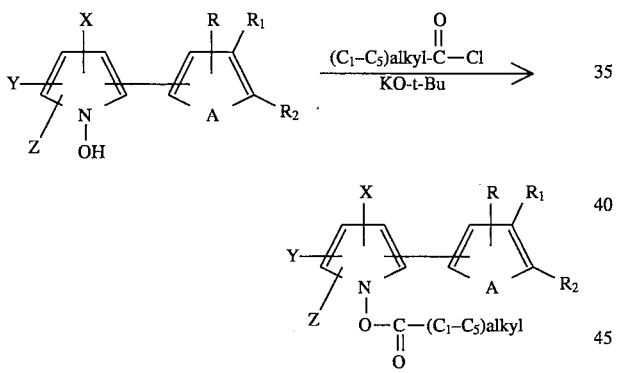

The formula I compounds of this invention are especially useful for controlling or preventing the growth of phytopathogenic fungi such as *Venturia inaequalis, Plasmopara viticola, Puccinia recondita* f. sp. tritici and *Erysiphe graminis* f. sp. tritici. Therefore, harmful diseases such as apple scab, grape downy mildew, wheat leaf rust and wheat powdery mildew may be prevented or controlled.

The thienyl- and furylpyrrole compounds of the present invention are also useful for the protection of growing or harvested plants from the damage caused by phytopathogenic fungal disease when applied to said plants at a fungicidally effective rate. The effective rate will vary depending upon factors such as the virulence of the target fungus, the environment of the treatment and other ambient conditions. In practice, generally about 20 ppm to 1,000 ppm, preferably about 50 ppm to 500 ppm of a formula I thienyl- or furylpyrrole compound may be dispersed in a liquid or solid carrier and applied to the plant, seed or tuber, or to the medium or water in which the plant, seed or tuber is growing.

The formula I fungicidal compounds of the invention may be formulated as concentrated solutions, emulsifiable concentrates, flowable concentrates, microemulsions and the like. Said compounds may also be formulated as dry compacted granules, granular compositions, dusts, dust concentrates, suspension concentrates, wettable powders, and the like. Those formulations which lend themselves to seed, tuber, medium, water and/or foliage applications to provide the requisite plant protection are suitable. Such formulations include the fungicidal compounds of the invention admixed with an inert solid or liquid carrier.

It is contemplated that the fungicidal compounds of the invention may be used in conjunction with, or in combination with, a pesticidally effective amount of one or more other pesticides, including but not limited to, anilazine, benalaxyl, benomyl, bitertanol, bordeaux mixture, carbendazim, carboxin, captafol, captan, chlorothalonil, cyproconazole, dichloran, diethofencarb, diniconazole, dithianon, dodine, edifenphos, fenarimol, fenbuconazole, fenfuram, fenpropidin, fenpropimorph, fentin hydroxide, ferbam, flusilazole, flusulfamide, flutriafol, folpet, fosetyl, fuberidazole, guazatine, hexaconazole, imazalil, iprobenfos, iprodione, mancozeb, maneb, metalaxyl, metiram, myclobutanil, nuarimol, ofurace, oxadixyl, oxycarboxin, penconazole, probenazole, prochloraz, propiconazole, pyrazophos, tebuconazole, thiabendazole, thiophanate, thiophanate-methyl, triadimefon, triadimenol, triarimol, tricyclazole, tridemorph, triflumizole, triforine, vinclozolin, and/or zineb.

Where compositions of the invention are to be employed in combination treatments with other pesticidal agents, the composition may be applied concurrently as an admixture of the components as described above, or may be applied sequentially.

In order to facilitate a further understanding of the invention, the following examples are presented primarily for the purpose of illustrating more specific details thereof. The examples generally utilize the above reation schemes and also provide further means for preparing even more compounds of the present invention which are not specifically described above. The invention should not be deemed limited by the examples as the full scope of the invention is defined in the claims.

EXAMPLE 1

Preparation of
3,4,5-Trichloro-2-Thiophenecarboxaldehyde

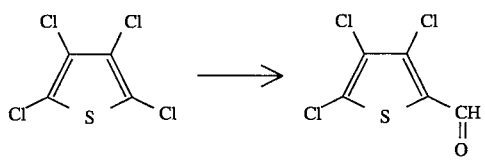

Butyllithium (2.5 molar in tetrahydrofuran, 3.96 mL, 9.9 mmol) is added to a solution of tetrachlorothiophene (2.00 g, 9.01 mmol) in tetrahydrofuran at 0° C. The reaction mixture is stirred at 0° C. for 30 minutes, warmed to room temperature over 45 minutes, treated with N,N-dimethylformamide (0.79 g, 10.8 mmol), stirred for three hours, poured into one molar hydrochloric acid at 4° C. and extracted with ether. The combined organic extracts are washed sequentially with water and brine, dried over $MgSO_4$ and concentrated in vacuo to obtain a brown solid. Flash chromatography of the solid using silica gel and a 5% ethyl acetate in hexane solution gives a beige solid which is recrystallized from ethyl acetate and hexane to obtain the title product as beige needles (1.63 g, 84%, mp 81°–82° C.).

EXAMPLE 2

Preparation of the Oxime of 3,4,5-Trichloro-2-Thiophenecarboxaldehyde

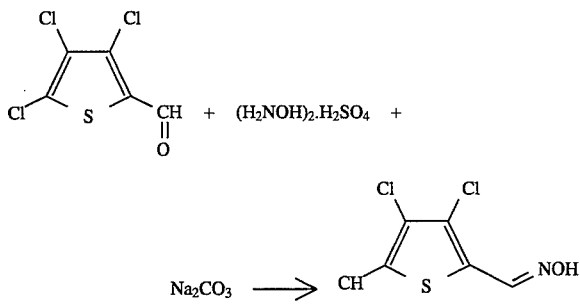

A solution of sodium carbonate (10.91 g, 99.2 mmol) in water is added to a slurry of 3,4,5-trichloro-2-thiophenecarboxaldehyde (10.69 g, 49.6 mmol) and hydroxylamine sulfate (8.14 g, 49.6 mmol) in water. After stirring at room temperature for 18 hours, the solids are filtered out of the reaction mixture and dried under high vacuum overnight to give the title product as a white solid (10.24 g, 92%).

Using essentially the same procedure, and employing the appropriately substituted thiophenecarboxaldehyde, the following compounds are obtained.

| R | $R_1$ | $R_2$ |
|---|---|---|
| H | H | Cl |
| H | Br | H |
| H | —CH=CH—CH=CH— | |
| H | H | H |

EXAMPLE 3

Preparation of 3,4,5-Trichloro-2-Thiophenecarbonitrile

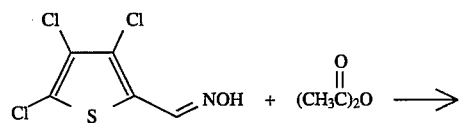 + (CH₃C)₂O →

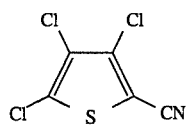

A solution of the oxime of 3,4,5-trichloro-2-thiophenecarboxaldehyde (10.08 g, 43.7 mmol) in acetic anhydride is refluxed for two hours and concentrated in vacuo to obtain a brown oil. The oil is diluted with ether and the organic solution is washed sequentially with water and brine, dried over MgSO₄ and concentrated in vacuo to give a brown oil. Flash chromatography of the oil using silica gel and a 5% ethyl acetate in hexane solution gives a beige solid which is recrystallized from ethyl acetate and hexane to obtain the title product as beige needles (8.23 g, 89%, mp 63°–64° C.).

Using essentially the same procedure, and employing the appropriately substituted oxime, the following compounds are obtained:

| R | $R_1$ | $R_2$ |
|---|---|---|
| H | H | Cl |
| H | Br | H |
| H | —CH=CH—CH=CH— | |
| H | H | H |

EXAMPLE 4

Preparation of 2-(3,4,5-Trichloro-2-Thienyl)-5-(Trifluoromethyl) Pyrrole-3-Carbonitrile

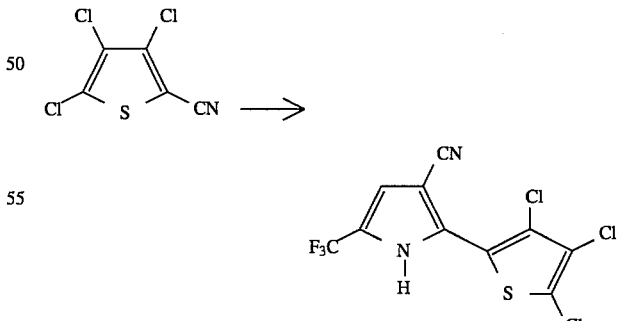

Acetonitrile (0.97 g, 23.7 mmol) is added dropwise to a solution of lithium diisopropylamide (two molar in hydrocarbons, 10.9 mL, 21.8 mmol) in tetrahydrofuran at −78° C. The reaction mixture is stirred at −78° C. for 30 minutes, treated with a solution of 3,4,5-trichloro-2-thiophenecarbonitrile (3.87 g, 18.2 mmol) in tetrahydrofuran, stirred for 30 minutes at −78° C., warmed to room temperature over 45 minutes, quenched with saturated ammonium chloride solution and extracted with ether. The combined organic extracts are washed sequentially with water and brine, dried over MgSO$_4$ and concentrated in vacuo to obtain a red solid. A mixture of the red solid and 1-bromo-3,3,3-trifluoroacetone (1.95 mL, 18.7 mmol) in acetic acid is refluxed for three hours and 30 minutes, diluted with water and extracted with ether. The combined organic extracts are washed sequentially with water and brine, dried over MgSO$_4$ and concentrated in vacuo to obtain a red solid. Flash chromatography of the solid using silica gel and a 15% ethyl acetate in hexane solution gives the title product as a white solid (0.49 g, 7.8%, mp 220°–221° C.).

Using essentially the same procedure, and employing the appropriately substituted cyanofuran or cyanothiophene, the following compounds are obtained:

| A | R | R$_1$ | R$_2$ | mp°C. |
|---|---|---|---|---|
| S | H | H | H | 210 |
| S | H | H | Br | 230–231 |
| S | H | H | Cl | 232–233 |
| S | H | Br | H | >230 |
| O | H | H | H | 196–197 |
| S | H | —CH=CH—CH=CH— | | >230 |
| S | Cl | —CH=CH—CH=CH— | | 193–195 |

| A | R | R$_1$ | R$_2$ | mp°C. |
|---|---|---|---|---|
| S | H | H | H | 229–231 |

EXAMPLE 5

Preparation of 4-Bromo-2-(3,4,5-Trichloro-2-Thienyl)-5-(Trifluoromethyl)Pyrrole-3-Carbonitrile

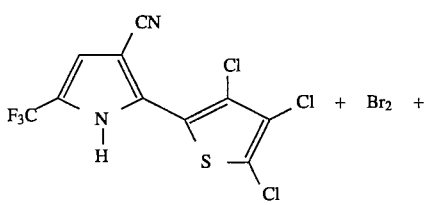 + Br$_2$ + CH$_3$CO$_2$Na/CH$_3$CO$_2$H ⟶ 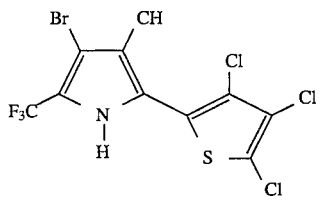

Bromine (0.21 g, 1.31 mmol) is added to a solution of 2-(3,4-5-trichloro-2-thienyl)-5-(trifluoromethyl)pyrrole-3-carbonitrile (0.38 g, 1.09 mmol) and sodium acetate (0.11 g, 1.31 mmol) in acetic acid at 50° C. After stirring at 50° C. for 30 minutes, additional sodium acetate (0.11 g, 1.31 mmol) and bromine (0.208 g, 1.31 mmol) are added to the reation mixture. The reaction mixture is stirred for 15 minutes, cooled to room temperature and poured into a 1% sodium bisulfite solution. The solids are filtered out of the aqueous mixture and dried overnight under high vacuum to give a white solid. The solid is recrystallized from ethyl acetate and hexane to obtain the title product as white crystals (0.45 g, 96%, mp 221°–224° C.).

Using essentially the same procedure, and employing the appropriately substituted 2-(thienyl or furyl)-5-(trifluoromethyl)pyrrole-3-carbonitrile, the following compounds are obtained:

| A | R | R$_1$ | R$_2$ | mp°C. |
|---|---|---|---|---|
| S | H | H | Br | 254 (dec.) |
| S | H | H | Cl | >230 |
| S | H | Br | Br | >230 |
| O | H | H | Br | >230 |
| S | Br | —CH=CH—CH=CH— | | 201–203 |
| S | Cl | —CH=CH—CH=CH— | | 205–206 |

| A | R | R$_1$ | R$_2$ | mp°C. |
|---|---|---|---|---|
| S | Br | H | H | 183–185 |

EXAMPLE 6

Preparation of
4-Bromo-1-(Ethoxymethyl)-2-(3,4,5-Trichloro-2-Thienyl)-5-(Trifluoromethyl)Pyrrole-3-Carbonitrile

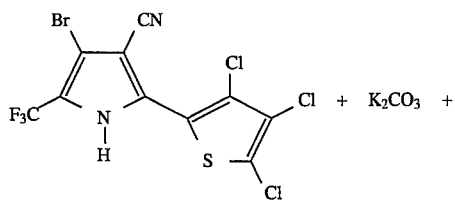

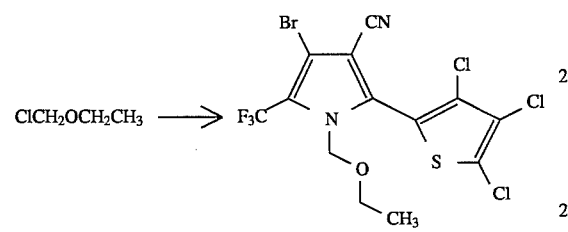

Chloromethyl ethyl ether (0.20 g, 2.13 mmol) is added to a mixture of 4-bromo-2-(3,4,5-trichloro-2-thienyl)-5-(trifluoromethyl)pyrrole-3-carbonitrile (0.30 g, 0.71 mmol) and potassium carbonate (0.29 g, 2.13 mmol) in N,N-dimethylformamide. The reation mixture is stirred at room temperature for 30 minutes, diluted with water and extracted with ether. The combined organic extracts are washed sequentially with water and brine, dried over MgSO₄ and concentrated in vacuo to obtain a clear oil. Flash chromatography of the oil using silica gel and a 15% ethyl acetate in hexane solution gives the title product as white crystals (0 24 g, 71%, mp 85°14 87° C.)

Using essentially the same procedure, and employing the appropriately substituted 4-halo-2-(thienyl or furyl) -5- (trifluoromethyl) pyrrole-3-carbonitrile, the following compounds are obtained:

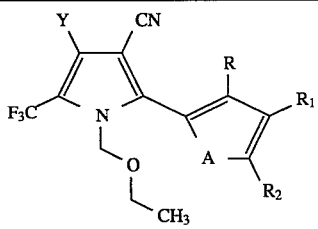

| Y | A | R | R₁ | R₂ | mp°C. |
|---|---|---|----|----|-------|
| Cl | S | H | H | H | 82–83 |
| Br | S | H | H | Br | 81–83 |
| Br | S | H | H | Cl | 81–83 |
| Br | O | H | H | Br | 80–81 |
| Br | S | Br | —CH=CH—CH=CH— | | 111–113 |
| Br | S | Cl | —CH=CH—CH=CH— | | 113–115 |

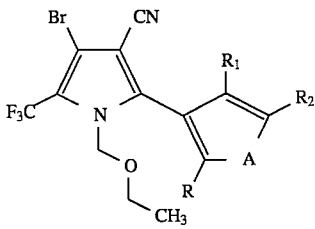

| A | R | R₁ | R₂ | mp°C. |
|---|---|----|----|-------|
| S | Br | H | H | 109–110 |

EXAMPLE 7

Preparation of
4-Chloro-2-(2-Thienyl)-5-(Trifluoromethyl)Pyrrole-3-Carbonitrile

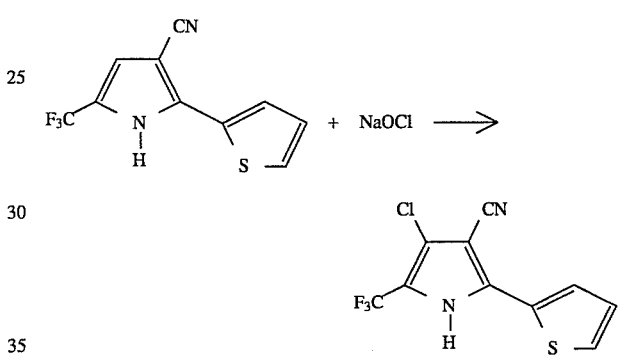

Sodium hypochlorite (12 mL of a 5.25% solution, 17 mmol) is added dropwise to a solution of 2-(2-thienyl)-5-(trifluoromethyl)pyrrole-3-carbonitrile (2.00 g, 8.26 mmol) in tetrahydrofuran. The reaction mixture is stirred for 2 hours and 15 minutes, quenched with a 1% sodium bisulfite solution and diluted with ether. The layers are separated and the organic layer is washed sequentially with water and brine, dried over MgSO₄ and concentrated in vacuo to obtain a yellow solid. Flash chromatography of the solid using silica gel and a 15% ethyl acetate in hexane solution gives a solid which is recrystallized from ethyl acetate and hexane to obtain the title product as a yellow solid (0.35 g, 15%, mp 221°–223° C.).

EXAMPLE 8

Preparation of 5-Bromo-2-Thiophenecarbonitrile

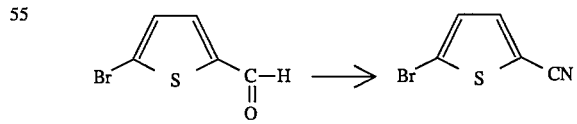

Hydroxylamine-O-sulfonic acid (17.58 g, 157 mmol) is added to a solution of 5-bromo-2-thiophenecarboxaldehyde (15.00 g, 78.5 mmol) in water and acetonitrile. The reaction mixture is stirred for 17 hours, poured into water and extracted with ether and ethyl acetate. The combined organic extracts are washed sequentially with water and brine, dried over MgSO₄ and concentrated in vacuo to give a brown, oily solid. A solution of the oily solid in acetic anhydride is refluxed for five hours, concentrated in vacuo, poured into water and extracted with ether. The combined organic extracts are washed sequentially with water, half-saturated sodium hydrogen carbonate solution and brine, dried over MgSO₄ and concentrated in vacuo to obtain a brown oil. Flash chromatography of the oil using silica gel and a 15% ethyl acetate in hexane solution gives the title product as a yellow oil (3.60 g, 24%).

EXAMPLE 9

Preparation of 2-(5-Bromo-2-Furyl)-5-(Trifluoromethyl)Pyrrole-3-Carbonitrile

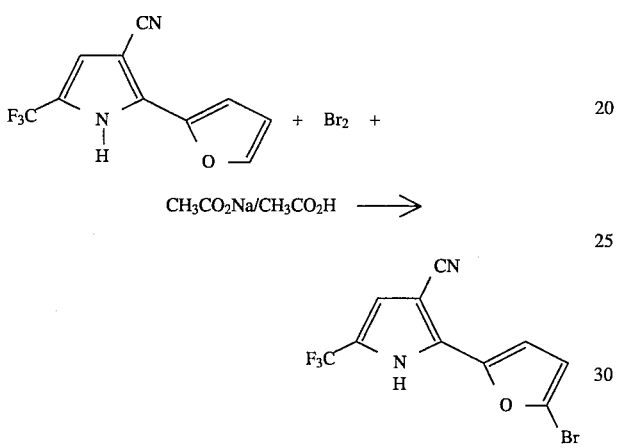

Bromine (0.71 g, 4.42 mmol) is added to a solution of 2-(2-furyl)-5-(trifluoromethyl)pyrrole-3-carbonitrile (1.00 g, 4.42 mmol) and sodium acetate (0.36 g, 4.42 mmol) in acetic acid. The reation mixture is stirred for 15 minutes and poured into a 1% sodium bisulfite solution. The solids are filtered from the aqueous mixture, dried overnight under high vacuum and recrystallized from ethyl acetate and hexane to obtain the title product as red crystals (1.21 g, 90% mp 224°–226° C.

Using essentially the same procedure, but substituting 2-(2-thienyl)-5-(trifluoromethyl)pyrrole-3-carbonitrile for 2-(2-furyl)-5-(trifluoromethyl)pyrrole-3-carbonitrile, 2-(2-bromo-3-thienyl)-5-(trifluoromethyl)pyrrole-3-carbonitrile is obtained as a solid, mp 170° C.

EXAMPLE 10

Preparation of 2-(5-Formyl-2-Furyl)-5-(Trifluoromethyl)Pyrrole-3-Carbonitrile

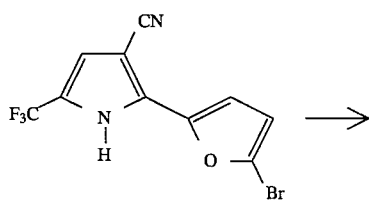

-continued

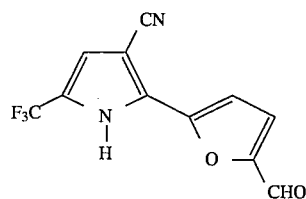

Butyllithium (3.45 mL, 7.78 mmol) is added dropwise to a solution of 2-(5-bromo-2-furyl)-5-(trifluoromethyl)pyrrole-3-carbonitrile (1.13 g, 3.70 mmol) in tetrahydrofuran at −78° C. The reation mixture is stirred at −78° C. for 30 minutes, warmed to room temperature, treated with N,N-dimethylformamide (1.35 g, 18.5 mmol), poured into one molar hydrochloric acid and extracted with ether and ethyl acetate. The combined organic extracts are washed sequentially with water and brine, dried over Na₂SO₄ and concentrated in vacuo to obtain an orange solid. Flash chromatography of the solid using silica gel and 20% to 50% ethyl acetate in hexane solutions give an orange solid which is recrystallized from ethyl acetate to obtain the title product as orange crystals (0.66 g, 70%, mp 224°–225° C.).

EXAMPLE 11

Preparation of Benzo[b]Thiophene-2-Carboxaldehyde

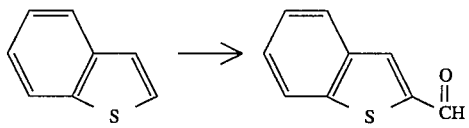

Butyllithium (54 mL, 134 mmol) is added dropwise to a solution of N,N,N',N'-tetramethylethylenediamine (15.57 g, 134 mmol) in tetrahydrofuran under nitrogen at 0° C. The reaction mixture is treated dropwise with a solution of benzothiophene (15.00 g, 112 mmol) in tetrahydrofuran, warmed to room temperature, treated with additional N,N,N',N'-tetramethylethylenediamine (15.57 g, 134 mmol) and butyllithium (54 mL, 134 mmol), stirred at room temperature for 13 hours, cooled to 0° C. treated with N,N-dimethylformamide (24.40 g, 336 mmol), warmed to room temperature, stirred for five hours, poured into one molar hydrochloric acid and extracted with ether. The combined organic extracts are washed sequentially with water and brine, dried over Na₂SO₄ and concentrated in vacuo to obtain an orange oil. Flash chromatography of the oil using silica gel and a 15% ethyl acetate in hexane solution gives the title product as an orange oil (12.51 g, 69%).

EXAMPLE 12

Preparation of
3-Chlorobenzo[b]Thiophene-2-Carbonitrile

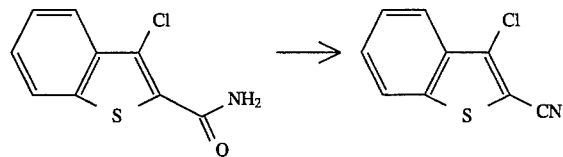

Trifluoroacetic anhydride (11.90 g, 56.6 mmol) is added dropwise to a mixture of pyridine (5.23 g, 66.1 mmol) and 3-chlorobenzo[b]thiophene-2-carboxamide (10.00 g, 47.2 mmol) in methylene chloride at 0° C. The reaction mixture is warmed to room temperature over one hour, diluted with water and extracted with ether. The combined organic extracts are washed sequentially with water, one molar hydrochloric acid and brine, dried over $MgSO_4$ and concentrated in vacuo to obtain a yellow solid. The solid is recrystallized from ethyl acetate and hexane to give the title product as off-white needles (8.80 g, 96%).

EXAMPLE 13

Preparation of
β-[(Formylmethyl)Amino-2-Benzofuranacrylontrile,
Diethyl Acetal

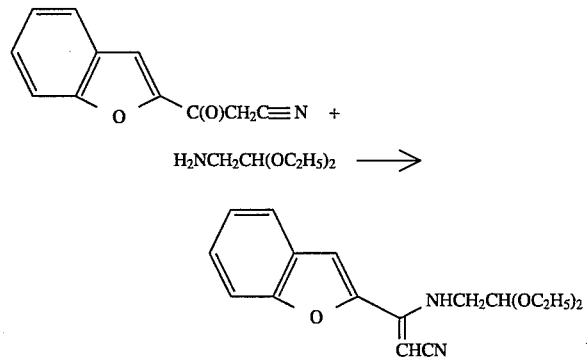

A mixture of 2-ω-cyanoacetobenzofuran (18.52 g, 100.0 mmol) and aminoacetaldehyde diethyl acetal (14.50 mL, 13.28 g, 99.7 mmol) in toluene is refluxed overnight with removal of water (Dean-Stark trap) and concentrated in vacuo to obtain a black oil. Dry column chromatography of the oil using silica gel and methylene chloride gives a reddish-black oil. The oil is mixed with a methylene chloride/hexane solution. The mixture is filtered and the filtrate is concentrated in vacuo to obtain the title product as a reddish-black oil, 10.20 g.

EXAMPLE 14

Preparation of
2-(2-Benzofuranyl)Pyrrole-3-Carbonitrile

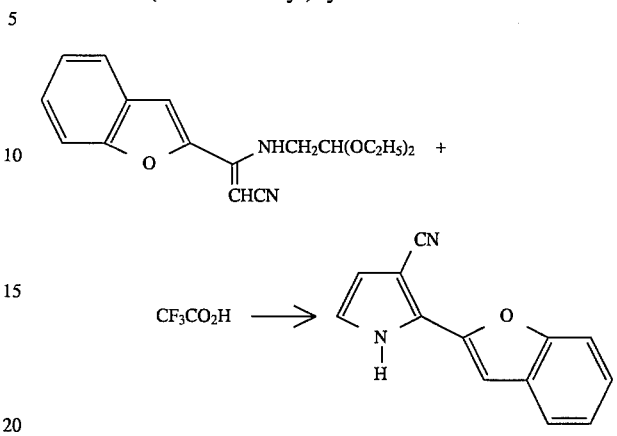

β-[(Formylmethyl)amino]-2-benzofuranacrylonitrile (1.00 g, 3.33 mmol) is added dropwise to trifluoroacetic acid (5 mL). The reaction mixture is stirred at room temperature for one hour, diluted with water and extracted with ethyl acetate. The organic extract is washed sequentially with saturated sodium hydrogen carbonate solution and brine, dried over $MgSO_4$, decolorized with charcoal and concentrated in vacuo to obtain an orange solid. Dry column chromatography of the solid using silica gel and methylene chloride gives the title product as a brown-white solid (0.32 g 46% mp 157°–160.5° C.

EXAMPLE 15

Preparation of
4,5-Dichloro-2-(3-Chloro-2-Benzofuranyl)Pyrrole-3-Carbonitrile

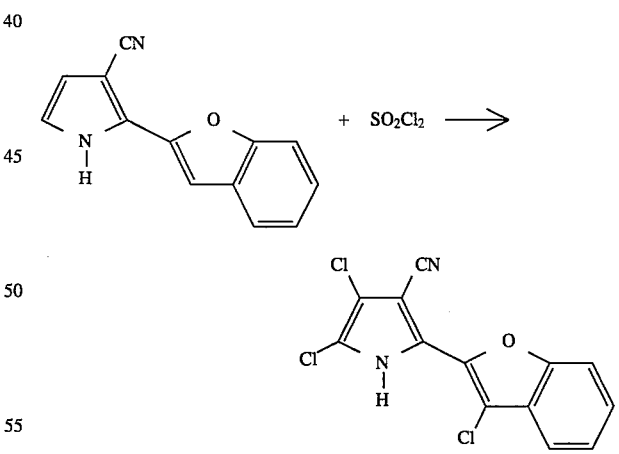

Sulfuryl chloride (1.20 mL, 2.02 g, 14.9 mmol) is added dropwise to a solution of 2-(2-benzofuranyl)pyrrole-3-carbonitrile (1.00 g, 4.8 mmol) in acetic acid. The reaction mixture is stirred at room temperature for 45 minutes and filtered to collect solids. The solids are washed with cold acetic acid and dried overnight to obtain a gray powder. A solution of the gray powder and tetrahydrofuran is dried over $MgSO_4$, decolorized with charcoal and concentrated in vacuo to give a yellow-white solid. A slurry of the yellow-white solid and methylene chloride is stirred for 90 minutes and filtered to obtain the title product as an off-white solid (0.74 g, mp 258°–260.5° C.).

Using essentially the same procedure, but employing two equivalents of sulfuryl chloride, 5-chloro-2-(3-chloro-2-benzofuranyl)pyrrole-3-carbonitrile is obtained as a white solid, mp 223.5°–225.5° C.

EXAMPLE 16

Preparation of
2-Bromo-1-(5-Chloro-2-Thienyl)Ethanone

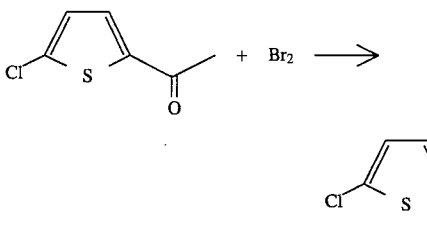

A solution of bromine (18.90 g, 118 mmol) in chloroform is added to a solution of 2-acetyl-5-chlorothiophene (19.00 g, 118 mmol) in chloroform at 40°– 45° C. The reaction mixture is stirred at room temperature for two hours and diluted with water. The organic layer is separated, dried over MgSO$_4$ and concentrated in vacuo to give a solid. The solid is slurried in an ether/hexane solution, filtered and dried to give the title product as a solid (12.20 g, mp 68°–70° C.).

EXAMPLE 17

Preparation of
[(5-Chloro-2-Thenoyl)Methyl]Malononitrile

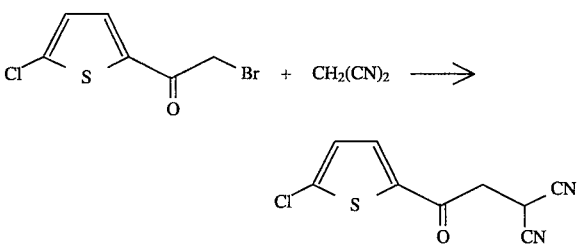

A solution of 2-bromo-1-(5-chloro-2-thienyl)ethanone (11.50 g, 48 mmol) in tetrahydrofuran is added to a solution of malononitrile (3.17 g, 48 mmol) and potassium tert-butoxide (5.70 g, 51 mmol) in tetrahydrofuran at 0° C. The reaction mixture is stirred for several minutes, concentrated in vacuo, diluted with water and filtered to collect solids. Flash chromatography of the solids using silica gel and a (4:1) hexane/ethyl acetate solution gives the title compound as a yellow solid, mp 155°–158° C.

EXAMPLE 18

Preparation of
2-Chloro-5-(5-Chloro-2-Thienyl)Pyrrole-3-Carbonitrile

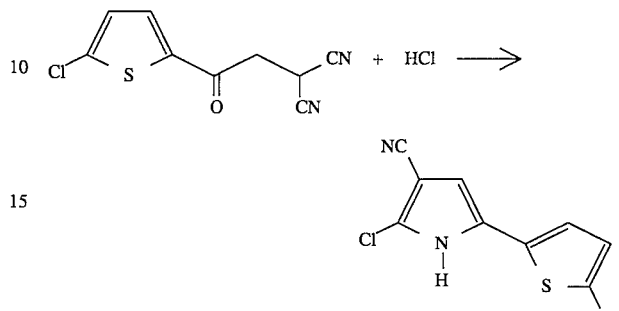

Hydrogen chloride gas is bubbled through a mixture of [(5-chloro-2-thenoyl)methyl]malononitrile (4.60 g, 20.5 mmol), ether and chloroform at a moderate rate for 20 minutes. The reaction mixture is poured into an ice-water mixture and extracted with ether. The combined organic extracts are dried over MgSO$_4$ and concentrated in vacuo to give a brown solid. The solid is mixed with a hexane/ether solution and filtered to obtain the title product as a brown solid, mp >200° C.

EXAMPLE 19

Preparation of
4-Bromo-2-Chloro-5-(5-Chloro-2-Thienyl)Pyrrole-3-Carbonitrile

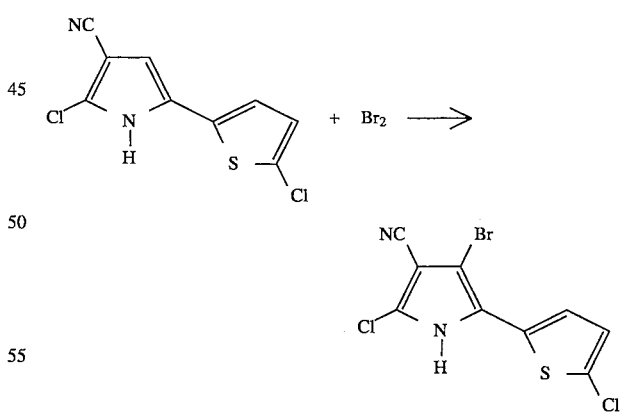

A solution of bromine (0.70 g, 4.3 mmol) in p-dioxane is added dropwise to a solution of 2-chloro-5-(5-chloro-2-thienyl)pyrrole-3-carbonitrile (1.00 g, 4.1 mmol) in p-dioxane. The reaction mixture is stirred overnight at room temperature and concentrated in vacuo to obtain a residue. Flash chromatography of the residue using silica gel and a (6:1) hexane/ethyl acetate solution gives the title product as a yellow solid, mp >200° C.

EXAMPLE 20

Preparation of
4-(p-Chlorophenyl)-2-(Trifluoromethyl)-3-Oxazolin-5-One

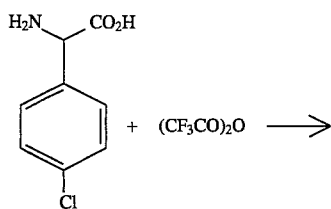

A solution of (p-chlorophenyl) glycine ( 5.05 g, 27.3 mmol) and trifluoroacetic anhydride (22.90 g, 109.2 mmol) in toluene is refluxed for five minutes and concentrated in vacuo to obtain the title product as a clear orange oil which is identified by high performance liquid chromatography analysis.

Using essentially the same procedure, but substituting α-amino-2-thiopheneacetic acid for (p-chlorophenyl)glycine, 4-(2-thienyl)-2-(trifluoromethyl)-3-oxazolin-5-one is obtained as a brown oil.

EXAMPLE 21

Preparation of
5-(p-Chlorophenyl)-3-(5-Nitro-2-Thienyl)-2-(Trifluoromethyl)Pyrrole

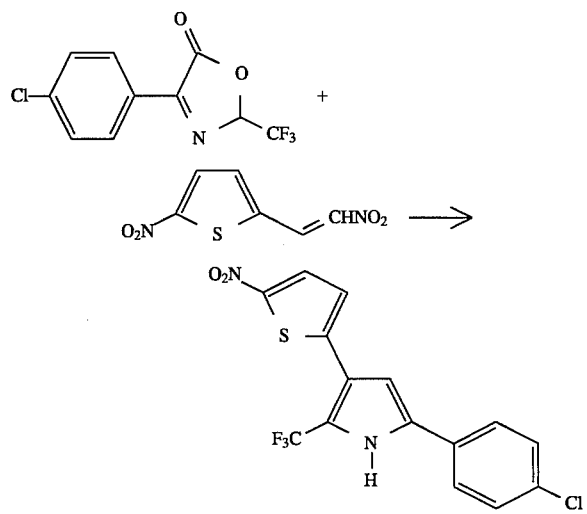

Triethylamine (1.16 g, 11.3 mmol) is added to a solution of 4-(p-chlorophenyl)-2-(trifluoromethyl)-3-oxazolin-5-one (2.97 g, 11.3 mmol) and 2-nitro-5-(2-nitrovinyl)thiophene (2.26 g, 11.3 mmol) in acetonitrile near reflux. The reaction mixture is refluxed for one hour, stirred overnight at room temperature and concentrated in vacuo to obtain a red oil. Chromatography of the oil gives the title product as a tan solid, mp 166°–169° C.

Using essentially the same procedure, but substituting 2-(2-nitrovinyl)furan for 2-nitro-5-(2-nitrovinyl)thiophene, 5-(p-chlorophenyl)-3-(2-furyl)-2-trifluoromethyl)pyrrole is obtained as a tan solid, mp 65°–66° C.

And using essentially the same procedure, but substituting 4-(2-thienyl)-2-(trifluoromethyl)-3-oxazolin-5-one for 4-(p-chlorophenyl)-2-(trifluoromethyl)-3-oxazolin-5-one and 2-chloroacrylonitrile for 2-nitro-5-(2-nitrovinyl)thiophene, 2-(2-thienyl)-5-trifluoromethyl)pyrrole-3-carbonitrile is obtained as a tan solid, mp 210° C.

EXAMPLE 22

Preparation of
2-(p-Chlorophenyl)-3-Nitro-4-(5-Nitro-2-Thienyl)-5-(Trifluoromethyl)Pyrrole

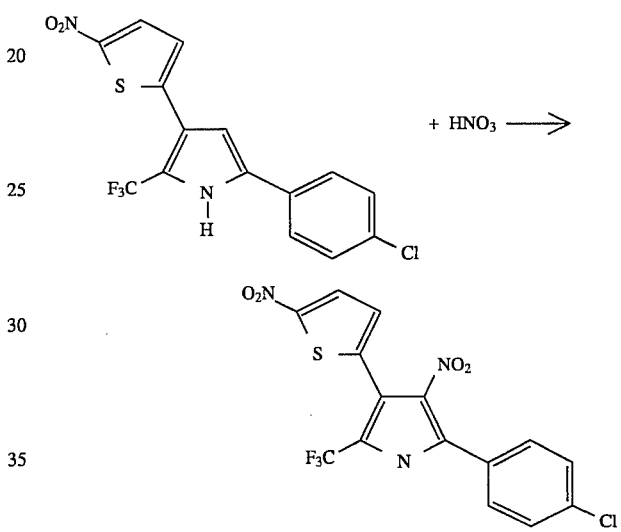

A 90% nitric acid solution (0.02 g, 0.28 mmol) is added to a solution of 5-(p-chlorophenyl)-3-(5-nitro-2-thienyl)-2-(trifluoromethyl)pyrrole (0.13 g, 0.34 mmol) in acetic anhydride. The reaction mixture is stirred at room temperature for ten minutes, treated with additional 90% nitric acid solution (0.02 g, 0.28 mmol), stirred at room temperature for 15 minutes, poured into water, stirred at room temperature overnight and extracted with ether. The combined organic extracts are dried over $MgSO_4$ and concentrated in vacuo to obtain the title product as a tan solid which is identified by $^1$HNMR spectral analysis.

EXAMPLE 23

Preparation of
4-Bromo-2-(5-Bromo-2-Thienyl)-5-(Trifluoromethyl) Pyrrole-3-Carbonitrile and 4-Bromo-2-[3(or 4),5-Dibromo-2-Thienyl]-5-(Trifluoromethyl) Pyrrole-3-Carbonitrile

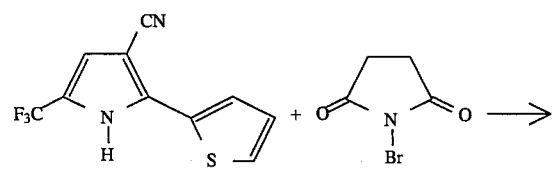

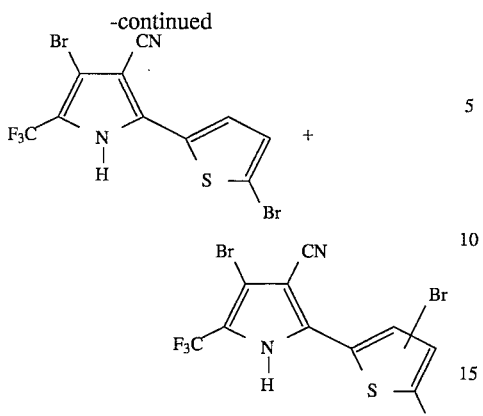

A solution of N-bromosuccinimide (0.84 g, 4.63 mmol) and 2-(2-thienyl)-5-(trifluoromethyl)pyrrole-3-carbonitrile (1.02 g, 4.21 mmol) in tetrahydrofuran is stirred at room temperature for 20 minutes, treated with additional N-bromosuccinimide (0.84 g, 4.63 mmol), stirred at room temperature for 20 minutes, stirred at reflux for two hours and poured into water. The aqueous mixture is filtered to obtain solids and filtrate. A mixture of the solids in toluene is heated, filtered and dried to give 4-bromo-2-(5-bromo-2-thienyl)-5-(trifluoromethyl)pyrrole-3-carbonitrile as a solid, mp 254° C. (dec.). The filtrate obtained from the aqueous mixture is concentrated in vacuo and chromatographed using silica gel and a (4:1) hexane/ethyl acetate solution to obtain 4-bromo-2-[3(or 4),5-dibromo-2-thienyl]-5-(trifluoromethyl)pyrrole-3-carbonitrile as a solid, mp 203° C.

EXAMPLE 24

Preparation of 2-[1-(5-Bromo-3-Thienyl)-2-Nitroethyl]-4-(p-Chlorophenyl)-2-(Trifluoromethyl)-3-Oxazolin-5-One

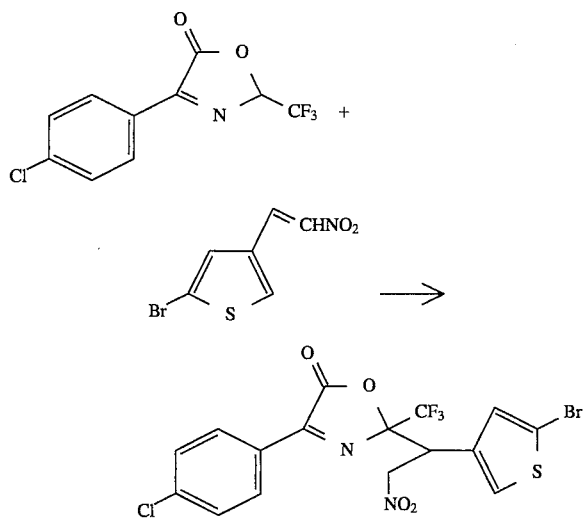

A solution of triethylamine (0.30 g, 3 mmol) in toluene is added to a solution of 4-(p-chlorophenyl)-2-(trifluoromethyl)-3-oxazolin-5-one (10.0 g, 38 mmol) and 2-bromo-4-(2-nitrovinyl)thiophene (8.98 g, 32 mmol) in toluene at 0° C. The reaction mixture is warmed to room temperature and diluted with dilute hydrochloric acid and ether. The organic layer is separated, dried over MgSO₄, concentrated in vacuo, diluted with hexane, stirred at reflux, cooled to room temperature and decanted to obtain a clear solution. The solution is concentrated in vacuo and chromatographed to give the title product.

EXAMPLE 25

Preparation of 3-(5-Bromo-3-Thienyl)-5-(p-Chlorophenyl)-2-(Trifluoromethyl)Pyrrole and 3-(5-Bromo-3-Thienyl)-5-(p-Chlorophenyl)-4-Nitro-2-(Trifluoromethyl)Pyrrole

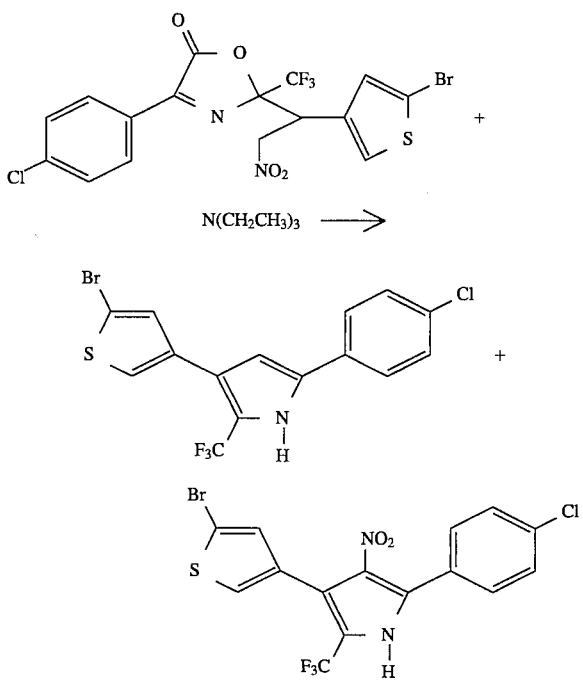

A solution of triethylamine (3.24 g, 32.1 mmol) in acetonitrile is added slowly to a solution of 2-[1-(5-bromo-3-thienyl)-2-nitroethyl]-4-(p-chlorophenyl)-2-(trifluoromethyl)-3-oxazolin-5-one (13.30 g, 26.8 mmol) in acetonitrile. The reaction mixture is stirred at room temperature for several minutes and diluted with dilute hydrochloric acid. The organic layer is separated, dried over MgSO₄ and concentrated in vacuo to obtain a black residue. Column chromatography of the residue using silica gel and a (9:1) hexane/ethyl acetate solution gives several solids. One of the solids is stirred in cold 1,2-dichloroethane, filtered and dried to give 3-(5-bromo-3-thienyl)-5-(p-chlorophenyl)-2-(trifluoromethyl)pyrrole as a light tan solid, mp 112°–115° C. Another solid is diluted with hexane and the mixture is refluxed, cooled to room temperature and filtered to obtain 3-(5-bromo-3-thienyl)-5-(p-chlorophenyl)-4-nitro-2-(trifluoromethyl)pyrrole as a yellow solid, mp 174°–176° C.

EXAMPLE 26

Preparation of
3-(5-Bromo-4-Nitro-3-Thienyl)-5-(p-Chlorophenyl)-
4-Nitro-2-(Trifluoromethyl)Pyrrole)

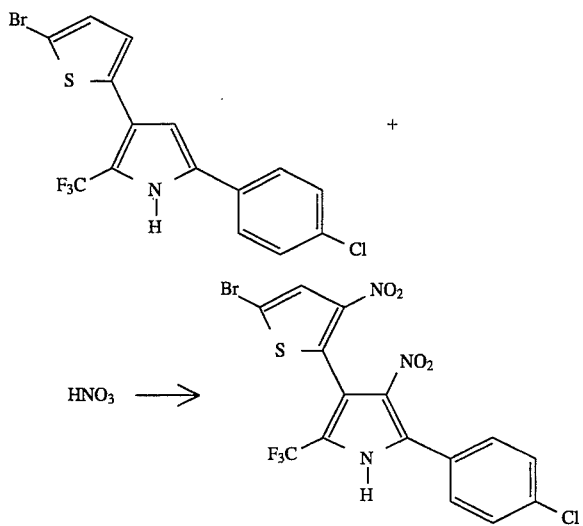

A solution of 3-(5-bromo-3-thienyl)-5-(p-chlorophenyl)-2-(trifluoromethyl)pyrrole (0.70 g, 1.7 mmol) and 90% nitric acid (0.145 g, 0.1 mL, 2.1 mmol) in acetic anhydride is stirred at room temperature for 20 minutes, treated with additional 90% nitric acid (several drops) and diluted with water. The solids are collected by filtration and dried overnight at 60° C. in a vacuum oven to give the title product as a solid, mp 186°–190° C.

EXAMPLE 27

Preparation of
2-(p-Chlorophenyl)-4-(4,5-Dibromo-3-Thienyl)-
3-Nitro-5-(Trifluoromethyl)Pyrrole)

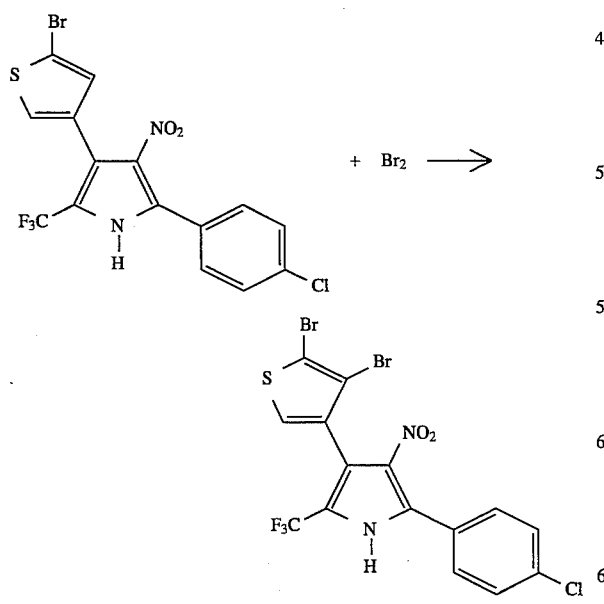

A solution of 3-(5-bromo-3-thienyl)-5-(p-chlorophenyl)-4-nitro-2-(trifluoromethyl)pyrrole (0.50 g, 1.1 mmol), bromine (0.20 g, 1.3 mmol) and sodium acetate (0.11 g, 1.3 mmol) in acetic acid (10 mL) is heated overnight at 50° C. and poured into water. The solids are collected and recrystallized from 1,2-dichloroethane to give the title product as a yellow solid, mp 241°–242° C.

EXAMPLE 28

Evaluation of In Vitro Fungicidal Activity of Test Compounds

Test compounds are dissolved or suspended in acetone and dispersed into cell well plates containing a suspension of ground fungal mycelia in a nutrient broth. Assay plates are incubated for 3–4 days at 21° C. Growth inhibition is measured visually and is rated using the following scale:

| Rating Scale | |
|---|---|
| Rating | Range % Inhibition |
| 0 | 0 |
| 1 | 1–29 |
| 3 | 30–59 |
| 5 | 60–89 |
| 7 | 90–99 |
| 9 | 100 |
| — | no evaluation |

Untreated controls, solvent blanks and reference standards are included in each test.

Assay fungi include the plant pathogens, *Pythium ultimum* (Pythul); *Rhizoctonia solani* (Rhizso); *Fusarium oxysporum* f. sp. cucumerinum (Fusoxc); and *Pseudocercosporella herpotrichoides* (Psdche).

When more than one test is run, the data are averaged. The data obtained are shown in Table I.

Compounds employed in this in vitro fungicidal evaluation and in the in vivo fungicidal evaluation in the following example are given a compound number and identified by name. Data in Table I are reported by compound number.

| COMPOUNDS EVALUATED AS FUNGICIDAL AGENTS | |
|---|---|
| Compound No. | |
| 1 | 4,5-Dichloro-2-(3-chloro-2-benzofuranyl)-pyrrole-3-carbonitrile |
| 2 | 2-(2-Thienyl)-5-(trifluoromethyl)pyrrole-3-carbonitrile |
| 3 | 4-Bromo-2-(5-bromo-2-thienyl)-5-(trifluoromethyl)pyrrole-3-carbonitrile |
| 4 | 5-(p-Chlorophenyl)-3-(2-furyl)-2-(trifluoromethyl)pyrrole |
| 5 | 2-(p-Chlorophenyl)-3-nitro-4-(5-nitro-2-thienyl)-5-(trifluoromethyl)pyrrole |
| 6 | 2-Chloro-5-(5-chloro-2-thienyl)pyrrole-3-carbonitrile |
| 7 | 4-Bromo-2-chloro-5-(5-chloro-2-thienyl)-pyrrole-3-carbonitrile |
| 8 | 3-(5-Bromo-3-thienyl)-5-(p-chlorophenyl)-4-nitro-2-(trifluoromethyl)pyrrole |
| 9 | 3-(5-Bromo-3-thienyl)-5-(p-chlorophenyl)-2-(trifluoromethyl)pyrrole |
| 10 | 2-(p-Chlorophenyl)-4-(4,5-dibromo-3-thienyl)-3-nitro-5-(trifluoromethyl)pyrrole |

-continued

COMPOUNDS EVALUATED AS FUNGICIDAL AGENTS

| Compound No. | |
|---|---|
| 11 | 2-(2-Furyl)-5-(trifluoromethyl)pyrrole-3-carbonitrile |
| 12 | 4-Chloro-2-(2-thienyl)-5-(trifluoromethyl)-pyrrole-3-carbonitrile |
| 13 | 4-Bromo-2-(5-bromo-2-thienyl)-1-(ethoxymethyl)-5-(trifluoromethyl)pyrrole-3-carbonitrile |
| 14 | 2-(5-Bromo-2-furyl)-5-(trifluoromethyl)-pyrrole-3-carbonitrile |
| 15 | 2-(5-Bromo-2-thienyl)-5-(trifluoromethyl)-pyrrole-3-carbonitrile |
| 16 | 2-(5-Chloro-2-thienyl)-5-(trifluoromethyl)-pyrrole-3-carbonitrile |
| 17 | 4-Bromo-2-(5-chloro-2-thienyl)-5-(trifluoromethyl)pyrrole-3-carbonitrile |
| 18 | 4-Bromo-2-(5-chloro-2-thienyl)-1-(ethoxymethyl)-5-(trifluoromethyl)pyrrole-3-carbonitrile |
| 19 | 4-Bromo-2-(5-bromo-2-furyl)-5-(trifluoromethyl)pyrrole-3-carbonitrile |
| 20 | 2-(4-Bromo-2-thienyl)-5-(trifluoromethyl)-pyrrole-3-carbonitrile |
| 21 | 4-Bromo-2-(4,5-dibromo-2-thienyl)-5-(trifluoromethyl)pyrrole-3-carbonitrile |
| 22 | 4-Bromo-2-(5-bromo-2-furyl)-1-(ethoxymethyl)-5-(trifluoromethyl)pyrrole-3-carbonitrile |

TABLE I

In Vitro Fungicidal Evaluations

| Compound Number | Rate (ppm) | FUSOXC | PSDCHE | PYTHUL | RHIZSO |
|---|---|---|---|---|---|
| 1 | 25 | — | 1 | 1 | 1 |
| 2 | 25 | — | 4 | 9 | 4 |
| 3 | 25 | — | 3 | 8 | 8 |
| 4 | 25 | — | 9 | 5 | 8 |
| 5 | 25 | 3 | 5 | 2 | 7 |
| 6 | 25 | 4 | 5 | 8 | 5 |
| 7 | 25 | 0 | 4 | 8 | 5 |
| 8 | 25 | 0 | 0 | 0 | 3 |
| 9 | 25 | 0 | 0 | 0 | 5 |
| 10 | 25 | 2 | 0 | 0 | 8 |
| 11 | 25 | 0 | 0 | 7 | 4 |
| 12 | 25 | 0 | 0 | 7 | 7 |
| 13 | 25 | 0 | 0 | 0 | 3 |
| 14 | 25 | 0 | 0 | 2 | 3 |
| 15 | 25 | 0 | 0 | 0 | 5 |
| 16 | 25 | 0 | 0 | 0 | 5 |
| 17 | 25 | 0 | 0 | 3 | 5 |
| 18 | 25 | 0 | 0 | 0 | 3 |
| 19 | 25 | 0 | 0 | 0 | 0 |
| 20 | 25 | 0 | 0 | 0 | 0 |
| 21 | 25 | 0 | 0 | 0 | 0 |
| 22 | 25 | 0 | 0 | 0 | 0 |

EXAMPLE 29

Evaluation of In Vivo Fungicidal Activity of Test Compounds

Test compounds are dissolved or suspended in acetone and diluted with deionized water containing about 0.05% TWEEN 20®, a polyoxyethylene sorbitan monolaurate surfactant manufactured by Atlas Chemical Industries, to give a concentration of 400 ppm or 200 ppm.

Host plants are sprayed with the test solution, dried and inoculated with fungi. When disease symptom development is optimal, the plants are rated for disease control according to the rating scale shown below. Each test contains inoculated treated plants, inoculated untreated plants and a reference standard. When more than one test is run, the data are averaged. The data obtained are shown in Table II. The compounds evaluated are reported by compound number given in example 28.

| Rating Scale | |
|---|---|
| Rating | Range % Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| — | no evaluation |

PHYTOPATHOGENIC FUNGI

| Symbol | Disease | Pathogen |
|---|---|---|
| AS | Apple Scab | Venturia inaequalis |
| GDM | Grape Downy Mildew | Plasmopara viticola |
| PB | Pepper Botrytis | Botrytis cinerea |
| RB | Rice Blast | Pyricularia oryzae |
| SBC | Sugar Beet Cercospora | Cercospora beticola |
| WLR | Wheat Leaf Rust | Puccinia recondita f. sp. tritici |
| WPM | Wheat Powdery Mildew | Erysiphe graminis f. sp. tritici |

TABLE II

In Vivo Fungicidal Evaluations

| Compound Number | Rate (ppm) | AS | GDM | PB | RB | SBC | WLR | WPM |
|---|---|---|---|---|---|---|---|---|
| 1 | 400 | 0 | — | 2 | 4 | 0 | 2 | 0 |
| 2 | 400 | 9 | 9 | — | 5 | 0 | 9 | 9 |
| 3 | 400 | 9 | 9 | — | 0 | — | 9 | 7 |
| 4 | 400 | 2 | 8 | 0 | 1 | 0 | 6 | 0 |
| 5 | 400 | 4 | 9 | 0 | 0 | — | 6 | 0 |
| 6 | 400 | 9 | 7 | 0 | 0 | 6 | 6 | 0 |
| 7 | 400 | 8 | 0 | 0 | 0 | 0 | 7 | 0 |
| 8 | 400 | 8 | 9 | 0 | 4 | — | 7 | 0 |
| 9 | 400 | 0 | 6 | 0 | 0 | 0 | 0 | 0 |
| 10 | 400 | 0 | 7 | 0 | 7 | 0 | — | 4 |
| 11 | 200 | 0 | 0 | 0 | 0 | 0 | — | — |
| 12 | 200 | 4 | 8 | 0 | 0 | 0 | — | 8 |
| 13 | 200 | 0 | 0 | 0 | 0 | 0 | — | 9 |
| 14 | 200 | 0 | 6 | 0 | 0 | 0 | — | 6 |

What is claimed is:

1. A method for control or amelioration of a disease caused by a phytopathogenic fungus which comprises contacting said fungus with a fungicidally effective amount of a compound having the structural formula

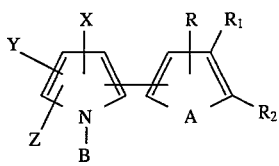

wherein

R, $R_1$ and $R_2$ are each independently hydrogen, halogen, $NO_2$ or CHO, and when $R_1$ and $R_2$ are taken together with the carbon atoms to which they are attached, they may form a ring in which $R_1R_2$ is represented by the structure:

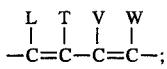

L, T, V and W are each independently hydrogen, halogen, CN or $NO_2$;

A is S;

X is CN, $NO_2$, $C_1$–$C_6$ haloalkyl, $S(O)_mCF_2R_3$ or $C(S)NR_4R_5$;

$R_3$ is hydrogen, F, Cl, Br, C $CCl_3$;

m is an integer of 0, 1 or 2;

$R_4$ and $R_5$ are each independently hydrogen,
 $C_1$–$C_4$ alkyl optionally substituted with one or more halogen atoms, or
 phenyl optionally substituted with one or more halogen atoms,
  $NO_2$ groups,
  CN groups,
  $C_1$–$C_4$ alkyl groups optionally substituted with one or more halogen atoms, or
  $C_1$–$C_4$ alkoxy groups optionally substituted with one or more halogen atoms;

Y is hydrogen, halogen, $C_1$–$C_6$ haloalkyl, $S(O)_mCF_2R_3$, CN or
 phenyl optionally substituted with one or more halogen atoms,
  $NO_2$ groups,
  CN groups,
  $C_1$–$C_4$ alkyl groups optionally substituted with one or more halogen atoms, or
  Cl-$C_4$ alkoxy groups optionally substituted with one or more halogen atoms;

Z is hydrogen, halogen or $C_1$–$C_6$ haloalkyl;

B is $R_6$, $OR_6$ or CN;

$R_6$ is hydrogen, $C(O)R_7$, $CHR_8NHC(O)R_9$, $CH_2SQ$, $CHR_{10}OC(O)(CR_{11}R_{12})_nQ_1$,
 $C_1$–$C_6$ alkyl optionally substituted with one to three halogen atoms,
 one tri($C_1$–$C_4$ alkyl)silyl,
 one hydroxy,
 one cyano,
 one or two $C_1$–$C_4$ alkoxy groups optionally substituted with one to three halogen atoms,
 one $C_1$–$C_4$ alkylthio,
 one phenyl optionally substituted with one to three halogen atoms, one to three $C_1$–$C_4$ alkyl groups or one to three $C_1$–$C_4$ alkoxy groups,
 one phenoxy group optionally substituted with one to three halogen atoms, one to three $C_1$–$C_4$ alkyl groups or one to three $C_1$–$C_4$ alkoxy groups,
 one benzyloxy group optionally substituted on the phenyl ring with one to three halogen atoms, one to three $C_1$–$C_4$ alkyl groups or one to three $C_1$–$C_4$ alkoxy groups,
 one $C_1$–$C_6$ alkylcarbonyloxy group optionally substituted with one to three halogen atoms,
 one $C_2$–$C_6$ alkenylcarbonyloxy group optionally substituted with one to three halogen atoms,
 one phenylcarbonyloxy group optionally substituted with one to three halogen atoms, one to three $C_1$–$C_4$ alkyl groups or one to three $C_1$–$C_4$ alkoxy groups,
 one $C_1$–$C_6$ alkoxycarbonyl group optionally substituted with one to three halogen atoms or one to three $C_1$–$C_4$ alkoxy groups, or
 one benzylcarbonyloxy group optionally substituted on the phenyl ring with one to three halogen atoms, one to three $C_1$–$C_4$ alkyl groups or one to three $C_1$–$C_4$ alkoxy groups, $C_3$–$C_6$ alkenyl optionally substituted with one to three halogen atoms or one phenyl group, or $C_3$–$C_6$ alkynyl optionally substituted with one to three halogen atoms or one phenyl group;

$R_7$ is $C_1$–$C_6$ alkyl or $C_3$–$C_6$ cycloalkyl each optionally substituted with one to three halogen atoms,
 one hydroxy,
 one cyano,
 one or two $C_1$–$C_4$ alkoxy groups optionally substituted with one to three halogen atoms,
 one $C_1$–$C_4$ alkylthio,
 one phenyl group optionally substituted with one to three halogen atoms, one to three $C_1$–$C_4$ alkyl groups or one to three $C_1$–$C_4$ alkoxy groups,
 one phenoxy group optionally substituted with one to three halogen atoms, one to three $C_1$–$C_4$ alkyl groups or one to three $C_1$–$C_4$ alkoxy groups,
 one benzyloxy group optionally substituted on the phenyl ring with one to three halogen atoms, one to three $C_1$–$C_4$ alkyl groups or one to three $C_1$–$C_4$ alkoxy groups,
 one $C_1$–$C_6$ alkylcarbonyloxy group optionally substituted with one to three halogen atoms,
 one $C_2$–$C_6$ alkenylcarbonyloxy group optionally substituted with one to three halogen atoms,
 one phenylcarbonyloxy group optionally substituted with one to three halogen atoms, one to three $C_1$–$C_4$ alkyl groups or one to three $C_1$–$C_4$ alkoxy groups,
 one $C_1$–$C_6$ alkoxycarbonyl group optionally substituted with one to three halogen atoms or one to three $C_1$–$C_4$ alkoxy groups, or
 one benzyloxycarbonyl group optionally substituted on the phenyl ring with one to three halogen atoms, one to three $C_1$–$C_4$ alkyl groups or one to three $C_1$–$C_4$ alkoxy groups, $C_2$–$C_6$ alkenyl optionally substituted with one to three halogen atoms or one phenyl groups, $C_3$–$C_6$ alkynyl optionally substituted with one to three halogen atoms or one phenyl group, phenyl optionally substituted with one or more halogen atoms, $C_1$–$C_4$ alkyl groups, $C_1$–$C_4$ alkoxy groups, phenoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups, phenoxy optionally substituted with one or more halogen atoms, $C_1$–$C_4$ alkyl groups, $C_1$–$C_4$ alkoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups,
1- or 2-naphthyl,
2-, 3-, or 4-pyridyl optionally substituted with one to three halogen atoms,
$C_1$–$C_6$ alkoxy optionally substituted with one to three halogen atoms, or
$C_2$–$C_6$ alkenyloxy optionally substituted with one to three halogen atoms;

$R_8$ is hydrogen or $C_1$–$C_4$ alkyl;

$R_9$ is $C_1$–$C_6$ alkyl optionally substituted with one to three halogen atoms,
phenyl optionally substituted with one to three halogen atoms, CN groups, $NO_2$ groups, $C_1$–$C_4$ alkyl groups, $C_1$–$C_4$ alkoxy groups or $CF_3$ groups,
2- or 3-thienyl, or
2- or 3-furyl;

Q is

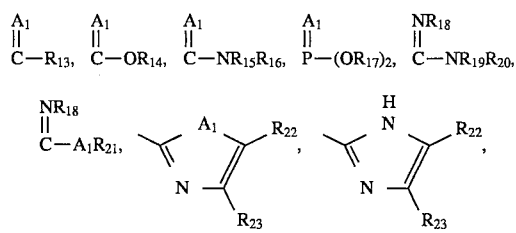

CN,
$C_1$–$C_6$ alkyl optionally substituted with one or more halogen atoms, CN groups or phenyl groups, or
phenyl optionally substituted with one or more halogen atoms, $C_1$–$C_4$ alkyl groups, $C_1$–$C_4$ alkoxy groups, CN groups, $NO_2$ groups, $CF_3$ groups or $NR_{24}R_{25}$ groups;

$A_1$ is O or S;

$R_{13}$ is $C_1$–$C_6$ alkyl or phenyl;

$R_{14}$ is $C_1$–$C_6$ alkyl;

$R_{15}$ and $R_{16}$ are each independently hydrogen, $C_1$–$C_6$ alkyl or may be taken together with the atom to which they are attached to form a 5- to 7-membered ring;

$R_{17}$ is $C_1$–$C_4$ alkyl;

$R_{18}$ is hydrogen, $C_1$–$C_4$ alkyl or may be taken together with either $R_{19}$ or $R_{21}$ and the atoms to which they are attached to form a 5- to 7-membered ring optionally substituted with one or two $C_1$–$C_4$ alkyl groups;

$R_{19}$ and $R_{20}$ are each independently hydrogen or $C_1$–$C_4$ alkyl;

$R_{21}$ is $C_1$–$C_4$ alkyl or when taken together with $R_{18}$ and the atoms to which they are attached may form a 5- to 7-membered ring optionally substituted with one or two $C_1$–$C_4$ alkyl groups;

$R_{22}$ and $R_{23}$ are each independently hydrogen or $C_1$–$C_4$ alkyl or when taken together may form a ring wherein $R_{22}R_{23}$ is represented by —CH=CH—CH=CH—;

$R_{24}$ and $R_{25}$ are each independently hydrogen or $C_1$–$C_4$ alkyl;

$R_{10}$ is hydrogen or $C_1$–$C_4$ alkyl;

$R_{11}$ and $R_{12}$ are each independently hydrogen, $C_1$–$C_6$ alkyl optionally substituted with one or more halogen atoms, $C_1$–$C_6$ alkoxy optionally substituted with one or more halogen atoms,
$C_1$–$C_6$ alkylthio optionally substituted with one or more halogen atoms, or
phenyl optionally substituted with one or more halogen atoms,
$NO_2$ groups;
CN groups,
$C_1$–$C_4$ alkyl groups optionally substituted with one or more halogen atoms, or
$C_1$–$C_4$ alkoxy groups optionally substituted with one or more halogen atoms, or
when $R_{11}$ and $R_{12}$ are taken together with the atom to which they are attached may form a $C_3$–$C_6$ cycloalkyl group optionally substituted with one to three $C_1$–$C_4$ alkyl groups, $C_2$–$C_6$ alkenyl groups or phenyl groups, or $R_{11}$ or $R_{12}$ may be taken together with $R_{26}$ and the atoms to which they are attached to form a 4- to 7-membered heterocyclic ring;

n is an integer of 0, 1, 2, 3 or 4;

$Q_1$ is $A_2R_{26}$,

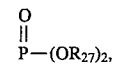

$NR_{28}R_{29}$, $CR_{30}R_{31}C(O)R_{32}$, or $C_3$–$C_6$ cycloalkyl optionally substituted with one or more $C_1$–$C_6$ alkyl groups,
$C_2$–$C_6$ alkenyl groups, or
phenyl groups optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

$A_2$ is O or $S(O)_p$;

p is an integer of 0, 1 or 2;

$R_{26}$ is hydrogen,
$C_1$–$C_6$ alkyl
$C_2$–$C_6$ alkenyl,
$C_2$–$C_6$ alkynyl,
phenyl optionally substituted with one or more halogen atoms,
$NO_2$ groups,
CN groups,
$C_1$–$C_4$ alkyl groups optionally substituted with one or more halogen atoms,
$C_1$–$C_4$ alkoxy groups optionally substituted with one or more halogen atoms,
$C(O)R_{33}$ provided p is O,
$C(O)R_{34}$ provided p is O,
$(CH_2CH_2O)_qR_{33}$, or

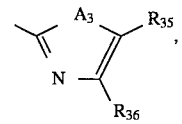

$R_{26}$ may be taken together with either $R_{11}$ or $R_{12}$ and the atoms to which they are attached to form a 4- to 7-membered heterocyclic ring;

$A_3$ is O or S;

$R_{33}$ is $C_1$–$C_6$ alkyl, $C_2$–$C_6$ alkenyl,
$C_2$–$C_6$ alkynyl, or
phenyl optionally substituted with one or more halogen atoms,
  $NO_2$ groups,
  CN groups,
  $C_1$–$C_4$ alkyl groups optionally substituted with one or more halogen atoms, or
  $C_1$–$C_4$ alkoxy groups optionally substituted with one or more halogen atoms;

q is an integer of 1, 2 or 3;

$R_{34}$ is $OR_{37}$ or $NR_{38}R_{39}$;

$R_{37}$ is $C_1$–$C_6$ alkyl or phenyl optionally substituted with one or more halogen atoms,
  $NO_2$ groups,
  CN groups,
  $C_1$–$C_4$ alkyl groups optionally substituted with one or more halogen atoms, or
  $C_1$–$C_4$ alkoxy groups optionally substituted with one or more halogen atoms;

$R_{38}$ and $R_{39}$ are each independently hydrogen or $C_1$–$C_4$ alkyl;

$R_{35}$ and $R_{36}$ are each independently hydrogen or $C_1$–$C_4$ alkyl, or when taken together may form a ring wherein $R_{35}R_{36}$ is represented by —CH=CH—CH=CH—;

$R_{27}$ is $C_1$–$C_4$ alkyl;

$R_{28}$ is hydrogen,
  $C_1$–$C_6$ alkyl,
  $C_2$–$C_6$ alkenyl,
  $C_2$–$C_6$ alkynyl, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms, or
  $R_{28}$ may be taken together with either $R_{11}$ or $R_{12}$ and the atoms to which they are attached to form a 4- to 7-membered heterocyclic ring;

$R_{29}$ is hydrogen,
  $C_1$–$C_6$ alkyl,
  $C_2$–$C_6$ alkenyl,
  $C_2$–$C_6$ alkynyl,
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms,
  $C(A_4)R_{40}$,
  CN,
  $SO_2R_{41}$, or
  $C(O)CHR_{42}NHR_{43}$;

$A_4$ is O or S;

$R_{40}$ is $OR_{44}$, $CO_2R_{44}$, $NR_{45}R_{46}$,
  $C_1$–$C_6$ alkyl optionally substituted with one to three halogen atoms,
  $C_2$–$C_6$ alkenyl,
  $C_2$–$C_6$ alkynyl, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;

$R_{44}$ is $C_1$–$C_6$ alkyl optionally substituted with one phenyl group, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;

$R_{45}$ and $R_{46}$ are each independently hydrogen or $C_1$–$C_4$ alkyl;

$R_{41}$ is $NR_{47}R_{48}$,
  $C_1$–$C_6$ alkyl,
  $C_2$–$C_6$ alkenyl,
  $C_2$–$C_6$ alkynyl, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;

$R_{47}$ and $R_{48}$ are each independently hydrogen or $C_1$–$C_4$ alkyl;

$R_{42}$ is hydrogen,
  $C_1$–$C_4$ alkyl optionally substituted with one hydroxy group,
    one $SR_{49}$ group,
    one $C(O)NH_2$ group,
    one $NH_2$ group,
    one NHC(=NH)$NH_2$ group,
    one $CO_2H$ group,
    one phenyl group optionally substituted with one hydroxy group,
    one 3-indolyl group or
    one 4-imidazolyl group;

$R_{49}$ is hydrogen or $C_1$–$C_4$ alkyl;

$R_{43}$ is $C(A_4)R_{50}$;

$R_{50}$ is $C_1$–$C_6$ alkyl optionally substituted with one or more halogen atoms,
  $C_1$–$C_6$ alkoxyalkyl,
  $C_1$–$C_6$ alkylthio,
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms,
  $OR_{44}$,
  $CO_2R_{44}$ or
  $NR_{45}R_{46}$;

$R_{30}$ and $R_{31}$ are each independently hydrogen,
  $C_1$–$C_6$ alkyl optionally substituted with one or more halogen atoms,
  $C_1$–$C_6$ alkoxy optionally substituted with one or more halogen atoms, $C_1$–$C_6$ alkylthio optionally substituted with one or more halogen atoms,
phenyl optionally substituted with one or more halogen atoms,
CN groups,
$NO_2$ groups,
$C_1$–$C_4$ alkyl groups optionally substituted with one or more halogen atoms, or
$C_1$–$C_4$ alkoxy groups optionally substituted with one or more halogen atoms, or
when $R_{30}$ and $R_{31}$ are taken together with the atom to which they are attached may form a $C_3$–$C_6$ cycloalkyl group optionally substituted with one to three $C_1$–$C_4$ alkyl groups, $C_2$–$C_6$ alkenyl groups or phenyl groups;

$R_{32}$ is $OR_{51}$, $NR_{47}R_{48}$, $C_1$–$C_4$ alkyl or phenyl optionally substituted with one or more halogen atoms,
CN groups,
$NO_2$ groups,
$C_1$–$C_4$ alkyl groups optionally substituted with one or more halogen atoms, or
$C_1$–$C_4$ alkoxy groups optionally substituted with one or more halogen atoms; and $R_{51}$ is $C_1$–$C_4$ alkyl or phenyl optionally substituted with one or more halogen atoms,
CN groups,
$NO_2$ groups,
$C_1$–$C_4$ alkyl groups optionally substituted with one or more halogen atoms, or
$C_1$–$C_4$ alkoxy groups optionally substituted with one or more halogen atoms;

provided that when X is $S(O)_mCF_2R_3$ and Z is hydrogen, then Y is hydrogen, halogen, $C_1$–$C_6$ haloalkyl, $S(O)_mCF_2R_3$ or CN; and further provided that when the pyrrole ring is substituted with hydrogen at each of the pyrrole carbon atoms adjacent to the ring nitrogen atom, then X cannot be CN or $NO_2$.

2. The method according to claim 1 wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

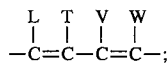

L, T, V and W are each independently hydrogen, halogen, CN or $NO_2$;

A is S;

X is CN, $NO_2$, $C_1$–$C_6$ haloalkyl, $S(O)_mCF_2R_3$ or $C(S)NR_4R_5$;

$R_3$ is hydrogen, F, Cl, Br, $CF_2H$, $CCl_2H$, $CClFH$, $CF_3$ or $CCl_3$;

m is an integer of 0, 1 or 2;

$R_4$ and $R_5$ are each independently hydrogen,
$C_1$–$C_4$ alkyl optionally substituted with one or more halogen atoms or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Y is hydrogen, halogen, $C_1$–$C_6$ haloalkyl, $S(O)_mCF_2R_3$, CN or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $C_1$–$C_6$ haloalkyl;

B is $R_6$ or CN;

$R_6$ is hydrogen, $C(O)_7$ or
$C_1$–$C_6$ alkyl optionally substituted with one to three halogen atoms,
one cyano,
one $C_1$–$C_4$ alkoxy group,
one $C_1$–$C_6$ alkylcarbonyloxy group,
one phenylcarbonyloxy group, or
one benzylcarbonyloxy groups; and $R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

3. The method according to claim 2 wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

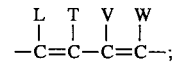

L, T, V and W are each independently hydrogen, halogen, CN or $NO_2$;

A is or S;

X is CN, $NO_2$ or $C_1$–$C_6$ haloalkyl;

Y is hydrogen, halogen, $C_1$–$C_6$ haloalkyl or phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $C_1$–$C_6$ haloalkyl;

B is $R_6$ or CN;

$R_6$ is hydrogen, $C(O)R_7$ or $C_1$–$C_6$ alkyl optionally substituted with one to three halogen atoms,
one cyano,
one $C_1$–$C_4$ alkoxy group,
one $C_1$–$C_6$ alkylcarbonyloxy group,
one phenylcarbonyloxy group, or
one benzylcarbonyloxy group; and $R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

4. The method according to claim 3 wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

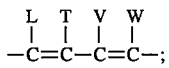

L, T, V and W are each independently hydrogen, halogen, CN or $NO_2$;

A is S;

X is CN, $NO_2$ or $C_1$–$C_6$ haloalkyl;

Y is hydrogen, halogen, $C_1$–$C_6$ haloalkyl or phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is halogen or $C_1$–$C_6$ haloalkyl;

B is $R_6$ or CN;

$R_6$ is hydrogen, $C(O)R_7$ or $C_1$–$C_6$ alkyl optionally substituted with one to three halogen atoms,
one cyano,
one $C_1$–$C_4$ alkoxy group,
one $C_1$–$C_6$ alkylcarbonyloxy group,
one phenylcarbonyloxy group, or
one benzylcarbonyloxy group; and $R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

5. The method according to claim 3 wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

—CH=CH—CH=CH—;

A is S;

X is CN or $NO_2$;

Y is halogen, $CF_3$ or phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $CF_3$; and

B is hydrogen or $C_1$–$C_6$ alkyl substituted with one $C_1$–$C_4$ alkoxy group.

6. The method according to claim 5 wherein

R, $R_1$ and $R_2$ are each independently hydrogen, halogen or $NO_2$;

A is S;

X is CN or $NO_2$;

Y is halogen, $CF_3$ or phenyl optionally substituted with one or more halogen atoms,
$NO_2$ groups,
CN Groups,
$C_1$–$C_4$ alkyl groups optionally substituted with one or more halogen atoms, or
$C_1$–$C_4$ alkoxy groups optionally substituted with one or more halogen atoms;

Z is $CF_3$; and

B is hydrogen or $C_1$–$C_6$ alkyl substituted with one $C_1$–$C_4$ alkoxy group.

7. The method according to claim 5 wherein the compound is selected from the group consisting of 2-(2-thienyl)-5-(trifluoromethyl)pyrrole-3-carbonitrile;

4-bromo-2-(5-bromo-2-thienyl)-5-(trifluoromethyl)pyrrole-3-carbonitrile;

3-(5-bromo-3-thienyl)-5-(p-chlorophenyl)-4-nitro-2-(trifluoromethyl)pyrrole;

2-chloro-5-(5-chloro-2-thienyl)pyrrole-3-carbonitrile; and 2-(p-chlorophenyl)-3-nitro-4-(5-nitro-2-thienyl)-5-(trifluoromethyl)pyrrole.

8. The method according to claim 1 wherein the compound is applied at a concentration of about 20 ppm to 1,000 ppm.

9. A method for the protection of a plant, plant seed or tuber from fungal infestation and disease which comprises applying to the plant, plant seed or tuber, or to the medium or water in which it is growing, a fungicidally effective amount of a compound having the structural formula

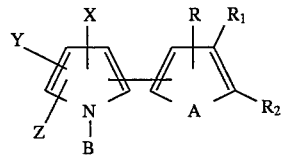

wherein R, $R_1$, $R_2$, A, X, Y, Z and B are as described in claim 1.

10. The method according to claim 9 wherein R, $R_1$, $R_2$, A, X, Y, Z and B are as described in claim 2.

11. The method according to claim 10 wherein R, $R_1$, $R_2$, A, X, Y, Z and B are as described in claim 3.

12. The method according to claim 11 wherein R, $R_1$, $R_2$, A, X, Y, Z and B are as described in claim 4.

13. The method according to claim 11 wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

—CH=CH—CH=CH—;

A is S;

X is CN or $NO_2$;

Y is halogen, $CF_3$ or phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $CF_3$; and

B is hydrogen or $C_1$–$C_6$ alkyl substituted with one $C_1$–$C_4$ alkoxy group.

14. The method according to claim 13 wherein R, $R_1$ and $R_2$ are each independently hydrogen, halogen or $NO_2$;

A is S;

X is CN or $NO_2$;

Y is halogen, $CF_3$ or phenyl optionally substituted with one or more halogen atoms,
  $NO_2$ groups,
  CN groups,
  $C_1$–$C_4$ alkyl groups optionally substituted with one or more halogen atoms, or
  $C_1$–$C_4$ alkoxy groups optionally substituted with one or more halogen atoms;

Z is $CF_3$; and

B is hydrogen or $C_1$–$C_6$ alkyl substituted wtih one $C_1$–$C_4$ alkoxy group.

15. The method according to claim 13 wherein the compound is selected from the group consisting of 2-(2-thienyl)-5-(trifluoromethyl)pyrrole-3-carbonitrile;

4-bromo-2-(5-bromo-2-thienyl)-5-(trifluoromethyl)pyrrole-3-carbonitrile;

3-(5-bromo-3-thienyl)-5-(p-chlorophenyl)-4-nitro-2-(trifluoromethyl)pyrrole;

2-chloro-5-(5-chloro-2-thienyl)pyrrole-3-carbonitrile; and 2-(p-chlorophenyl)-3-nitro-4-(5-nitro-2-thienyl)-5-(trifluoromethyl)pyrrole.

16. A composition for controlling phytopathogenic fungi which comprises an inert liquid or solid carrier and a fungicidally effective amount of a compound having the structural formula

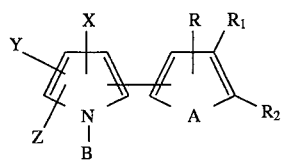

wherein R, $R_1$, $R_2$, A, X, Y, Z and B are as described in claim 1.

17. The composition according to claim 16 wherein R, $R_1$, $R_2$, A, X, Y, Z and B are as described in claim 2.

18. The composition according to claim 17 wherein R, $R_1$, $R_2$, A, X, Y, Z and B are as described in claim 3.

19. The composition according to claim 18 wherein R, $R_1$, $R_2$, A, X, Y, Z and B are as described in claim 4.

20. The composition according to claim 18 wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure: —CH=CH—CH=CH—;

A is S;

X is CN or $NO_2$;

Y is halogen, $CF_3$ or phenyl optionally substituted with one or more halogen atoms,
  $NO_2$ groups,
  CN groups,
  $C_1$–$C_4$ alkyl groups optionally substituted with one or more halogen atoms, or
  $C_1$–$C_4$ alkoxy groups optionally substituted with one or more halogen atoms;

Z is hydrogen, halogen or $CF_3$; and

B is hydrogen or $C_1$–$C_6$ alkyl substituted with one $C_1$–$C_4$ alkoxy group.

* * * * *